US012390435B2

(12) United States Patent
Freeman et al.

(10) Patent No.: US 12,390,435 B2
(45) Date of Patent: Aug. 19, 2025

(54) ELECTROPHILES AND ELECTROPHILE PRO-DRUGS AS RAD51 INHIBITORS

(71) Applicant: University of Pittsburgh—Of the Commonwealth System of Higher Education, Pittsburgh, PA (US)

(72) Inventors: Bruce A. Freeman, Pittsburgh, PA (US); Carola Neumann, Pittsburgh, PA (US); Francisco J. Schopfer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1026 days.

(21) Appl. No.: 17/290,963

(22) PCT Filed: Nov. 14, 2019

(86) PCT No.: PCT/US2019/061474
§ 371 (c)(1),
(2) Date: May 3, 2021

(87) PCT Pub. No.: WO2020/102529
PCT Pub. Date: May 22, 2020

(65) Prior Publication Data
US 2022/0040134 A1 Feb. 10, 2022

Related U.S. Application Data

(60) Provisional application No. 62/767,424, filed on Nov. 14, 2018.

(51) Int. Cl.
| | |
|---|---|
| *A61K 31/201* | (2006.01) |
| *A61K 31/231* | (2006.01) |
| *A61K 31/4184* | (2006.01) |
| *A61K 31/454* | (2006.01) |
| *A61K 31/4745* | (2006.01) |
| *A61K 31/502* | (2006.01) |
| *A61K 31/5025* | (2006.01) |
| *A61K 31/55* | (2006.01) |
| *A61K 31/704* | (2006.01) |
| *A61K 33/243* | (2019.01) |
| *A61P 35/00* | (2006.01) |
| *C07C 205/50* | (2006.01) |

(52) U.S. Cl.
CPC .......... *A61K 31/201* (2013.01); *A61K 31/231* (2013.01); *A61K 31/4184* (2013.01); *A61K 31/454* (2013.01); *A61K 31/4745* (2013.01); *A61K 31/502* (2013.01); *A61K 31/5025* (2013.01); *A61K 31/55* (2013.01); *A61K 31/704* (2013.01); *A61K 33/243* (2019.01); *A61P 35/00* (2018.01); *C07C 205/50* (2013.01)

(58) Field of Classification Search
CPC ................ A61K 31/201; A61K 31/231; A61K 31/4184; A61K 31/454; A61K 31/4745; A61K 31/502; A61K 31/5025; A61K 31/55; A61K 31/704; A61K 33/243; A61K 31/10; A61K 31/202; A61K 45/06; A61P 35/00; C07C 205/50; A61N 2005/1098

See application file for complete search history.

(56) References Cited

U.S. PATENT DOCUMENTS

| | | | |
|---|---|---|---|
| 7,776,916 | B2 | 8/2010 | Freeman et al. |
| 8,309,526 | B2 | 11/2012 | Freeman et al. |
| 8,324,277 | B2 | 12/2012 | Freeman |
| 8,735,449 | B2 | 5/2014 | Freeman |
| 9,006,473 | B2 | 4/2015 | Freeman et al. |
| 9,066,902 | B2 | 6/2015 | Freeman et al. |
| 9,186,408 | B2 | 11/2015 | Freeman et al. |

(Continued)

FOREIGN PATENT DOCUMENTS

| | | |
|---|---|---|
| WO | WO 2009/155439 A2 | 12/2009 |
| WO | WO 2011/041639 A2 | 4/2011 |

(Continued)

OTHER PUBLICATIONS

Asan et al., "Electrophilic fatty acids impair RAD51 function and potentiate the effects of DNA-damaging agents on growth of triple-negative breast cells," *J. Biol. Chem.*, 294(2): 397-404, Nov. 26, 2018.

(Continued)

*Primary Examiner* — Robert A Wax
*Assistant Examiner* — Quanglong N Truong
(74) *Attorney, Agent, or Firm* — Klarquist Sparkman, LLP

(57) ABSTRACT

A method comprising co-administering to a subject having cancer, suspected of having cancer, or at risk of developing cancer:
a therapeutically effective amount of at least one compound (a) selected from (a)(i) a nitroalkene fatty acid, (a)(ii) an unsaturated fatty acid having an electron withdrawing group, a leaving group, and a carbon-carbon double bond disposed between the electron withdrawing group and the leaving group, (a)(iii) a thiolated nitro fatty acid, or (a)(iv) a dicarboxylic acid compound containing an electron withdrawing group; and
a therapeutically effective amount of at least one antineoplastic agent (b),
wherein the cancer is a cancer with hereditary etiology of defects in DNA repair genes, a cancer with a high rate of spontaneous genomic instability, a cancer that responds well to DNA damaging agent(s), or a cancer that responds well to a combination of DNA damaging agent(s) with immunotherapy.

57 Claims, 55 Drawing Sheets

(56) References Cited

U.S. PATENT DOCUMENTS

| | | | |
|---|---|---|---|
| 9,295,678 | B2 | 3/2016 | Freeman et al. |
| 9,522,156 | B2 | 12/2016 | Freeman et al. |
| 9,700,534 | B2 | 7/2017 | Freeman et al. |
| 9,750,725 | B2 | 9/2017 | Freeman et al. |
| 9,790,167 | B2 | 10/2017 | Freeman et al. |
| 9,867,795 | B2 | 1/2018 | Freeman et al. |
| 10,213,417 | B2 | 2/2019 | Freeman et al. |
| 10,258,589 | B2 | 4/2019 | Freeman et al. |
| 10,576,051 | B2 | 3/2020 | Freeman et al. |
| 10,744,106 | B2 | 8/2020 | Freeman et al. |
| 10,751,310 | B2 | 8/2020 | Freeman et al. |
| 10,765,652 | B2 | 9/2020 | Fazzari et al. |
| 10,835,518 | B2 | 11/2020 | Freeman et al. |
| 10,869,850 | B2 | 12/2020 | Freeman et al. |
| 2009/0326070 | A1* | 12/2009 | Freeman .................. A61P 7/00 554/230 |

FOREIGN PATENT DOCUMENTS

| | | |
|---|---|---|
| WO | WO 2013/116753 | 8/2013 |
| WO | WO 2016/168021 | 10/2016 |
| WO | WO 2017/151938 | 9/2017 |
| WO | WO 2018/067705 | 4/2018 |
| WO | WO 2018/067709 | 4/2018 |
| WO | WO 2020/102529 | 5/2020 |

OTHER PUBLICATIONS

International Search Report and Written Opinion issued for International Application No. PCT/US2019/061474 on Feb. 6, 2020.

Khoo et al., "Electrophilic fatty acid nitroalkenes regulate Nrf2 and NF-κB signaling: a medicinal chemistry investigation of structure-formation relationships," *Scientific Reports*, vol. 8, 16 pages, Feb. 2, 2018.

Skoko et al., "Redox regulation of RAD51 and homologous recombination by peroxiredoxin 1 and electrophilic nitro-fatty acids," *Free Rad. Biol. Med.*, vol. 112, Supplement 1, p. 100, Nov. 30, 2017.

Skoko et al., "Redox regulation of RAD51 and homologous recombination by peroxiredoxin 1 and electrophilic nitro-fatty acids," *Molecular Cell*, 65 pages, posted online Apr. 5, 2018.

Woodcock et al., "Electrophilic nitroalkenes inhibit triple negative breast cancer metastasis," Abstract only, vol. 30, Issue S1, *The FASEB Journal*, p. 714.7, Apr. 1, 2016.

Woodcock et al., "Nitro-fatty acid inhibition of triple-negative breast cancer cell viability, migration, invasion and tumor growth," *J. Biol. Chem.*, 293(4): 1120-1137, Nov. 20, 2017.

Woodcock et al., "Selective inhibition of triple negative breast cancer cell mobility and viability by nitro-oleic acid," *Free Rad. Biol. Med.*, vol. 112, Supplement 1, p. 99, Nov. 30, 2017.

Extended European Search Report issued for EPC Application No. 19885442.4 on Jul. 18, 2022.

Woodcock et al., "Nitro-fatty acid inhibition of triple-negative breast cancer cell viability, migration, invasion and tumor growth," *J. Biol. Chem.*, 293(4): 1120-1137, Jan. 2018.

Kuhn, et al., "Anti-inflammatory nitro-fatty acids suppress tumor growth by triggering mitochondrial dysfunction and activation of the intrinsic apoptotic pathway in colorectal cancer cells," *Biomedical Pharmacology*, vol. 155, pp. 48-60, 2018.

Examination Report issued in Canada Patent Application No. 3,114,406, dated Nov. 22, 2024, 8 pages.

* cited by examiner

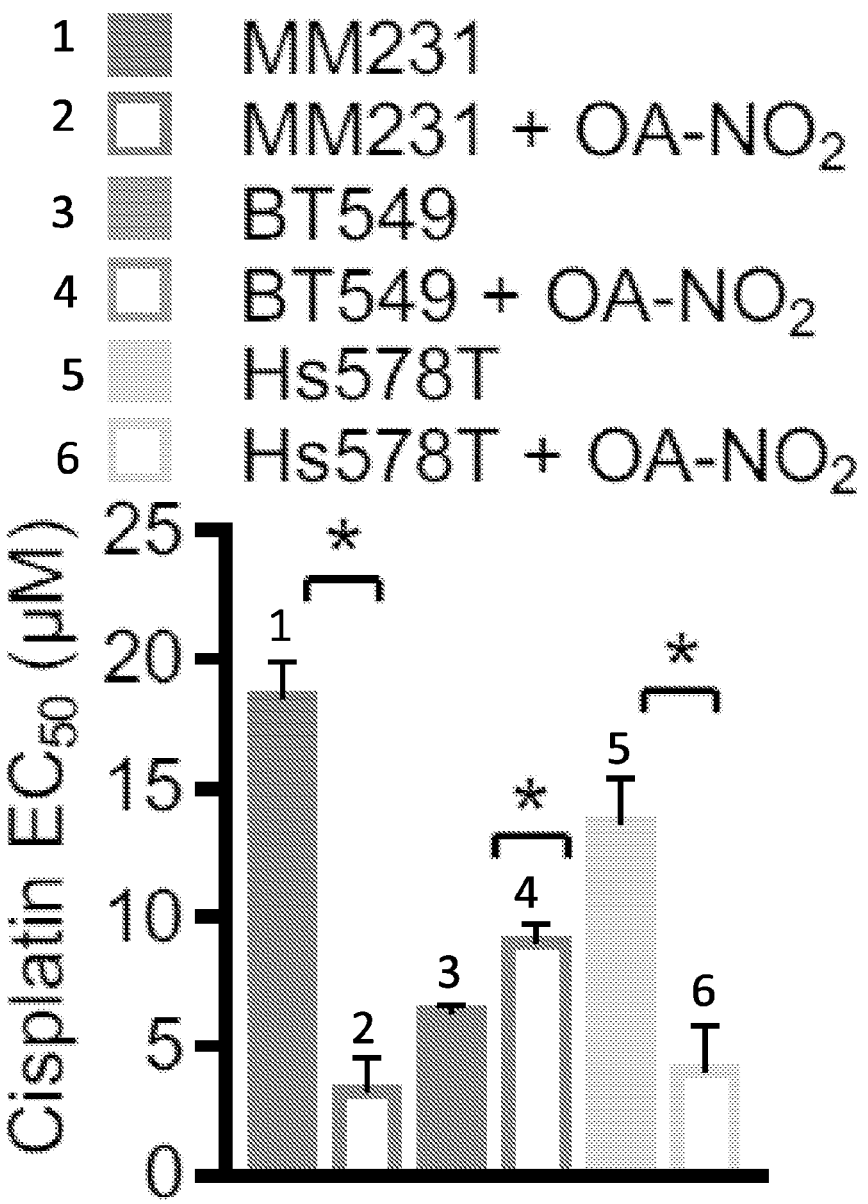

FIG. 1H
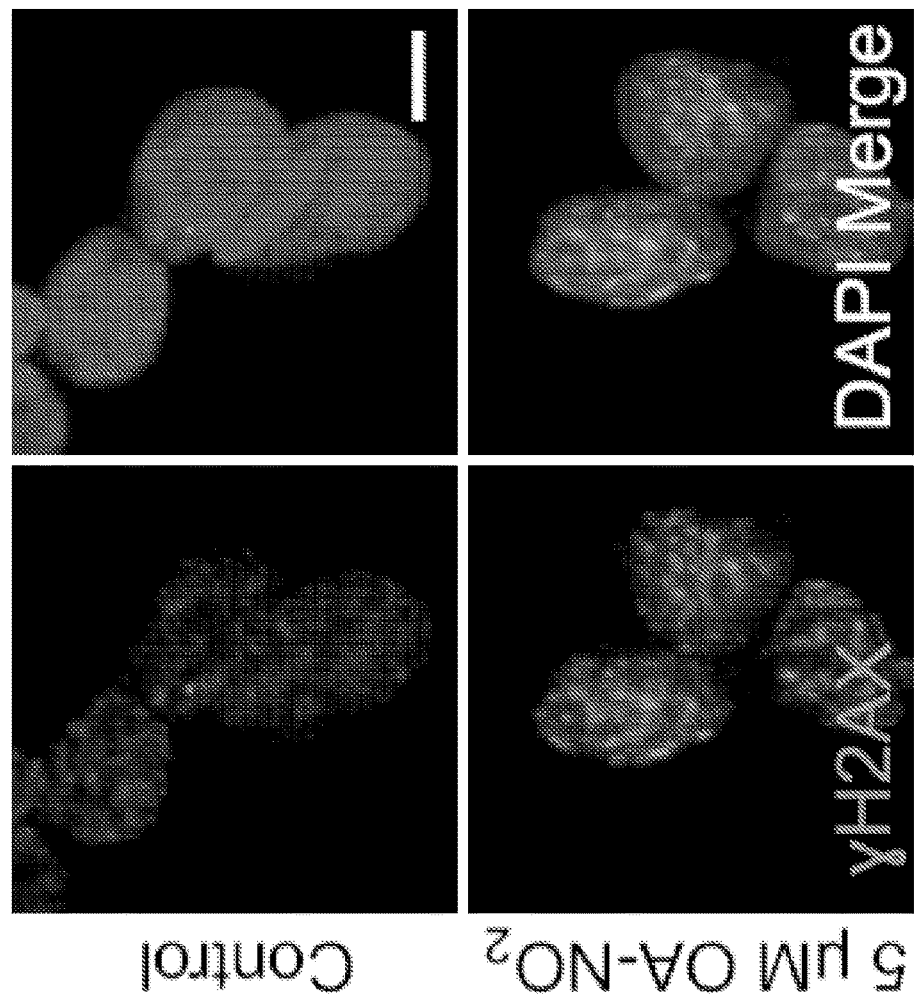
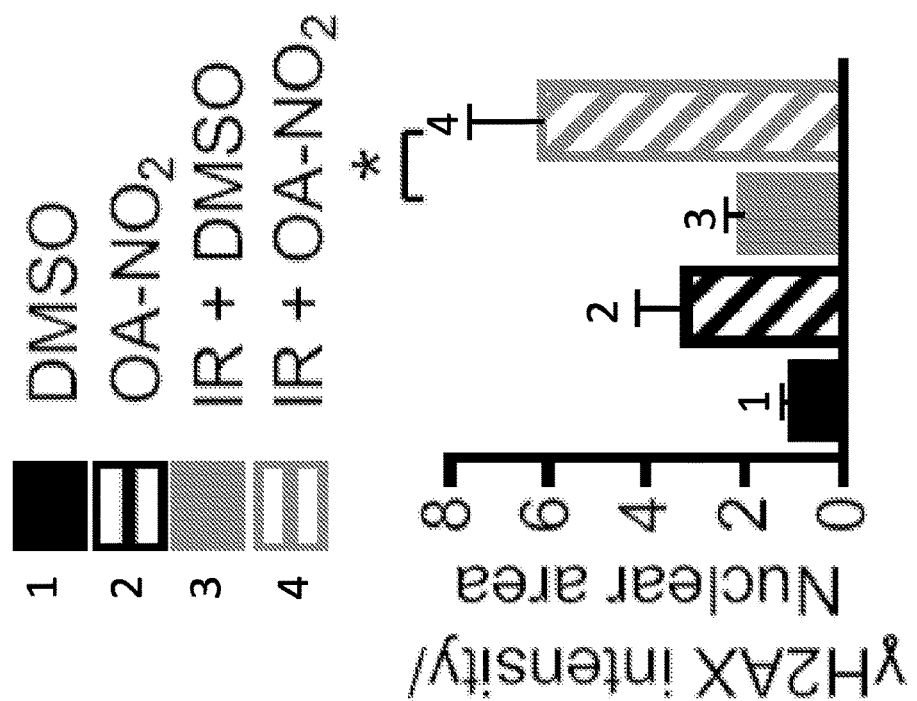

FIG. 1J

Cell growth inhibition (%)

| Tz (µM) \ NO₂-OA (µM) | 0.02 | 0.07 | 0.29 | 1.17 | 4.69 | 18.75 | 75.00 |
|---|---|---|---|---|---|---|---|
| 0.2 | 11 | 18 | 21 | 22 | 26 | 29 | 35 |
| 0.4 | 10 | 16 | 21 | 22 | 24 | 27 | 34 |
| 0.8 | 10 | 16 | 20 | 23 | 26 | 29 | 36 |
| 1.5 | 24 | 28 | 25 | 37 | 32 | 33 | 40 |
| 3.0 | 60 | 62 | 72 | 72 | 67 | 66 | 69 |
| 6.0 | 95 | 94 | 94 | 95 | 94 | 96 | 97 |
| 12.0 | 100 | 100 | 102 | 99 | 98 | 98 | 97 |

(Talazoparib rows: 75.00, 18.75, 4.69, 1.17, 0.29, 0.07, 0.02 µM; NO₂-OA columns: 12.0, 6.0, 3.0, 1.5, 0.8, 0.4, 0.2 µM)

Scale: 0 — 100

FIG. 1K

Combination index

| Tz (µM) \ NO₂-OA (µM) | 0.02 | 0.07 | 0.29 | 1.17 | 4.69 | 18.75 | 75.00 |
|---|---|---|---|---|---|---|---|
| 0.2 | 3.50 | 0.53 | 0.55 | 1.28 | 1.55 | 2.06 | 0.66 |
| 0.4 | 7.41 | 1.36 | 0.65 | 1.38 | 2.33 | 2.99 | 1.24 |
| 0.8 | 7.73 | 1.61 | 1.11 | 1.18 | 1.37 | 1.74 | 0.88 |
| 1.5 | 0.72 | 0.66 | 0.79 | 0.54 | 0.72 | 0.95 | 0.68 |
| 3.0 | 0.67 | 0.64 | 0.51 | 0.51 | 0.58 | 0.59 | 0.55 |
| 6.0 | 0.77 | 0.38 | 0.42 | 0.38 | 0.42 | 0.34 | 0.30 |
| 12.0 | 0.84 | 0.34 | 0.34 | 0.34 | 0.48 | 0.48 | 0.59 |

Scale: Synergistic 0 — 1 Additive

| Breast cancer cell lines | IC$_{50}$ value* (µM) |
| --- | --- |
| 1. MCF-10A (Non-tumorigenic) | 7.70 ± 1.93 |
| 2. MDA-MB-231 (TNBC) | 2.67 ± 0.11 |
| 3. MDA-MB-468 (TNBC) | 1.61 ± 0.11 |
| 4. MCF7 (ER+) | 11.61 ± 3.59 |

*Values are mean ± SD of three independent experiments, n=5

FIG. 5A MDA-MB-231
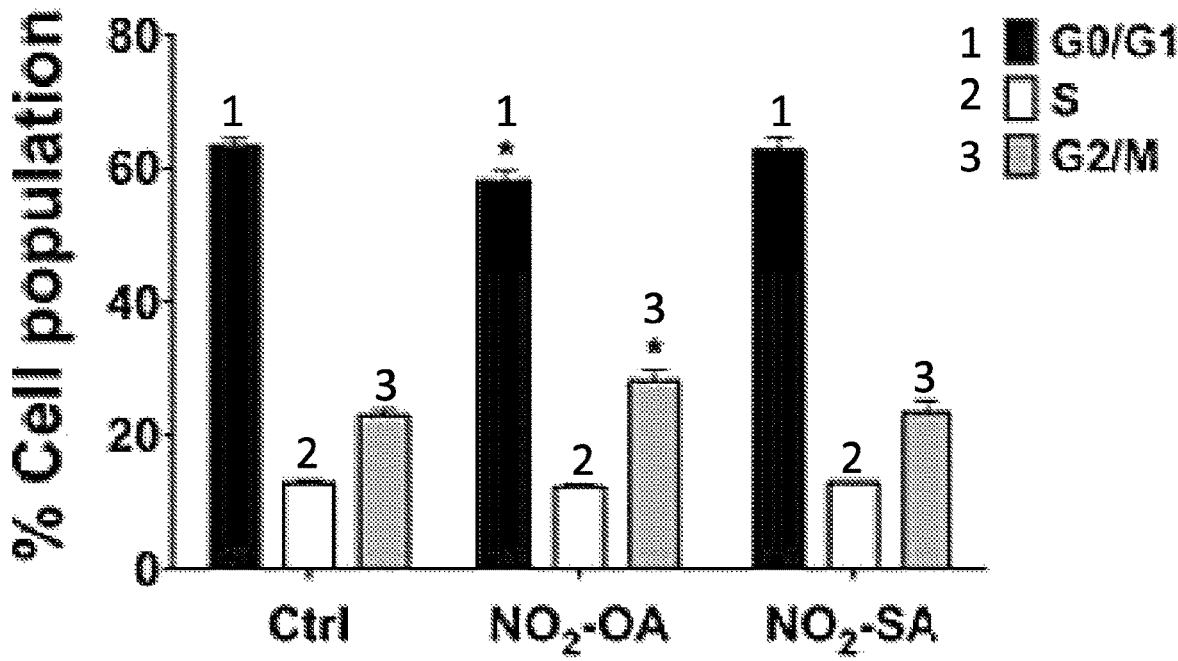
FIG. 5B MDA-MB-468
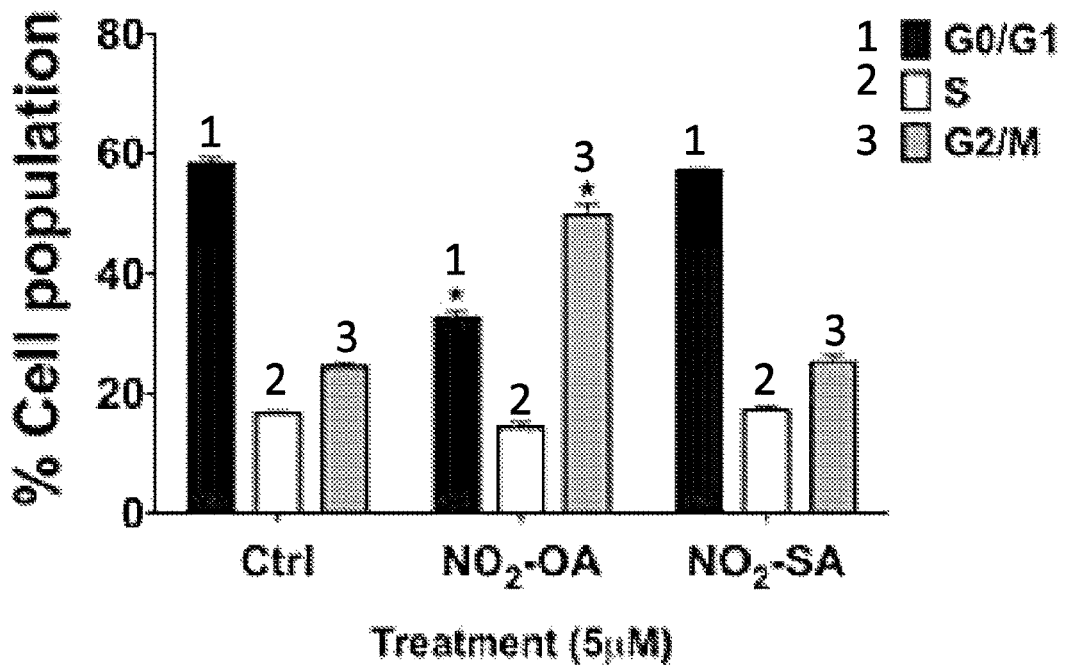

FIG. 6C
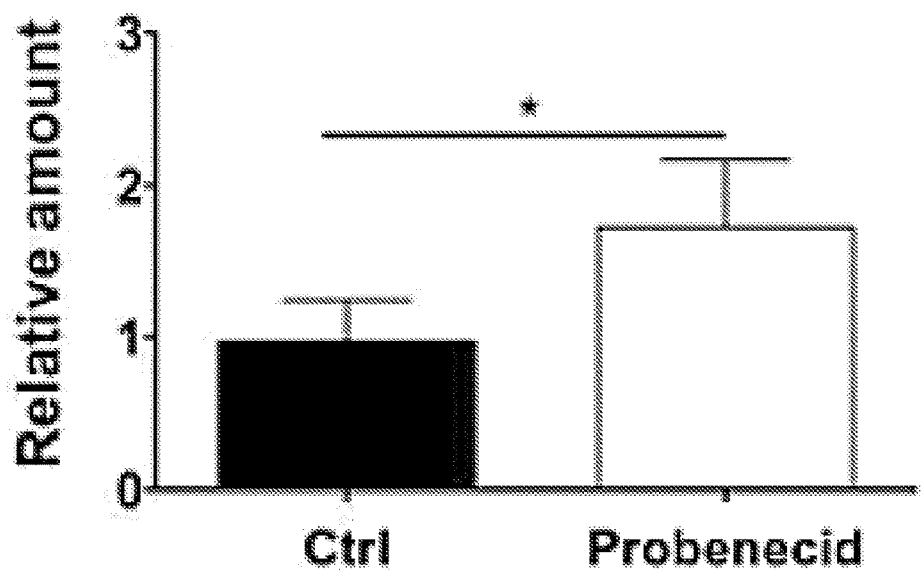
FIG. 6D
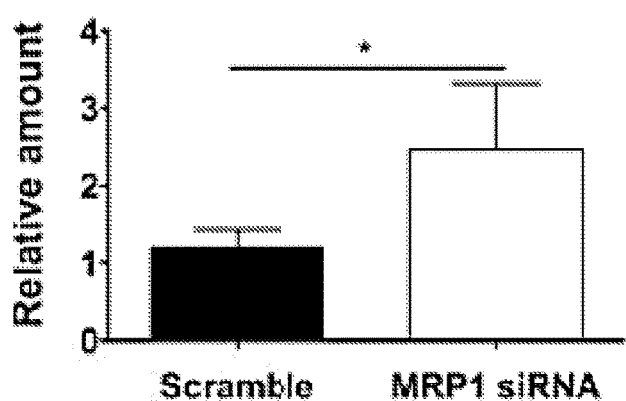
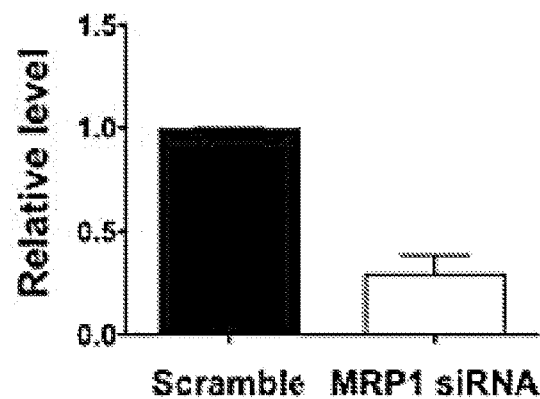

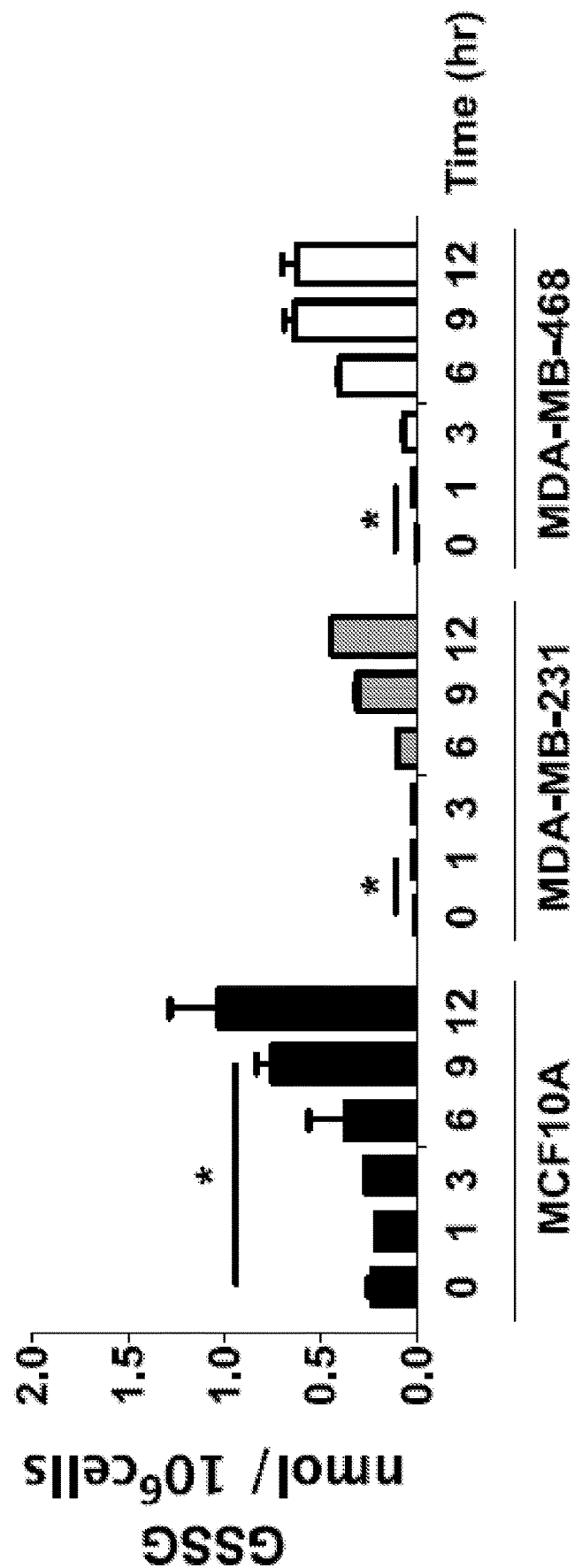

FIG. 8B  MDA-MB-231
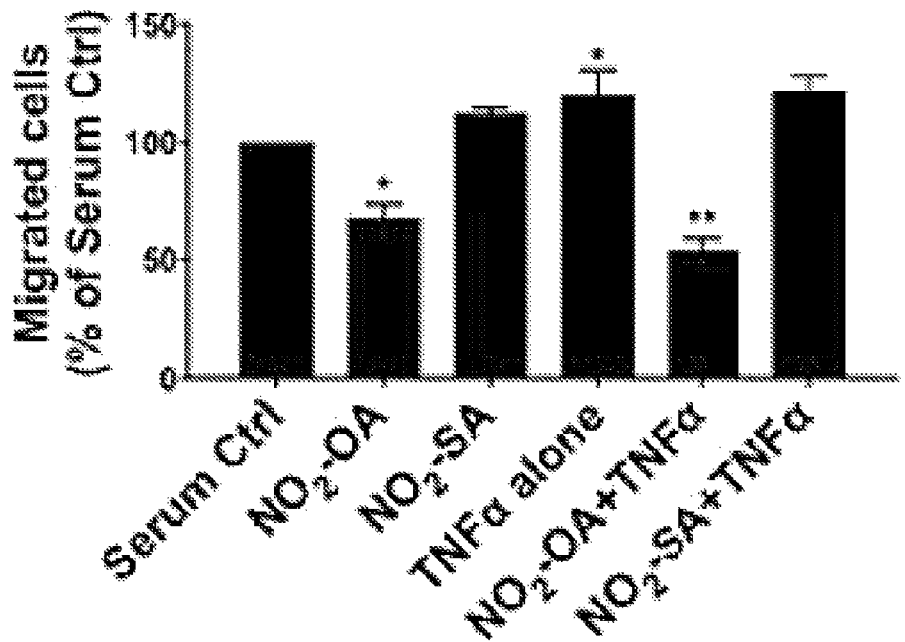
FIG. 8C  MDA-MB-468
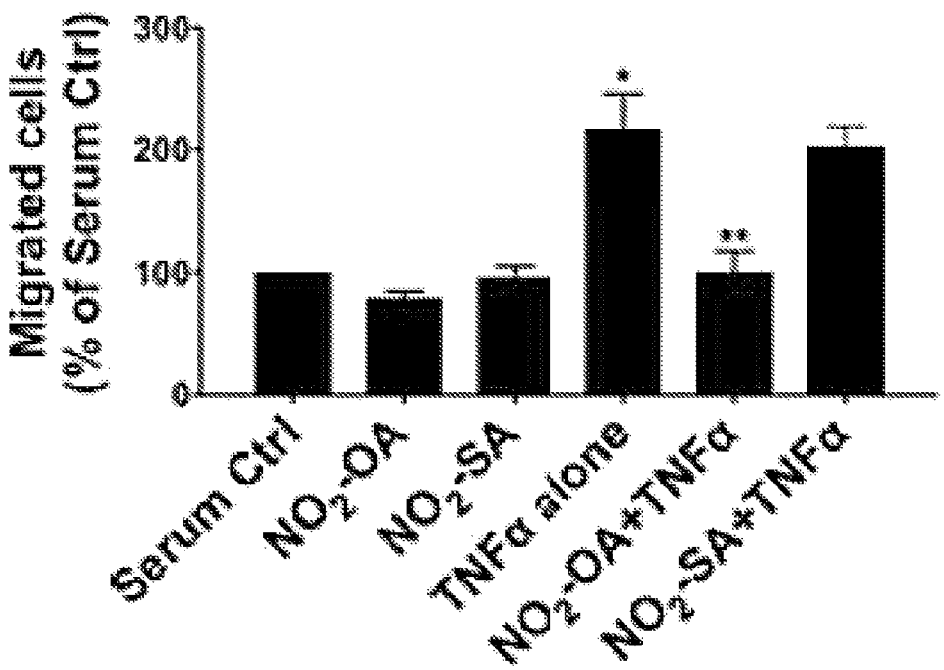

MDA-MB-468

FIG. 9F RelA mRNA
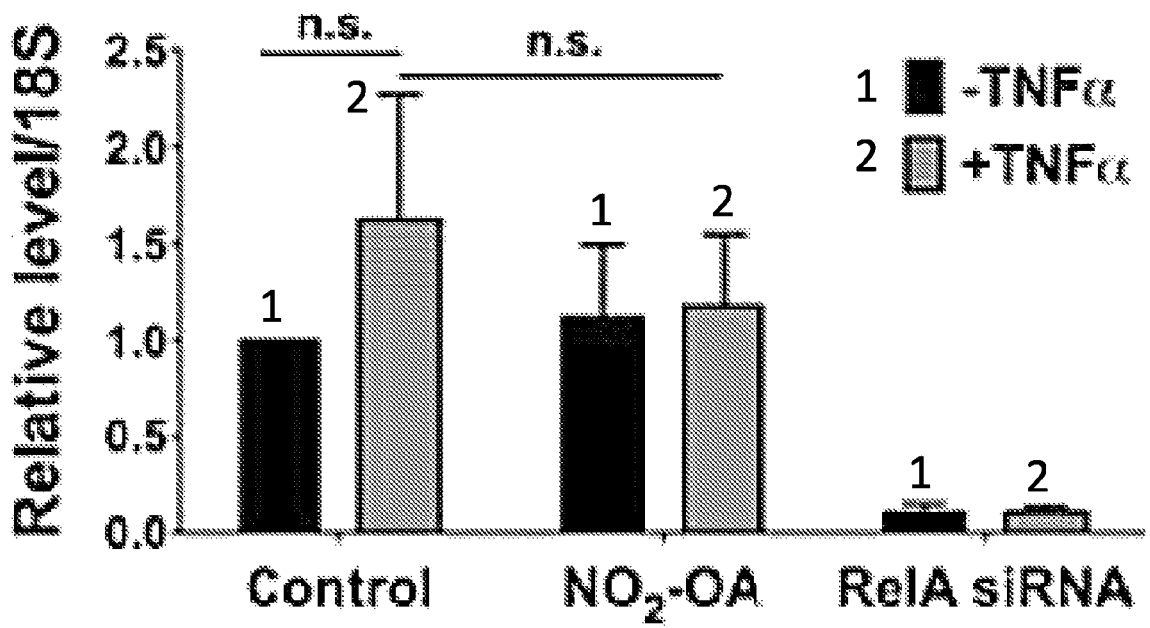
FIG. 9G ICAM-1 mRNA
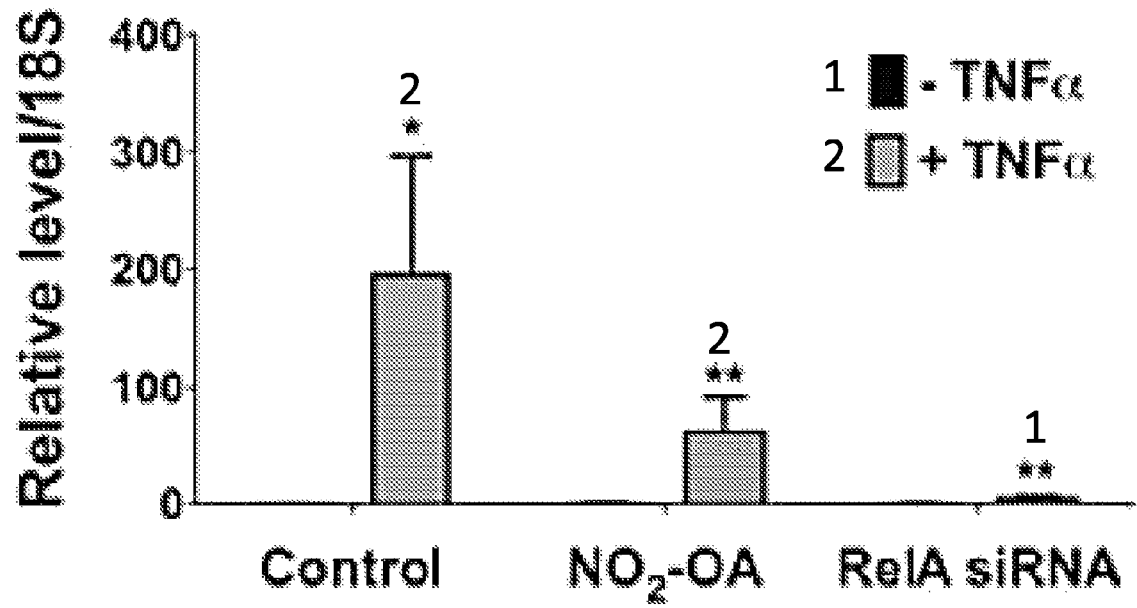

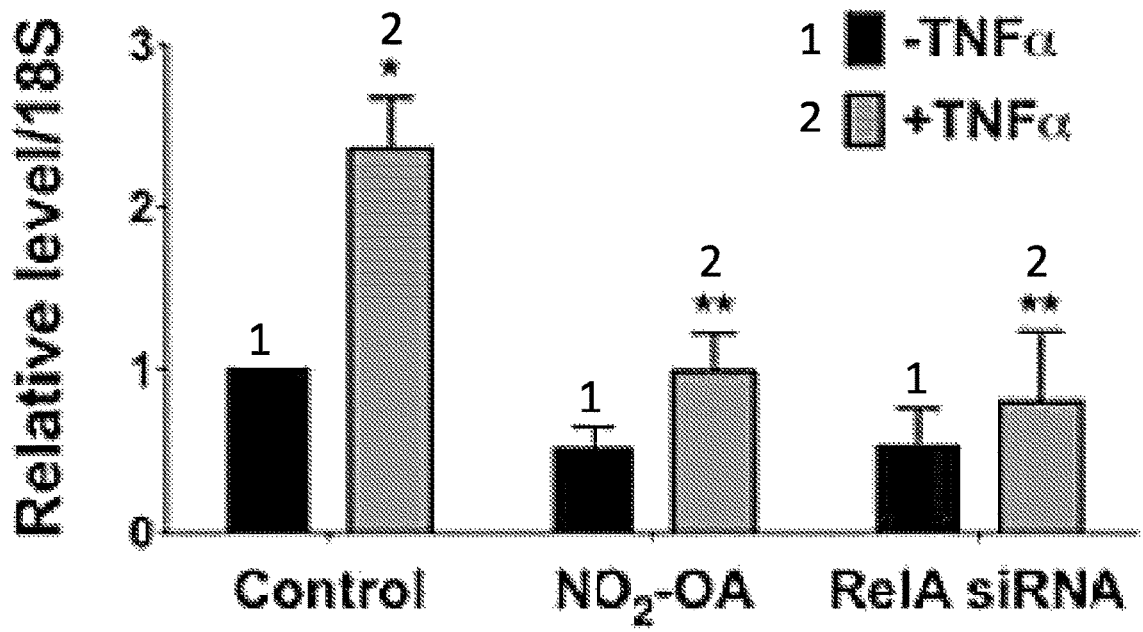
FIG. 9H  uPA mRNA
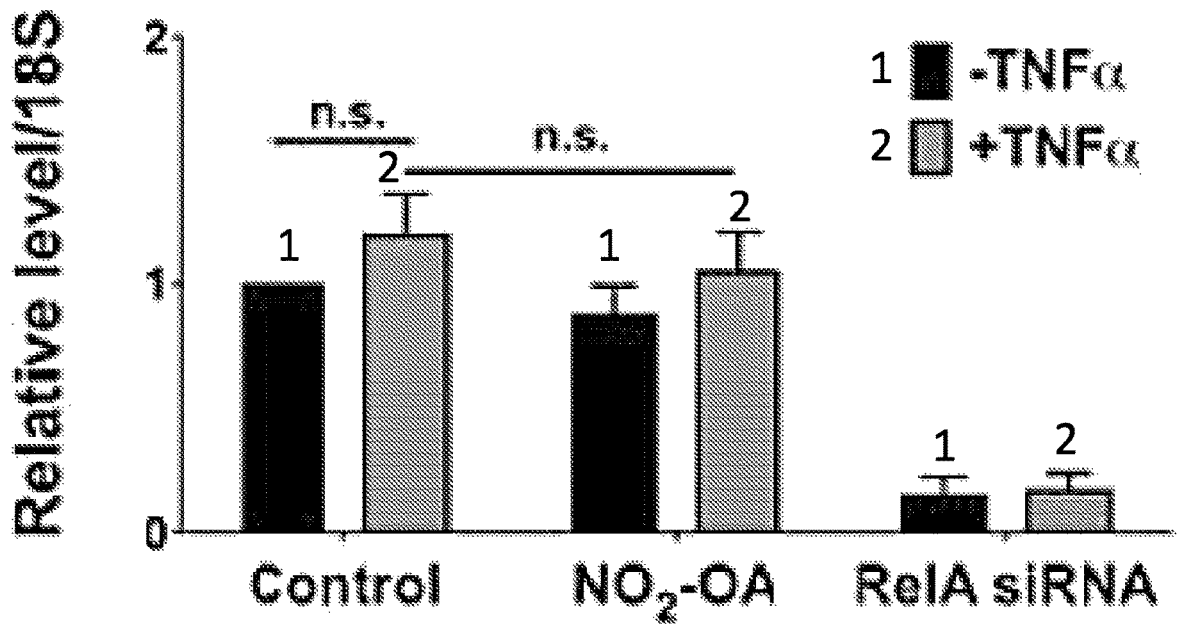
FIG. 9I  RelA mRNA

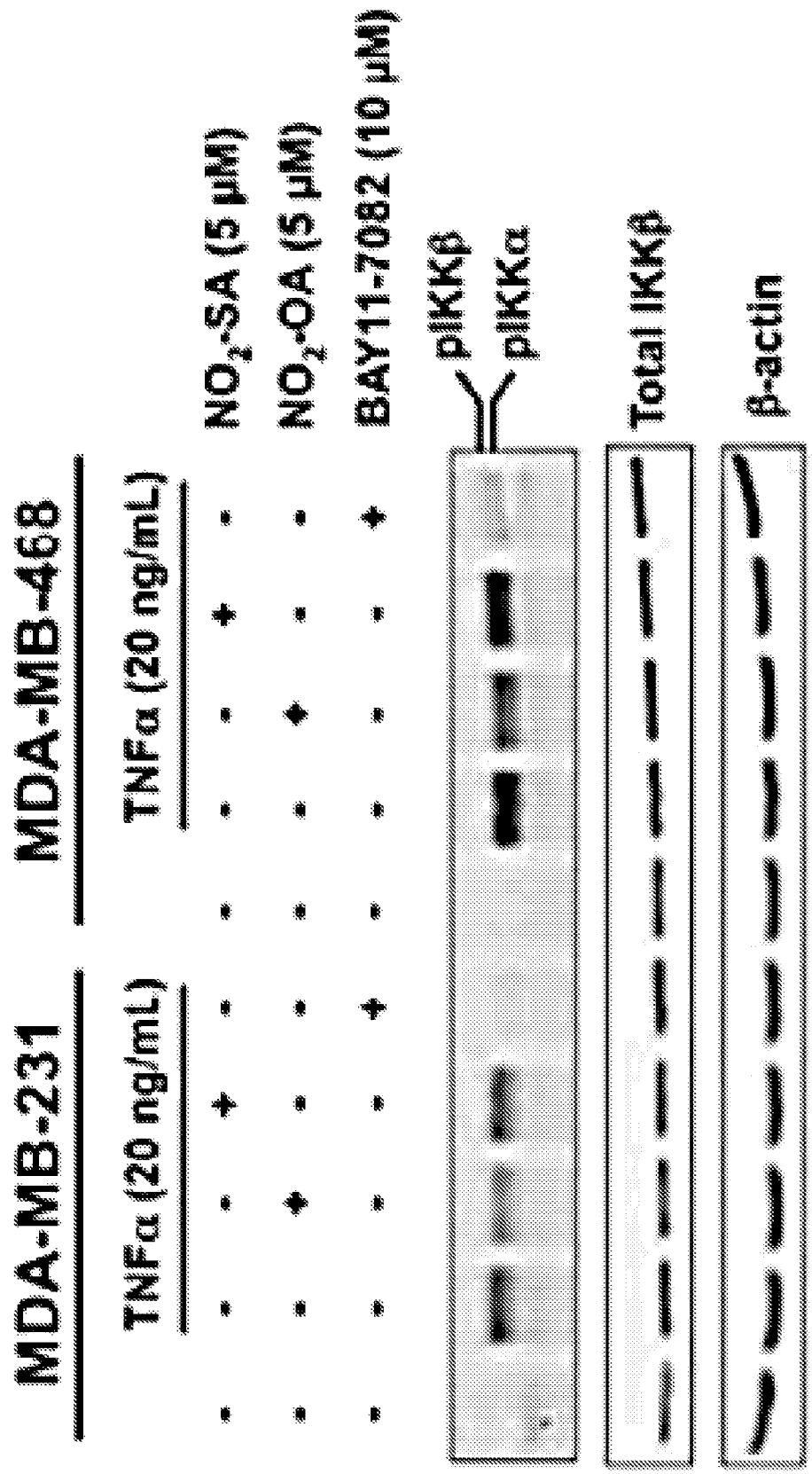

FIG. 11C

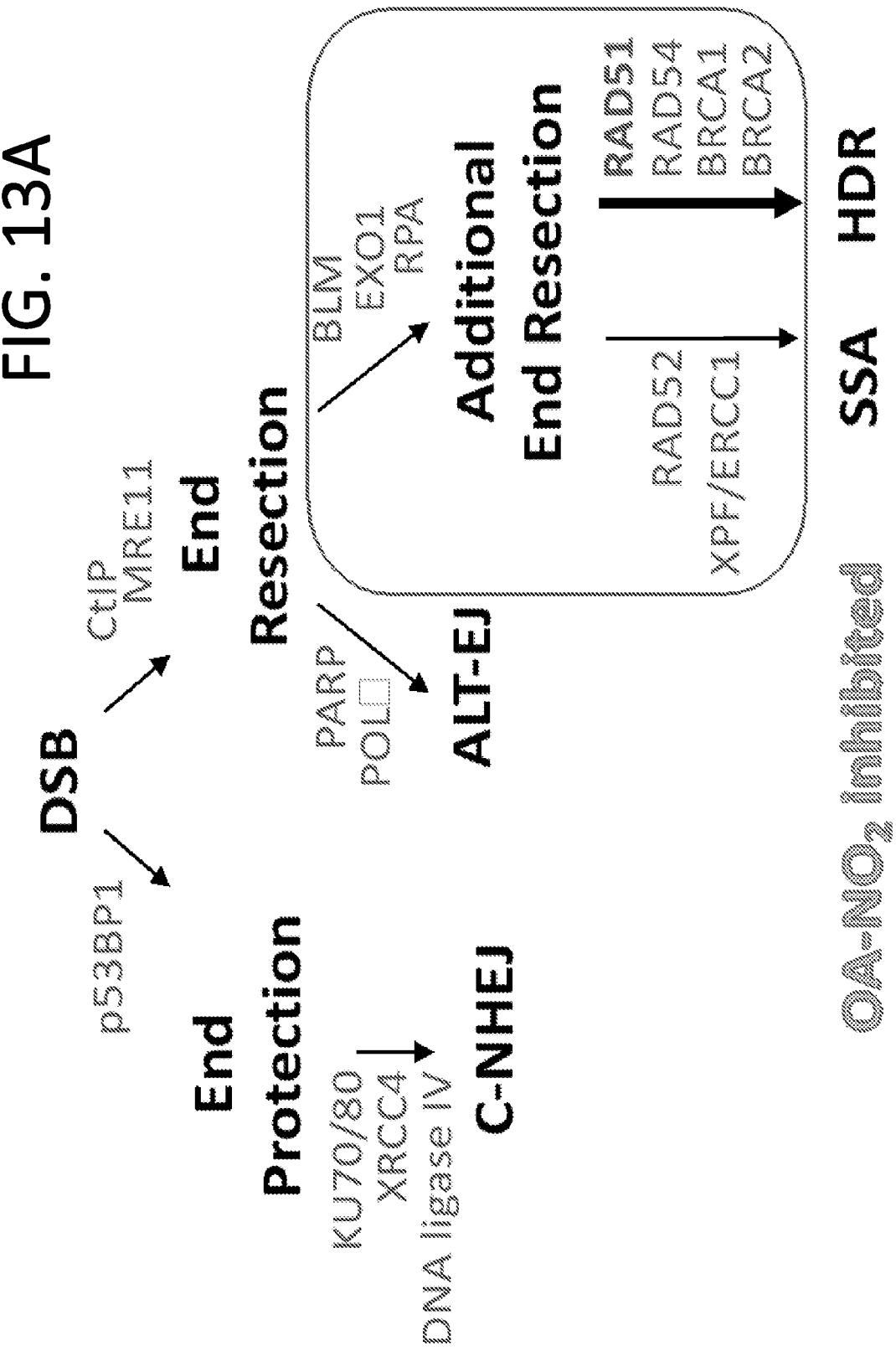

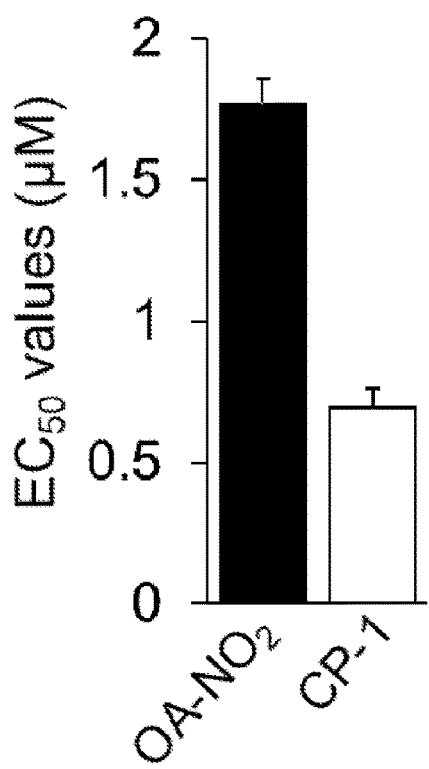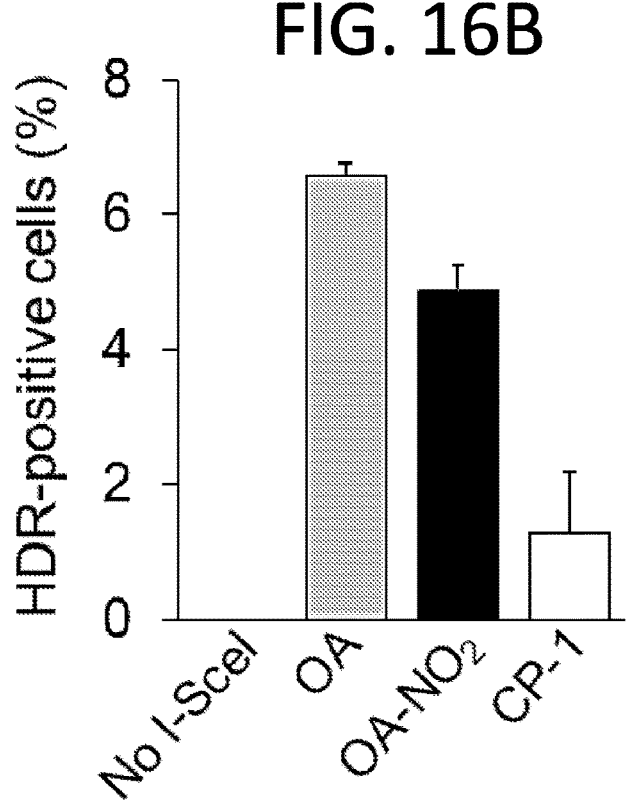

ELECTROPHILES AND ELECTROPHILE PRO-DRUGS AS RAD51 INHIBITORS

This is the U.S. National Stage of International Application No. PCT/US2019/061474, filed Nov. 14, 2019, which was published in English under PCT Article 21 (2), which application in turn claims the benefit of U.S. Provisional Application No. 62/767,424, filed Nov. 14, 2018, which is incorporated herein by reference.

ACKNOWLEDGMENT OF GOVERNMENT SUPPORT

This invention was made with government support under Grant Nos. W81XWH-19-1-0048 and W81XWH-19-1-0052 awarded by the Defense Health Agency, Medical Research and Development Branch, and HL058115, DK072506, HL103455, and HL064937 awarded by the National Institutes of Health. The government has certain rights in the invention.

BACKGROUND

Triple negative breast cancer (TNBC) comprises ~20% of all breast cancers and is the most aggressive mammary cancer subtype. Devoid of the estrogen and progesterone receptors, along with the receptor tyrosine kinase ERB2 (HER2) that define most mammary cancers, there are no targeted therapies for patients with TNBC. This, combined with a high metastatic rate and a lower 5-year survival rate than for other breast cancer phenotypes, means there is significant unmet need for new therapeutic strategies.

Fatty acid nitroalkenes are endogenously detectable products of nitric oxide and nitrite dependent metabolic and inflammatory reactions with unsaturated fatty acids. By virtue of their electrophilic nature, fatty acid nitroalkenes mediate post-translational modifications (PTM) of reactive nucleophilic cysteine thiols in proteins including p65 in NF-κB, Keap1, PPARγ, STING, 5-lipoxygenase, thus modulating protein structure and function and mediating pleiotropic cytoprotective and anti-inflammatory signaling responses.

The multitude of exogenously and endogenously-stimulated DNA-damaging events requires that DNA damage be vigilantly detected and efficiently repaired. Several DNA repair mechanisms have been identified that ameliorate deleterious genomic perturbations such as direct reversal, mismatch repair, nucleotide excision repair, base excision repair and double-stranded break (DSB) repair. DNA DSBs are particularly pathogenic, as the loss of genomic material and mutations promote genomic variability and disequilibrium.

DNA DSB repair consists of four pathways: canonical non-homologous end joining (c-NHEJ), alternative enjoining (ALT-EJ), single strand annealing (SSA) and homologous recombination-directed repair (HDR). While NHEJ does not require homology (homologous sequence) to bridge the DSB prior to ligation, ALT-EJ is mediated by short stretches of homology to bridge DSB prior to ligation. SSA uses flanking homology to bridge the DNA lesion, causing a deletion between repeats. HDR is the major event of DSB repair that involves invasion of a homologous template by at least one strand from the DSB, which templates nascent DNA synthesis to form an extended strand that can form a bridge to the other DSB end. The homologous strand invasion step is catalyzed by the recombinase Rad51. End resection is the processing of chromosomal DSBs to generate 3' single strand DNA. Each of these pathways involves a specific set of DNA repair proteins (FIG. 14A).

There are two main pathways to repair DSBs: non-homologous end joining (NHEJ) and homologous recombination (HR). While NHEJ is faster and more frequently used, HR repair mechanisms maintain the highest fidelity of the genome. HR repair protects cells from the deleterious genomic instability caused by DSB by correcting for genetic material loss through homologous template searches that maintain the genomic landscape. RAD51 is a critical component of HR, which facilitates the homology search and strand-exchange to repair DSBs. RAD51 and the structurally similar proteins XRCC2, XRCC3, RAD51B, RAD51C, RAD51D, DMC1 and SWSAP1 all work in concert to promote HR. Consequently, reductions in RAD51 and paralog activity are linked with carcinogenesis. While RAD51 is essential for high fidelity repair of DSB to maintain genomic homeostasis, overexpression of RAD51 in cancer can also have detrimental consequences. Extents of RAD51 overexpression are correlated with breast cancer tumor grade and has been identified in triple negative breast cancer (TNBC) cell lines and metastatic patient samples. Overexpression of RAD51 inhibits chemotherapeutic efficacy in cancer patients by rendering cancer cells more resistant to DNA damaging agents. Responses to neoadjuvant chemotherapy are inversely correlated with BRCA1-, γH2AX- and RAD51-foci before treatment as well as RAD51-foci numbers following treatment.

SUMMARY

Disclosed herein are methods comprising co-administering to a subject having cancer, suspected of having cancer, at risk of developing cancer, or in cancer remission:

a therapeutically effective amount of at least one compound (a) selected from (a)(i) a nitroalkene fatty acid, (a)(ii) an unsaturated fatty acid having an electron withdrawing group, a leaving group, and a carbon-carbon double bond disposed between the electron withdrawing group and the leaving group, (a)(iii) a thiolated nitro fatty acid, or (a)(iv) a dicarboxylic acid compound containing an electron withdrawing group; and a therapeutically effective amount of at least one antineoplastic agent (b), wherein the cancer is a cancer with hereditary etiology of defects in DNA repair genes, a cancer with a high rate of spontaneous genomic instability, a cancer that is treated with DNA damaging agent(s), or a cancer that is treated with a combination of DNA damaging agent(s) with immunotherapy.

Illustrative cancers include breast, particularly triple negative breast cancer, colon, prostate, ovarian, brain cancer (glioblastoma), pancreatic, skin cancer (such as melanoma). Cancer cells that acquired the capability to spread (metastasize) and are highly genomically unstable are particularly amenable to the combination treatments disclosed herein.

Also disclosed herein are methods comprising administering to a subject having triple negative cancer, suspected of having triple negative breast cancer, or at risk of developing triple negative breast cancer a therapeutically effective amount of at least one compound (a) selected from (a)(i) a nitroalkene fatty acid, (a)(ii) an unsaturated fatty acid having an electron withdrawing group, a leaving group, and a carbon-carbon double bond disposed between the electron withdrawing group and the leaving group, (a)(iii) a thiolated nitro fatty acid, or (a)(iv) a dicarboxylic acid compound containing an electron withdrawing group.

Further disclosed herein is a pharmaceutical composition comprising a therapeutically effective amount of at least one compound (a) selected from (a)(i) a nitroalkene fatty acid, (a)(ii) an unsaturated fatty acid having an electron withdrawing group, a leaving group, and a carbon-carbon double bond disposed between the electron withdrawing group and the leaving group, (a)(iii) a thiolated nitro fatty acid, or (a)(iv) a dicarboxylic acid compound containing an electron withdrawing group; and a therapeutically effective amount of at least one antineoplastic agent (b).

The foregoing will become more apparent from the following detailed description, which proceeds with reference to the accompanying figures.

BRIEF DESCRIPTION OF THE DRAWINGS

FIGS. 1A-1K. $NO_2$-OA (10-nitro-octadec-9-enoic acid) inhibits TNBC cell growth, RAD51 foci formation and sensitivity to ionizing radiation. FIG. 1A. MDA-MB-231 (MM231) cells (0.5×106) were orthotopically injected into 6 week-old mice and gavaged with 15 mg/kg oleic acid (OA) (black) or $NO_2$-OA (red) for 4 w when tumors reached a volume of 100 mm3 FIG. 1B. Tumoral γH2AX expression was increased in $NO_2$-OA treated mice compared to OA control mice by immunoblot (n=6-7 per group). FIG. 1C. MM231 (red), BT549 (blue) or HS578T (green) cells were treated with increasing concentrations of $NO_2$-OA and relative growth was measured by quantifying luminescent ATP levels (CellTiter-Glo). EC50 values indicate average+SEM, n=3. FIGS. 1D-1F. MM231 (red), BT549 (blue) or HS578T (green) cells were treated with increasing concentrations of doxorubicin, cisplatin or olaparib±$NO_2$-OA and measured as above. FIG. 1G. MM231 (red) cells were treated with increasing concentrations of olaparib daily+vehicle, OA or $NO_2$-OA and measured as above. FIGS. 1H-1I. $NO_2$-OA diminished RAD51 foci formation (green) and increased γH2AX (red) in MM231 cells following irradiation with 5 Gy. Merged samples include DAPI stained nuclei (blue). Cells on 16-well coverslips were dosed with 5 Gy then and treated with 5 µM $NO_2$-OA or vehicle for 6 h prior to IF processing. The average percentages of cells with 5 or more foci from confocal z-stacked images are indicated from 0 or 5 Gy samples+SEM. FIG. 1J. $NO_2$-OA reduces Rad51 foci in the TNBC cell line MDA-MB-231, it has no effect on irradiated benign breast epithelial cells (MCF-10A) due to the distinctly different metabolism and PK of $NO_2$-OA in non-tumorigenic breast ductal epithelial cells as opposed to TNBC cells. Rad51 foci were counted and γH2AX intensities were assessed by ImageJ in 5Gy irradiated cells (histograms), that were analyzed by immunofluorescence (IF). FIG. 1K, upper part. $NO_2$-OA shows a lower $IC_{50}$ compared to $NO_2$-OA and better combination indices when combined with talazoparib. Growth inhibition (relative to cell numbers) of MDA-MB-231 cells treated with talazoparib (0.01-75 µM) plus $NO_2$-OA (0.2-12 µM) daily for three days, was determined by luminescent detection of ATP (CellTite-Glo). FIG. 1K, lower part. Combination index (CI) was calculated by the Chou-Talalay method. CI<1 is synergistic. Data represent the mean from three independent experiments.

FIGS. 2A-2B. U2OS cells containing the HR reporter construct DR-GFP were transfected with an I-SceI plasmid and treated with vehicle (gray), 5 µM OA (green) or 5 µM $NO_2$-OA (red). Negative control cells did not have I-SceI present. Average+SEM, n≥3. FIG. 2A. The number of GFP positive cells were detected by flow cytometry at 48 h. FIG. 2B. Emergence of GFP positive cells over 68 h was quantified using live-cell fluorescent microscopy. GFP positive cell counts were normalized to cell confluency and compared. FIGS. 2C-2D. U2OS cells containing the NHEJ reporter construct EJ5-GFP were transfected with an I-SceI plasmid and treated with vehicle (gray), 5 µM OA (green) or 5 µM $NO_2$-OA (red). Negative control cells did not have I-SceI present. Average+SEM, n=3. FIG. 2C. The number of GFP positive cells were detected by flow cytometry at 48 h. FIG. 2D. Emergence of GFP positive cells over 68 h was quantified using live-cell fluorescent microscopy. GFP positive cell counts were normalized to cell confluency and compared.

FIG. 3A. U2OS cells containing the HR reporter construct DR-GFP were stably transfected with a control or RAD51 overexpression plasmid and the cells were investigated as above with 5 µM $NO_2$-OA in control (red) or RAD51 overexpressing cells (red striped). FIG. 3B. $NO_2$-OA binds RAD51 in vitro. Purified RAD51 protein was incubated with control, biotinylated OA, $NO_2$-OA or nitrated stearic acid $NO_2$—SA for 1 h and precipitated with streptavidin coated agarose and then detected by immunoblot. FIG. 3C. $NO_2$-OA covalently reacts with RAD51 Cys319 in cells expressing RAD51. 293T cells expressing WT or cysteine mutant RAD51 were incubated with biotinylated $NO_2$-OA for 1 h and precipitated and detected. Three independent experiments were quantified and analyzed by one-way ANOVA * p<0.05. FIG. 3D. Alexa Fluor 488 conjugated DNA was incubated with purified RAD51, ATP and 5 µM OA (black), 5 µM $NO_2$-OA (gray) or 10 µM $NO_2$-OA (white) and fluorescence polarization was quantified and normalized to a control lacking ATP. FIG. 3E. Molecular modeling of RAD51 (blue) and $NO_2$-OA (purple). Covalent binding of $NO_2$-OA with the Cys319 residue (gold) of RAD51 is predicted to be further stabilized by hydrophobic interactions with Pro318 and possible hydrogen bonding with Glu322 of RAD51. FIG. 3F. $NO_2$-OA disrupts ABL binding to RAD51 in vitro. Purified RAD51 and ABL core proteins were incubated with OA-$NO_2$ at 0, 100 or 500 nM for 1 h and ABL was precipitated. The amount of bound RAD51 was detected by immunoblot. FIG. 3G. $NO_2$-OA disrupts RAD51 and ABL interactions as assessed by immunoprecipitation assays (IP) and reduces RAD51 Y315 phosphorylation. 293T cells were transfected with FLAG-RAD51 and ABL core protein and then treated with $NO_2$-OA for 1 h. RAD51 interactions with ABL and phosphorylated RAD51 Y315 were probed by IP and immunoblot. FIG. 3H. $NO_2$-OA binds RAD51 in MM231 or MM468 cells. Cells were incubated with biotinylated $NO_2$-OA and then lysates were precipitated with streptavidin coated agarose and detected by immunoblot. FIG. 3I. $NO_2$-OA impairs HR by inhibiting RAD51 filament formation to cause genomic instability and death in TNBC cells.

(FIG. 4A) Chemical structures of nitro-oleic acid ($NO_2$-OA; 10-nitro-octadec-9-enoic acid) and the non-electrophilic 10-nitro stearic acid ($NO_2$—SA; 10-nitro-octadecanoic acid), and oleic acid (OA; octadec-9-enoic acid). * indicates the electrophilic carbon. (FIGS. 4B-4D). The effect of $NO_2$-OA on the growth of MDA-MB-231, MDA-MB-468, and MCF7 compared to MCF-10A cells. Data are shown as percent of untreated control cells (mean±SD). * p<0.05 indicates significant difference between two cell types within each treatment. Three independent experiments were performed (n=5 each). (FIG. 4E)

The IC$_{50}$ values of NO$_2$-OA in each breast cancer cell line. (FIG. 4F) The effect of NO$_2$-OA (7.5 mg/kg daily) on MDA-MB-231 xenograft tumor growth (mean±SEM). *, p<0.05 versus vehicle group within treatment time. Significance was determined by two-way analysis of variance followed by Tukey's post hoc test.

FIGS. 5A-5F. NO$_2$-OA promotes cell cycle arrest and apoptosis in TNBC cells. Percentages of the cell population in each phase of the cell cycle (G0/G1, S, and G2/M) are shown for (FIG. 5A) MDA-MB-231, (FIG. 5B) MDA-MB-468, and (FIG. 5C) MCF-10A cells treated with NO$_2$-OA (5 µM) for 24 hr. Cells were harvested and analyzed by fluorescence-activated cell sorting. Significance was determined by one-way analysis of variance followed by Tukey post-hoc test. Data are mean±SD. n=3. *, p<0.05 versus control. (FIG. 5D) Immunoblot analysis of cyclin D1 and p21 in MCF-10A, MDA-MB-231, and MDA-MB-468 cells that were treated with OA (7.5 µM), NO$_2$—SA (7.5 µM) or NO$_2$-OA (5 µM) for 24 hr. (FIG. 5E) Immunoblot analysis of PARP-1 cleavage in MCF-10A, MDA-MB-231, and MDA-MB-468 cells treated with OA (7.5 µM), NO$_2$-SA (7.5 µM) or NO$_2$-OA (5 µM) for 24 hr. (FIG. 5F) Immunoblot analysis of caspase-8 and caspase-9 cleavage in MDA-MB-231 and MDA-MB-468 cells treated with or without NO$_2$-OA (5 µM) for 24 hr. β-actin was used as loading control. Data in FIGS. 5D-5F are representative of 3 independent experiments.

FIGS. 6A-6H. Multi-drug resistance protein-1 (MRP1) influences NO$_2$-OA trafficking and signaling in TNBC cells. (FIG. 6A) The export of NO$_2$-OA-SG by MCF-10A, MDA-MB-231, and MDA-MB-468 cells was measured by LC-MS/MS analysis. The relative extents of NO$_2$-OA-SG export is reported as a ratio of NO$_2$-OA-SG to an externally-added $^{15}$NO$_2$-d4-OA-SG standard. * p<0.05 versus MCF-10A, n=(Mann-Whitney U test). (FIG. 6B) Representative immunoblot of endogenous MRP1 protein expression in MCF-10A, MDA-MB-231, and MDA-MB-468 cells. (FIG. 6C) Suppression of MRP1 activity and (FIG. 6D) MRP1 expression increased in intracellular NO$_2$-OA-SG adduct concentrations in MCF-10A cells. The relative amount represents the relative abundance of NO$_2$-OA-SG to $^{15}$NO$_2$-d4-OA-SG standard, normalized to protein concentrations from each NO$_2$—OA-treated sample divided by the abundance of Ctrl or scramble sample. * p<0.05 versus Ctrl (n=6) or scramble (n=9) was determined by Mann-Whitney U test. The siRNA-knock-down efficiency of MRP1 was evaluated by q-RT-PCR, n=4. (FIG. 6E) The effect of probenecid on NO$_2$-OA growth inhibition of MCF-10A cells. Cells were pretreated with or without probenecid (0.25 mM) for 1 hr, and then combined with 0-25 µM NO$_2$-OA for 48 hr. FluoReporter dsDNA stain assay was performed to measure cell numbers. Data are shown as percent of untreated control cells(n=3), *, p<0.05, n=3 (unpaired Student's t test). (FIG. 6G) Immunoblot analysis of cyclin D1 and p21 in MCF-10A cells treated with NO$_2$-OA (5 µM) in the presence or absence of probenecid (1 mM used for this 24 hr incubations. (FIG. 6H) Immunoblot analysis of caspase-3 and PARP-1 cleavage in MCF-10A cells treated with NO$_2$-OA (5 µM) in the presence or absence of probenecid (1 mM) for 24 hr. The full-length (FL) and cleaved (C) forms of PARP-1 and pro-caspase-3 protein level are shown. All data are mean±SD. All immunoblots are representative of three independent experiments.

FIGS. 7A-7B. NO$_2$-OA depletes GSH levels and enhances GSSG formation in TNBC cells. The response of cellular (FIG. 7A) GSH and (FIG. 7B) GSSG to NO$_2$-OA in MCF-10A (black bars), MDA-MB-231 (grey bars), and MDA-MB-468 (white bars) cells is shown. Cells were treated with NO$_2$-OA (5 µM) for the indicated times (hr). GSH and GSSG were extracted from cells (3×10$^6$ cells/ml) and quantitated by LC-MS/MS. * p<0.05 versus 0 hr via unpaired two-tailed Student's t-test. Data are presented as mean±SD, n=5.

FIGS. 8A-8D. NO$_2$-OA inhibits TNFα-induced TNBC cell migration and invasion. (FIG. 8A) Experimental schemes and representative images of crystal violet-stained migrating MDA-MB-231 or MDA-MB-468 cells. Cells (1×10$^5$) were placed in the upper chamber with serum-free media containing the indicated treatment conditions. Migrating cells were photographed using a light microscope at 100×. (FIGS. 8B and 8C) Quantitation of migrated cells from FIG. 4A was performed by solubilization of crystal violet and spectrophotometric analysis at A573 nm. The percent migrating cells in each treatment group was compared with numbers of migrating cells in the absence of TNFα stimulation (Serum Ctrl). *, p<0.05 versus Serum Ctrl; **, p<0.05 versus TNFα alone. (FIG. 8D) To test the impact of NO$_2$-OA on TNBC cell invasion, MDA-MB-468 cells were incubated in serum-free media containing ng/mL TNFα cell migration through the Matrigel matrix towards a 5% FBS chemoattractant for 24 hr. The percent invading cells in each treatment was relative to Serum Ctrl. * p<0.05 versus TNFα alone n.s., not significant. Significance was determined by one-way analysis of variance followed by Tukey post hoc test. All data are mean±SD.

FIGS. 9A-9I. NO$_2$-OA inhibits TNFα-induced NF-κB transcriptional activity in TNBC cells. The effect of NO$_2$-OA on TNFα-induced activation of NF-κB-dependent reporter gene transcription was measured in NF-κB-luciferase reporter-transfected (FIG. 9A) MDA-MB-231 or (FIG. 9B) MDA-MB-468 cells. *, p<0.05 versus TNFα alone. (n=3) Significance was determined by Kruskal-Wallis test followed by Dunn's post test with Bonferroni corrections for multiple comparisons. (FIG. 9C) Determination of NF-κB target genes down-regulated by NO$_2$-OA in MDA-MB-468 cells using a human NF-κB target PCR array. Histograms represent the fraction of mRNA expression in NO$_2$-OA-treated versus untreated cells. GAPDH was used an internal control (black bar). The effect of NO$_2$-OA on expression of (FIG. 9D) ICAM-1, (FIG. 9E) uPA or (FIG. 9F) RelA genes in TNFα-induced MDA-MB-231 cells. Similarly, the effect of NO$_2$-OA on expression of (FIG. 9G) ICAM-1, (FIG. 9H) uPA or (FIG. 9I) RelA genes in TNFα-induced MDA-MB-468 cells. The fold increase relative to untreated controls is presented. *, p<0.05 versus untreated control, **, p<0.05 versus TNFα alone. n.s., not significant. Significance was determined by one-way analysis of variance followed by Tukey post test. All data are presented as mean±SD, n=5.

FIGS. 10A-10F. NO$_2$-OA inhibits TNFα-induced IKKβ phosphorylation and IκBα degradation, and covalently adducts IKKβ. MDA-MB-231 and MDA-MB-468 cells were used in all studies. (FIG. 10A) Representative immunoblot of IKKβ (Ser 180) phosphorylation, total IKKβ levels and relative phosphorylated IKKβ levels. Then, all phosphorylated IKKβ levels normalized to total IKKβ were quantified. (FIG. 10B) Representative immunoblot of IκBα protein levels is shown and the relative total IκBα levels (normalized to total β-actin) are quantified in response to NO$_2$-SA, NO$_2$-OA and the NF-kB inhibitor BAY11-7082. (FIG. 10C) Representative immunoblot of IκBα (Ser 32) phosphorylation and total IκBα are shown in response to NO$_2$—SA, NO$_2$-OA and the NFkB inhibitor BAY11-7082. (FIGS. 10D-10F) NO$_2$-OA alkylates TNBC IKKβ protein. Biotinylated NO$_2$-OA, NO$_2$—SA and OA and adducted proteins were affinity purified by streptavidin agarose beads from cell lysates. Pulled-down IKKβ protein was then detected by immunoblotting. IKKβ and control β-actin immunoblots from the same input lysates used for affinity purification are shown below the panel. *$p<0.05$ versus TNFα alone. n.s., not significant. Significance was determined by one-way analysis of variance followed by Tukey Post test.

FIGS. 11A-11C. $NO_2$-OA alkylates and destabilizes NF-κB RelA protein in TNBC cells. (FIG. 11A) MDA-MB-231 or MDA-MB-468 cells were treated with 5 μM Bt-$NO_2$-OA, Bt-$NO_2$-SA or Bt-OA for 2 hr. After cell lysis, biotinylated $NO_2$—FAs with adducts were affinity purified using streptavidin agarose beads. Pulled-down RelA protein was then detected by immunoblotting. RelA and control β-actin immunoblots from the same input lysates used for affinity purification are shown below the panel. (FIG. 11B) Endogenous RelA protein levels were detected by immunoblotting probed with anti-RelA antibody using β-actin as a loading control. The relative total RelA levels (normalized by total β-actin) compared to untreated controls were quantified. *, $p<0.05$ versus untreated control. Significance was determined by one-way analysis of variance followed by the Tukey post test. (FIG. 11C) MDA-MB-231 or MDA-MB-468 cells were treated with vehicle (methanol), $NO_2$-OA (5 μM), or $NO_2$—SA (5 μM) for 6 hr, then cell lysates were harvested and immunoprecipitated by anti-RelA antibody followed by immunoblotting. Pull-down level of immunoprecipitated RelA proteins is shown below the panel.

FIG. 13A is a cartoon of different DNA DSB repair pathways. DNA DSB repair consists of four pathways: canonical non-homologous end joining (c-NHEJ), alternative enjoining (ALT-EJ), single strand annealing (SSA) and homologous recombination-directed repair (HDR). While NHEJ does not require homology (homologous sequence) to bridge the DSB prior to ligation, ALT-EJ is mediated by short stretches of homology to bridge DSB prior to ligation. SSA uses flanking homology to bridge the DNA lesion, causing a deletion between repeats. HDR is the major event of DSB repair that involves invasion of a homologous template by at least one strand from the DSB, which templates nascent DNA synthesis to form an extended strand that can form a bridge to the other DSB end. The homologous strand invasion step is catalyzed by the recombinase Rad51. End resection is the processing of chromosomal DSBs to generate 3' single strand DNA. Each of these pathways involves a specific set of DNA repair proteins (FIG. 13A).

FIG. 16A is a graph showing that nitroalkenes (e.g., methyl-ethyl-4-nitro-oct-4-enedioate (designated "CP-1" induce a lower $EC_{50}$ than OA-$NO_2$ for the inhibition of MDA-MB-231 TNBC cell growth. FIG. 16B is a graph showing the inhibition of homologous recombination in U2OS GFP-reporter constructs.

DETAILED DESCRIPTION

Terminology

Figure 1A:
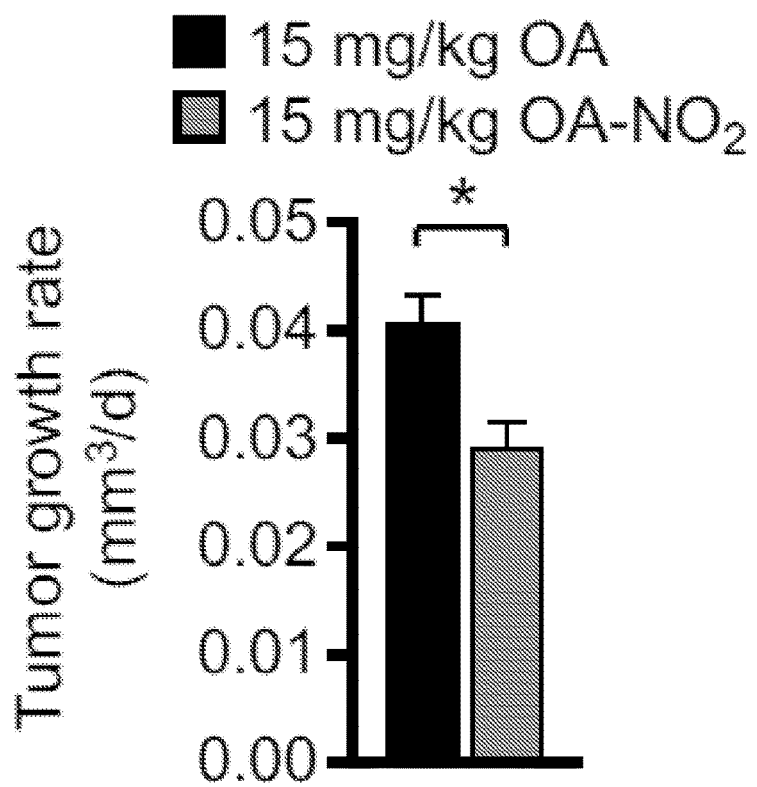

The following explanations of terms and methods are provided to better describe the present compounds, compositions and methods, and to guide those of ordinary skill in the art in the practice of the present disclosure. It is also to be understood that the terminology used in the disclosure is for describing particular embodiments and examples only and is not intended to be limiting.

"Administration" as used herein is inclusive of administration by another person to the subject or self-administration by the subject.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, isobutyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2, 2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and one or more triple bonds. Alkynyl groups may be unsubstituted or substituted.

The term "amine or amino" refers to an -NRPRq group wherein Rp and Rq each independently refer to a hydrogen, ($C_1$-$C_8$) alkyl, ($C_1$-$C_8$) haloalkyl, and ($C_1$-$C_6$) hydroxyalkyl group.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

As used herein, "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, OH, alkoxy, amino, $CO_2H$, $CO_2$alkyl, aryl, and heteroaryl. Exemplary aryl groups include but are not limited to phenyl, naphthyl, tetrahydronaphthyl, chlorophenyl, methylphenyl, methoxyphenyl, trifluoromethylphenyl, nitrophenyl, and 2,4-methoxychlorophenyl.

The term "biological sample" refers to tissue, cells, cellular extract, or homogenized tissue extract.

The term "co-administration" or "co-administering" refers to administration of a compound disclosed herein with at least one other therapeutic agent or therapy within the same general time period, and does not require administration at the same exact moment in time (although co-administration is inclusive of administering at the same exact moment in time). Thus, co-administration may be on the same day or on different days, or in the same week or in different weeks. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent and/or lowers the frequency of administering the potentially harmful (e.g., toxic) agent. "Co-administration" or "co-administering" encompass administration of two or more active agents to a subject so that both the active agents and/or their metabolites are present in the subject at the same time. Co-administration includes simultaneous administration in separate compositions, administration at different times in separate compositions, or administration in a composition in which two or more active agents are present.

Co-administration also encompasses delivery of a first agent via a first administration route and delivery of a second agent via a second administration route, wherein the first administration route and the second administration route are the same (e.g., both oral) or different (e.g, first is oral, second is topical).

The term "derivative" refers to a compound that is derived from a similar compound, or a compound that can be imagined to arise from another compound, if one or more atoms are replaced with another atom or group of atoms.

The term "haloalkyl," refers to a $C_1$-$C_5$ alkyl group wherein one or more hydrogen atoms in the $C_1$-$C_8$ alkyl group is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "halogen" and "halo" refers to —F, —Cl, —Br or —I.

The term "heteroatom" is meant to include oxygen (O), nitrogen (N), and sulfur (S).

The term "heteroaryl" is employed here to refer to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and preferably one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "heterocycle" refers to a monocyclic, bicyclic, tricyclic, or polycyclic systems, which are either unsaturated or aromatic and which contains from 1 to 4 heteroatoms, independently selected from nitrogen, oxygen and sulfur, wherein the nitrogen and sulfur heteroatoms are optionally oxidized and the nitrogen heteroatom optionally quaternized, including bicyclic, and tricyclic ring systems. The heterocycle may be attached via any heteroatom or carbon atom. Heterocycles include heteroaryls as defined above. Representative examples of heterocycles include, but are not limited to, benzoxazolyl, benzisoxazolyl, benzthiazolyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents.

"Heterocycloalkyl" denotes to a monocyclic or bicyclic ring system containing one or two saturated or unsaturated rings and containing at least one nitrogen, oxygen, or sulfur atom in the ring. The term "cycloalkyl" refers to a monocyclic or bicyclic ring system containing one or two saturated or unsaturated rings.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments, treating a disease refers to inhibiting metastasis of the disease.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, PA (19th Edition).

The compounds of the invention can exist in various isomeric forms, including configurational, geometric, and conformational isomers, as well as existing in various tautomeric forms, particularly those that differ in the point of attachment of a hydrogen atom. The term "isomer" is intended to encompass all isomeric forms of a compound of this invention, including tautomeric forms of the compound.

Certain compounds described here may have asymmetric centers and therefore exist in different enantiomeric and diastereomeric forms. The compounds of the invention can be in the form of an optical isomers or a diastereomers. Accordingly, the invention encompasses compounds in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents. Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY 6th ed. (Wiley, 2001) and DESIGN AND APPLICATION OF PRODRUGS (Harwood Academic Publishers Gmbh, 1985).

One embodiment disclosed herein involves co-administering a therapeutically effective amount of a compound (a) selected from (a)(i) a nitroalkene fatty acid, (a)(ii) an unsaturated fatty acid having an electron withdrawing group, a leaving group, and a carbon-carbon double bond disposed between the electron withdrawing group and the leaving group, (a)(iii) a thiolated nitro fatty acid, (a)(iv) a dicarboxylic acid compound containing an electron withdrawing group, or a mixture thereof, and therapeutically effective amount of at least one anti-neoplastic agent (b) for treating cancer. The co-administration with compound (a) enhances the anti-proliferative effect and apoptosis-inducing effect of the anti-neoplastic agent. The co-administration is particularly useful for treating cancer.

In certain embodiments, the combination therapy disclosed may be useful for treating any type of neoplasm (e.g., cancer). Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Illustrative neoplasms include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, multiple myeloma, and lymphoma.

In certain embodiments, the presently disclosed methods are directed to a method for inhibiting cancer growth, including processes of cellular proliferation, invasiveness, and metastasis in biological systems. Preferably, the method is employed to inhibit or reduce cancer cell proliferation, invasiveness, metastasis, or tumor incidence in living animals, such as mammals.

Also provided herein is a method of inducing cytotoxicity (cell killing) in cancer cells or reducing the viability of cancer cells.

Particularly illustrative cancers in include cancer with hereditary etiology of defects in DNA repair genes, cancer with a high rate of spontaneous genomic instability, cancer that responds well to DNA damaging agent(s), or cancer that responds well to a combination of DNA damaging agent(s) with immunotherapy. Illustrative cancers include breast, particularly triple negative breast cancer, colon, prostate, ovarian, brain cancer (glioblastoma), pancreatic, skin cancer (such as melanoma). Cancer cells that acquired the capability to spread (metastasize) and are highly genomically unstable and are particularly amenable to the combination treatments disclosed herein.

In certain embodiments, the compound (a) is a RAD51 inhibitor, thus inhibiting HDR, and a potent inhibitor of SSA, as described below in more detail.

In certain embodiments, the compound (a) is co-administered with a poly (ADP ribose) polymerase (PARP) inhibitor (PARPi) as described below in more detail.

Compound (a)(i)—Nitroalkene Fatty Acid

In certain embodiments, the (a)(i) nitroalkene fatty acid is a compound that includes at least one carbon-carbon double bond and at least one nitro group. Certain nitroalkene fatty acids are described, for example, in U.S. Pat. No. 7,776,916.

One illustrative embodiment of a nitroalkene fatty acid is of formula I:

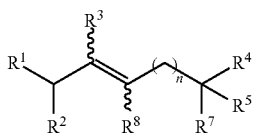

wherein $R^1$ is hydrogen, $C_1$-$C_{24}$ alkyl, $C_1$-$C_{24}$ alkenyl, or $C_1$-$C_{24}$ alkynyl;

$R^2$, $R^3$, $R^2$, and $R^8$ are each independently, hydrogen, oxygen, $C_1$-$C_{24}$ alkyl, $NO_2$, OH, or OOH; $R^4$ is a terminal $COOR^6$ group, wherein $R^6$ is hydrogen, $C_1$-$C_{24}$ alkyl, or a pharmaceutically acceptable counterion;

$R^5$ is hydrogen, $C_1$-$C_{24}$ alkyl, or $R^4$ and $R^5$ collectively form $=C(R^9)(R^{10})$, wherein $R^9$ comprises $C_1$-$C_{24}$ alkyl, $C_1$-$C_{24}$ alkenyl, or $C_1$-$C_{24}$ alkynyl, or wherein $R^9$ is a terminal $COOR^6$ group, and $R^{10}$ is hydrogen, $NO_2$, OH, or OOH;

n is from 1 to 24; and wherein the nitroalkene fatty acid includes at least one $NO_2$ group.

In certain embodiments, $R^3$ and $R^8$ are each independently, hydrogen, oxygen, $C_1$-$C_{24}$ alkyl, $NO_2$, CN, CHO, OH, or OOH; and $R^2$ and $R^7$ are each independently, hydrogen, oxygen, or $C_1$-$C_{24}$ alkyl.

In certain embodiments, $R^1$ is $C_1$-$C_{24}$ alkyl, more particularly $C_3$-$C_{20}$ alkyl.

In certain embodiments, $R^2$ is hydrogen.

In certain embodiments, one of $R^3$ or $R^8$ is $NO_2$ and the other of $R^3$ or $R^8$ is hydrogen.

In certain embodiments, n is 3 to 20.

In certain embodiments, $R^4$ is —COOH.

In certain embodiments, $R^5$ is hydrogen.

In certain embodiments, $R^7$ is hydrogen.

In certain embodiments, $R^4$ is —COOH; $R^5$ is methyl; and $R^7$ is methyl.

In certain embodiments, the nitroalkene fatty acid is of formula II:

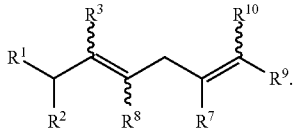

wherein $R^1$, $R^2$, $R^3$, $R^7$, $R^8$, $R^9$ and $R^{10}$ are the same as in formula I. In certain embodiments, R', $R^2$, and $R^9$ are the same as in formula I, and $R^3$, $R^7$, $R^8$, and $R^{10}$ are each independently, hydrogen, oxygen, $C_1$-$C_{24}$ alkyl, $NO_2$, CN, CHO, OH, or OOH.

In certain embodiments, the nitroalkene fatty acid is of formula III:

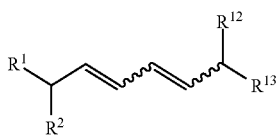

wherein $R^1$ is $C_1$-$C_{24}$ alkyl, $C_1$-$C_{24}$ alkenyl, or $C_1$-$C_{24}$ alkynyl;

$R^2$ and $R^{12}$ are each independently, hydrogen, $NO_2$, $ONOO_2$, ONO, OH, or OOH; and $R^{13}$ is a terminal $COOR^6$ group, wherein $R^6$ is hydrogen, $C_1$-$C_{24}$ alkyl, or a pharmaceutically acceptable counterion, and the nitroalkene fatty acid includes at least one $NO_2$ group.

In certain embodiments, $R^2$ and $R^{12}$ are each independently, hydrogen, $NO_2$, OH, or OOH In certain embodiments, the nitroalkene fatty acid is 10-nitro-octadec-9-enoic acid ($NO_2$-OA).

In certain embodiments, the nitroalkene fatty acid is 7-$NO_2$-nonadec-7-enoic acid (7-NDA) or 8-$NO_2$-nonadec-7-enoic acid (8-NDA).

In certain embodiments, the nitroalkene fatty acid (referred to herein as "7-NDA") is:

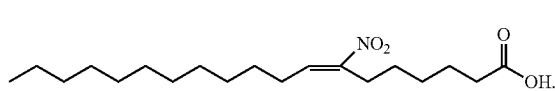 [SMILES: CCCCCCCCCCC/C=C(\CCCCCC(=O)O)[N+](=O)[O-]]

In certain embodiments, the nitroalkene fatty acid (referred to herein as "8-NDA") is:

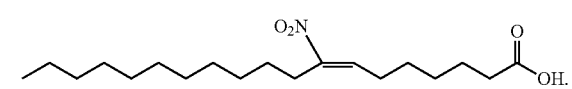 [SMILES: CCCCCCCCCCC/C(=C\CCCCCC(=O)O)[N+](=O)[O-]]

In certain embodiments, the nitroalkene fatty acid is 5-$NO_2$-eicos-5-enoic acid or 6-$NO_2$-eicos-5-enoic acid.

In certain embodiments, the nitroalkene fatty acid is substantially pure. In this aspect, the stereochemistry about the carbon-carbon double bond is substantially cis (or Z) or substantially trans (or E).

Compound (a)(ii)—Unsaturated Fatty Acid Having an Electron Withdrawing Group, a Leaving Group, and a Carbon-Carbon Double Bond Disposed Between the Electron Withdrawing Group and the Leaving Group In certain embodiments, the (a)(ii) unsaturated fatty acid having an electron withdrawing group, a leaving group, and a carbon-carbon double bond disposed between the electron withdrawing group and the leaving group is described, for example, in PCT Publication No. WO 2018/067709. In some embodiments, the unsaturated fatty acids may be nitrogen oxides of activated fatty acids in which the electron withdrawing group is nitro (—$NO_2$), and in particular embodiments, the unsaturated fatty acids may be nitrogen oxides of nitroalkenes in which the electron withdrawing group is a nitro group (—$NO_2$) and the leaving group may be a nitrogen oxide, such as nitrate (—$ONO_2$) or nitrite (—ONO). In certain embodiments, the compound (a)(ii) is a prodrug wherein the nitrite or nitrate substituent is cleaved, and the olefin shifts to yield an activated nitroalkene product. As used herein an "activated fatty acid" refers to a fatty acid having at least one electron withdrawing group covalently bound to a saturated or unsaturated aliphatic chain of a fatty acid. Such activated fatty acids may include an aliphatic chain substituted by any number of electron withdrawing groups at any number of positions and such electron withdrawing groups may or may not be associated with a carbon-carbon double bond. Similarly, the nitrogen oxide derivatives of nitroalkenes may include an aliphatic chain having any number of double bonds, which may or may not be associated with an electron withdrawing group. In certain embodiments, leaving group may be positioned at the beta ((3) carbon, gamma (γ) carbon, or delta (6) carbon of the unsaturated aliphatic chain, where the electron withdrawing group is attached to the alpha (a) carbon.

For example, the compounds of some embodiments may be of the general Formula IV:

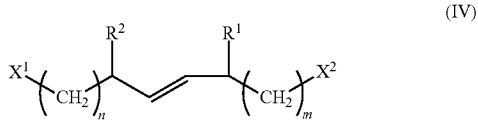

(IV)

wherein $R^1$ is any electron withdrawing groups including, but not limited to —COH, —COR, —COOH, —COOR, —Cl, —F, —Br, —I, —CF$_3$, —CN, —SO$_3-$, —SO$_2$R, —SO$_3$H, —NH$_3^+$, —NH$_2$R$^+$, —NHR$_2^+$, —NR$_3^+$ and —NO$_2$; $R^2$ is a leaving group including, but not limited to, —OC(O)(C$_{1-4}$), —ONO$_2$, —OPO(OH)$_2$, —OSO$_3$, and other inorganic esters; $X^1$ and $X^2$ are —H—COH, —COR, —COOH, —COOR, —COCF$_3$, and —CF$_2$R; and m and n are, independently, an integer from 1 to 10, and compositions containing the same.

Compounds in still other embodiments, may be of general Formula V:

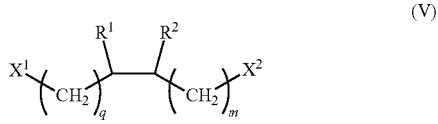

(V)

wherein $R^1$ is —H or any electron withdrawing groups including, but not limited to —COH, —COR, —COOH, —COOR, —Cl, —F, —Br, —I, —CF$_3$, —CN, —SO$_3$, —SO$_2$R, —SO$_3$H, —NH$_3^+$, —NH$_2$R$^+$, —NHR$_2^+$, —NR$_3^+$ and —NO$_2$; $R^2$ is a leaving group including, but not limited to, —OC(O)(C$_{1-4}$), —ONO$_2$, —OPO(OH)$_2$, —OSO$_3$, and other inorganic esters; $X^1$ and $X^2$ are —H—COH, —COR, —COOH, —COOR, —COCF$_3$, and —CF$_2$R; and m and n are, independently, an integer from 1 to 10, and compositions containing the same.

In certain embodiments, the nitrogen oxides of nitroalkenes may be of the general Formula VI:

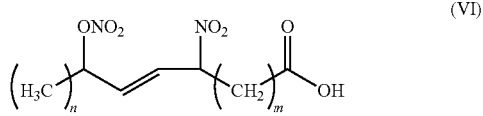

(VI)

wherein m and n are, independently, an integer from 1 to 10, and compositions containing the same.

In some embodiments, the nitrogen oxides of nitroalkene may be of Formula VII:

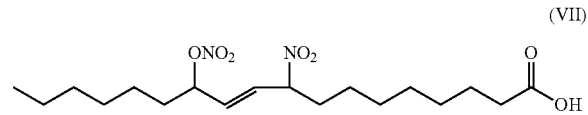

(VII)

In certain embodiments, the nitrogen oxide of nitroalkene of Formula VI is (E)-9-nitro-12-(nitrooxy)octadec-10-enoic acid, nitrogen oxides of conjugated linoleic acid, or NO$_2$—NO$_3$-CLA.

In such embodiments, the electron withdrawing group may be positioned in either E or Z configuration in the original double bond or in either R or S absolute stereochemistry at an sp$^a$ chiral/stereogenic center. For example, in one embodiment, a nitroxide derivative of nitroalkenes may have one electron withdrawing group, and in another, a nitroxide derivative of nitroalkenes may be substituted with multiple electron withdrawing groups at multiple positions along the hydrocarbon chain. While the reversible nitroxide derivatives of nitroalkenes may have an electron withdrawing group positioned at any carbon along the aliphatic hydrocarbon chain between the carboxy terminal carbon to the terminal methyl (w-position), in some embodiments, the electron withdrawing group may be positioned within about 3 carbons of either the carboxy terminal carbon and/or the methyl terminal carbon, and in other embodiments, the electron withdrawing group may be positioned within 5 carbons of either of the carboxy terminal carbon and/or the methyl terminal carbon. In still other embodiments, the electron withdrawing group may be positioned within 7 carbons of either of the carboxy terminal carbon and/or the methyl terminal carbon, and in further embodiments, the electron withdrawing group may be positioned within 9 carbons of either of the carboxy terminal carbon and/or the methyl terminal carbon.

In certain embodiments, the electron withdrawing group may be positioned on a carbon originating from a double bond of the activated fatty acid forming an "electron withdrawing vinyl" group. The electron withdrawing group of such vinyl groups may be on either side of the double bond. Fatty acids may have one or more than one electron withdrawing vinyl groups at any carbon on the aliphatic hydrocarbon chain, and there are several ways that an unsaturated fatty acid can have one electron-withdrawing group. In one embodiment, a reversible nitrogen oxides of oleic acid (octadec-9-enoic acid, OA) which originates from an 18 carbon, ω-9 fatty acid with one double bond (denoted "18:1") between the 9 h (C-9) and 10th (C-10) carbons, may have an electron withdrawing group at either C-9 or C-10, and a leaving group at the alternate position. In another exemplary embodiment, nitrogen oxides of linoleic acid (octadeca-9,12,-dienoic acid), which originated from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at C-9 or C-10, or C-12 or C-13, a leaving group at the corresponding alternate neighboring position, and at least one carbon-carbon double bond positioned between the electron withdrawing group and the leaving group. In another embodiment, a reversible nitrogen oxide of linoleic acid may have an electron withdrawing group at C-9 or C-10, or C-12 or C-13, a leaving group at the corresponding alternate neighboring position, and at least one carbon-carbon double bond adjacent to the leaving group. Similarly, other polyunsaturated fatty acids, originally having 3, 4, 5, 6 or more double bonds, can have one electron withdrawing at either position on any of the original double bond carbons, and a leaving group at the corresponding alternate position, with a carbon-carbon single bond between the electron withdrawing group and the leaving group including all possible permutations of positions and electron withdrawing groups.

The term "electron-withdrawing group" is recognized in the art and denotes the tendency of a substituent to attract valence electrons from neighboring atoms, i.e., the substituent is electronegative with respect to neighboring atoms. The term "nucleophile" or "electron-donating group" is recognized in the art and denotes the tendency of a substituent to donate excess valence electrons from neighboring atoms, i.e., the substituent is electropositive with respect to neighboring atoms. A quantification of the level of electron withdrawing capability is given by the Hammett sigma (σ) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example, the Hammet constant for para substituted $NH_2$ (σ[P]) is about −0.7 and the σ[P] for a nitro group is about +0.8.

Embodiments encompass any known electron withdrawing group. For example, electron-withdrawing groups may include, but are not limited to, aldehyde (—COH), acyl (—COR), carboxylic acid (—COOH), ester (—COOR), halides (—Cl, F, —Br, etc.), fluoromethyl (—$CF_3$), fluoroalkyl (—$CF_nH_{2-n}R$), cyano (—CN), sulfoxide (—SOR), sulfonyl (—$SO_2R$), sulfonate ($SO_3R$), 1°, 2° and 3° ammonium (—$NR_3^+$), and nitro (—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl.

The term "leaving group" is recognized in the art and denotes the tendency of a substituent to leave a parent molecule with a pair of electrons during heterolytic bond cleavage. Leaving groups encompassed include, for example, —OC(O)($C_{1-4}$), —$ONO_2$, —OPO(OH)$_2$, —$OSO_3$, other inorganic esters, and the like.

The fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments encompass such naturally occurring fatty acids as well as non-naturally occurring fatty acids, which may contain an odd number of carbons and/or a non-naturally occurring linker including heteroatoms. Thus, some embodiments include fatty acids having an odd number of carbons of, for example, from 5 to 23 carbons, and in other embodiments, from 11 to 17 carbons. In yet other embodiments, the fatty acids of embodiments may have greater than 23 carbons. The naturally and non-naturally occurring fatty acids may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically, "cis" is the same as Z, and "trans" is the same as E but sometimes the IUPAC rules for naming compounds will give the opposite of this for non-carbon substituents, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore, the nitroalkene analog of a "cis" double bond is termed an E nitroalkene. Similarly, the nitroalkene analog of a "trans" double bond is termed a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments may include reversible nitroxide derivatives of nitroalkenes having double bonds in either E or Z configuration, and encompass compositions that may include combinations of cis and trans containing nitroxide derivatives of nitroalkenes and regioisomers of the nitroxide derivatives of nitroalkenes.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega (ω)-3, ω-5, ω-6, ω-7, ω-9 carbon-carbon double bonds. Any such fatty acid may be useful in the compounds. The symbol 'ω' is used to refer to the terminal methyl carbon of the aliphatic hydrocarbon chain. The placement of the double bond of the ω-X fatty acid is the carbon-carbon bond X number of carbons from the w carbon. For example, an ω-6 fatty acid has a double bond between the $6^{th}$ and 7th carbons counting backward from the ω-carbon and an ω-3 fatty acid has a double bond between the 3rd and 4th carbons counting backward from the ω-carbon. Various embodiments include nitrated ω-3 fatty acids, including, but not limited to, linolenic acid, alphalinolenic acid, eicosapentanoic acid, docosapentaenoic acid, docosahexanoic acid and stearidonic acid; nitrated ω-5 fatty acids including, but not limited to, myristoleic acid; nitrated ω-6 fatty acids including, but not limited to, linoleic acid, gamma-linoleic acid, dihomo-gamma-linoleic acid and arachidonic acid; nitrated ω-7 fatty acids including, but not limited to, conjugated linoleic and palmitoleic acid; and nitrated ω-9 fatty acids including, but not limited to, oleic acid and erucic acid. Of course, the fatty acids may also be referred to using IUPAC nomenclature in which the placement of the double bond is determined by counting from the carbon of the carboxylic acid, and 'C-X' denotes the carbon in aliphatic hydrocarbons using IUPAC nomenclature wherein X is the number of the carbon counting from the carboxylic acid (including the carbonyl carbon itself).

Embodiments also include synthetic equivalents to naturally occurring fatty acids and derivatives thereof.

Other embodiments include unsaturated or polyunsaturated non-naturally occurring fatty acids which may have an odd number of carbons such as, for example, 5, 7, 9, 11, 13, 15, 17, 19, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups, which interrupt the aliphatic hydrocarbon chain. For example, in some embodiments, activated fatty acids may have one or more non-carbon-carbon linkage such as, for example, ester, ether, vinyl ether, thioether, amino, imine and the like at any position within the aliphatic hydrocarbon chain.

In still other embodiments, the carboxy-terminal end of the nitrogen oxides of activated fatty acid may be modified. For example, in some embodiments, the nitrogen oxides of activated fatty acid may include a glycerol associated with the carboxy-terminal end of the fatty acid to create a glycerolipid, and such glycerolipids may be mono-, di-, or tri-glycerides wherein at least one of the fatty acids of a di or tri-glyceride may be an activated-nitrate fatty acid and any remaining fatty acids may be a saturated or unsaturated fatty acid. Similarly, in other embodiments, a carbohydrate may be associated with the carboxy-terminal end of an nitrogen oxides activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of an activated-nitrate fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the activated fatty acids may be associated with a phosphate to form a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one activated-nitrate the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In particular embodiments, carboxy-terminal modifications including a glycerol may not include a nitro group. Without wishing to be bound by theory, modification of the carboxy-terminal end of activated-nitrate fatty acids may enhance partitioning of the activated fatty acid after administration and may also improve resilience of the activated fatty acid by inhibiting beta-oxidation in mitochondria following administration.

Compound (a)(iii)—Thiol-Adducted Nitro Fatty Acid ("Thiolated Fatty Acid")

A potential barrier to the use of nitro-oleic acid as a drug candidate is its rapid metabolism as a result of beta-oxidation reactions and reduction of the nitroalkene by Prostaglandin Reductase 1, in the liver first pass and reversible adduction with glutathione and excretion. To increase efficacy, the drug must withstand the first pass metabolism. An active drug would be metabolized within the gut microbiome and liver, and thus must be protected in order to appropriately deliver an effective amount of the active drug into circulation.

The modification of nitroalkene fatty acids by reversible thiolation of the nitroalkene prevents its metabolic inactivation, thus preserving the potential electrophilic character of the nitroalkene fatty acid. Upon dissociation of the thiol or poly thiol substituent, the "activated" nitroalkene product become competent to target functionally significant nucleophilic residues in RAD51 or other DNA repair proteins.

Examples of thiolated fatty acids are described, for example, in PCT Publication No. WO 2018/067705.

Embodiments are generally directed to thiolated electrophilic unsaturated activated fatty acids and, in particular, thiolated unsaturated nitrated fatty acids. As used herein an "activated fatty acid" refers to a fatty acid having at least one electron withdrawing group covalently bound to an unsaturated carbon of the saturated or unsaturated aliphatic chain of a fatty acid. Such activated fatty acids may include an aliphatic chain substituted by any number of electron withdrawing groups at any number of positions on the hydrocarbon chain and such electron withdrawing groups may or may not be associated with a carbon-carbon double bond. Similarly, the thiolated activated fatty acids described herein may include an aliphatic chain having any number of double bonds, which may or may not be associated with an electron withdrawing group, and a sulfur containing group, i.e. a thiol group. In certain embodiments, the sulfur containing group may be positioned at the beta (β) carbon, gamma (x) carbon, or delta (δ) carbon of the unsaturated aliphatic chain, where the electron withdrawing group is attached to the alpha (a) carbon.

The electrophilic double bond of the nitroalkene is reversibly protected by $H(S)_xR$ forming the thiolated-activated fatty acid. This thiolated-activated fatty acid is now a prodrug and avoids metabolic processes during first pass. The electrophilic double bond is regenerated following the loss of the protective group, as depicted below:

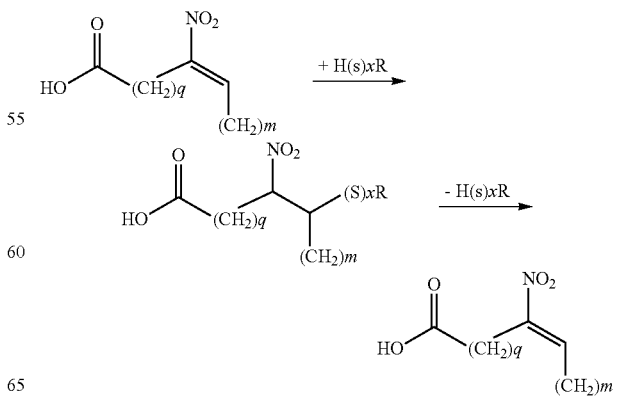

For example, thiolated activated fatty acids of some embodiments may be of general Formula VIII:

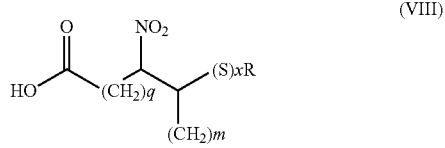
(VIII)

wherein R is hydrogen (—H), methyl, or C$_2$ to C$_6$ alkyl, alkenyl, or alkynyl, or (S)xR may be a sulfur containing functional group such as, sulfino (—SOOH), sulfo (—SOOOH), or thiocyanate (—SCN), x is an integer from 1 to 5, and q and m are each, independently, an integer from 1 to 10. Compounds of Formula VIII include a sulfur containing group at the β carbon.

Other thiolated activated fatty acids include compounds of the general Formula IX:

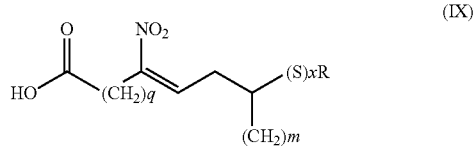
(IX)

wherein R is hydrogen (—H), methyl, or C$_2$ to C$_6$ alkyl, alkenyl, or alkynyl, or (S)xR may be a sulfur containing functional group such as, sulfino (—SOOH), sulfo (—SOOOH), or thiocyanate (—SCN), x is an integer from 1 to 5, and q and m are each, independently, an integer from 1 to 10. Compounds of Formula IX include a sulfur containing group at the δ carbon.

In some embodiments, R for Formulae VIII or IX may be a bifunctional alkyl, alkenyl, or alkynyl, that is attached to the carboxyl of the activated fatty acid forming bridged or cyclic structures. In such embodiments, the sulfur containing moiety may be positioned at either β, χ, or δ carbon. For example, the compounds of the general Formulae Xa and Xb, which include cyclized bifunctional sulfur containing moieties at the β carbon:

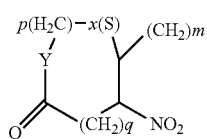
(Xa)

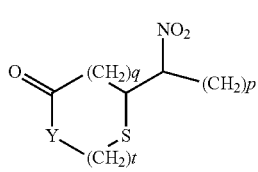
(Xb)

wherein each Y is, independently, oxygen (O) or nitrogen (N), each x is, independently, an integer from 1 to 5, and q, m, p, and t are each, independently, an integer from 1 to 10.

In some embodiments, the sulfur containing group may join two activated fatty acids. For example, various embodiments are directed to compounds of the general Formula XI:

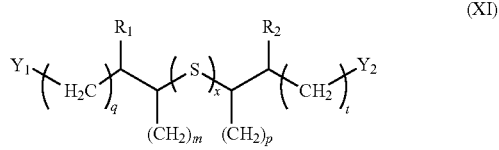
(XI)

wherein R$_1$ and R$_2$ are independently selected from —H and any electron withdrawing groups including, but not limited to —COH, —COR, —COOH, —COOR, —Cl, —F, —Br, —I, —CF$_3$, —CN, —SO$_{3-}$, —SO$_2$R, —SO$_3$H, —NH$_3^+$, —NH$_2$R$^+$, —NHR$_2^+$, —NR$_3^+$ and —NO$_2$; wherein at least one of R$_1$ and R$_2$ is an electron withdrawing group; wherein Y$_1$ and Y$_2$ are independently selected from —H, —COH, —COR, —COOH, and —COOR; wherein at least one of R$_1$ and R$_2$ is an electron withdrawing group; and wherein x is an integer from 1 to 5, and q, m, p, and t are, independently, an integer from 1 to 10, and compositions containing the same.

Various embodiments are directed to compounds of the general Formulas XII, XIIb, and XIIc:

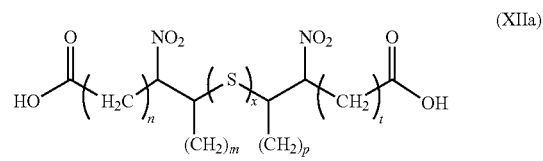
(XIIa)

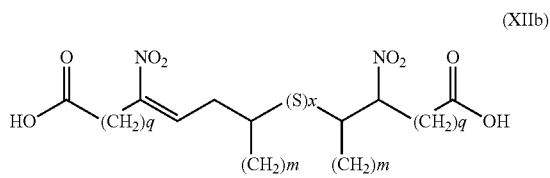
(XIIb)

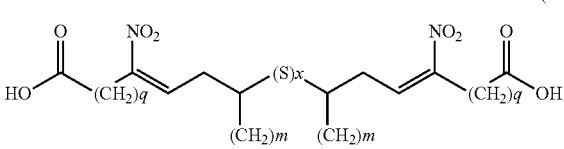
(IIc)

wherein x is an integer from 1 to 5, and q, m, p, and t are, independently, an integer from 1 to 10, and compositions containing the same.

Other embodiments, include compounds of Formula XIII:

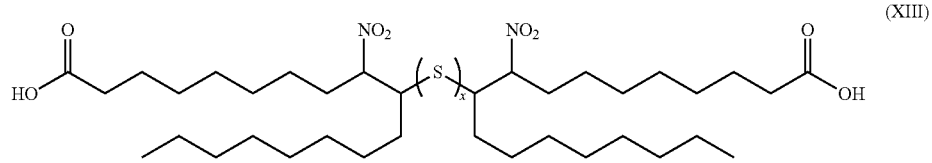
(XIII)

wherein x is an integer from 1 to 5, and compositions containing the same.

In some embodiments, the compound is a thiolated nitro-oleic acid ($NO_2$-OA-$S_x$) species depicted as Formula XIV:

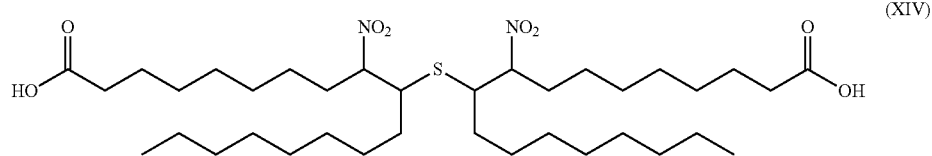 [SMILES: CCCCCCCCC(SC(CCCCCCCC)C(CCCCCCCC(=O)O)[N+](=O)[O-])C(CCCCCCCC(=O)O)[N+](=O)[O-]]
(XIV)

The electron withdrawing group may be positioned in either cis or trans configuration in the original double bond or in either R or S absolute stereochemistry at an $sp^3$ chiral/stereogenic center. For example, in one embodiment, a thiolated activated fatty acid may have one electron withdrawing group, and in another, a thiolated activated fatty acid may be substituted with multiple electron withdrawing groups at multiple positions along the hydrocarbon chain. While the thiolated activated fatty acids may have an electron withdrawing group positioned at any carbon along the aliphatic hydrocarbon chain between the carboxy terminal carbon to the terminal methyl (ω-position), in some embodiments, the electron withdrawing group may be positioned within about 3 carbons of either the carboxy terminal carbon and/or the methyl terminal carbon, and in other embodiments, the electron withdrawing group may be positioned within 5 carbons of either of the carboxy terminal carbon and/or the methyl terminal carbon. In still other embodiments, the electron withdrawing group may be positioned within 7 carbons of either of the carboxy terminal carbon and/or the methyl terminal carbon, and in further embodiments, the electron withdrawing group may be positioned within 9 carbons of either of the carboxy terminal carbon and/or the methyl terminal carbon.

In certain embodiments, the electron withdrawing group may be positioned on a carbon originating from a double bond of the activated fatty acid forming an "electron withdrawing vinyl" group. The electron withdrawing group of such vinyl groups may be on either side of the double bond. Fatty acids may have one or more than one electron withdrawing vinyl groups at any carbon on the aliphatic hydrocarbon chain, and there are several ways that an unsaturated fatty acid can have one electron withdrawing group. In one embodiment, a thiolated activated oleic acid (octadec-9-enoic acid) which originates from an 18 carbon, ω-9 fatty acid with one double bond (denoted "18:1") between the 9 h (C-9) and 10th (C-10) carbons, may have an electron withdrawing group at either C-9 or C-10, and a thiol (—SR) at the alternate position. In another exemplary embodiment, a thiolated activated linoleic acid (octadeca-9,12,-dienoic acid), which originated from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at C-9 or C-10, or C-12 or C-13, and a thiol (—SR) at the corresponding alternate neighboring position. Similarly, other polyunsaturated fatty acids, originally having 3, 4, 5, 6 or more double bonds, can have one electron withdrawing at either position on any of the original double bond carbons, and a thiol (—SR) at the corresponding alternate neighboring position, including all possible permutations of positions and electron withdrawing groups.

In other embodiments, a mono or polyunsaturated fatty acid may have two electron-withdrawing groups, and there are several ways that an unsaturated fatty acid can have two electron-withdrawing groups. For example, in one embodiment, a thiolated activated linoleic acid (octadeca-9,12,-dienoic acid), which originates from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at any two of the positions C-9, C-10, C-12 or C-13, with the following possible permutations: C-9 and C-12, C-9 and C-13, C-10 and C-12, or C-10 and C-13, and one or more thiols (—SR) at the corresponding alternate neighboring positions.

In analogy to the preceding descriptions of compounds with one electron withdrawing group or two electron-withdrawing groups, it is also possible to have three, four, five or more electron withdrawing groups. Following the same logic above, in the preceding descriptions of compounds with one electron-withdrawing group or two electron-withdrawing groups, polyunsaturated fatty acids, with 3, 4, 5, 6 or more double bonds, conjugated or non-conjugated, can have multiple electron withdrawing (three, four, five or more, as available positions for substitution permit) at any of the positions on any of the double bond carbons, including all possible permutations of positions, nucleophilic substituents, and electron-withdrawing groups. Additionally, in any embodiments such as those described above, any number of non-electron-withdrawing groups may be covalently bound to carbons of the aliphatic chain of the activated fatty acid. For example, in some embodiments, the thiolated activated fatty acids may include one or more methyl, $C_2$-$C_6$ alkyl, alkenyl, or alkynyl or amino covalently attached to one or more carbons of the aliphatic chain of a thiolated activated fatty acid.

The term "electron-withdrawing group" is recognized in the art and denotes the tendency of a substituent to attract valence electrons from neighboring atoms, i.e., the substituent is electronegative with respect to neighboring atoms. The term "nucleophile" or "electron-donating group" is recognized in the art and denotes the tendency of a substituent to donate excess valence electrons from neighboring atoms, i.e., the substituent is electropositive with respect to neighboring atoms. A quantification of the level of electron withdrawing capability is given by the Hammett sigma ($\sigma$) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example, the Hammet constant for para substituted $NH_2$ ($\sigma[P]$) is about −0.7 and the $\sigma[P]$ for a nitro group is about +0.8.

Embodiments encompass any known electron withdrawing group. For example, electron-withdrawing groups may include, but are not limited to, aldehyde (—COH), acyl (—COR), carboxylic acid (—COOH), ester (—COOR), halides (—Cl, F, —Br, etc.), fluoromethyl (—$CF_3$), fluoroalkyl (—$CF_nH_{2-n}R$), cyano (—CN), sulfoxide (—SOR), sulfonyl (—$SO_2R$), sulfonate ($SO_3R$), 1°, 2° and 3° ammonium (—$NR_3^+$), and nitro (—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a $\sigma$ of at least about 0.2, and in certain embodiments, the electron withdrawing group may form a dipole. For example, in particular embodiments, the electron withdrawing group may be a nitro, ammonium or sulfonyl. In other embodiments, the thiolated activated fatty acids may be additionally substituted by non-electron withdrawing groups or electron donating groups including, for example, thiol (—SR), alcohol (—OH), reverse ester (—OOCR), alkyl, alkenyl, alkynyl, 1° and 2° amines (—$NR_2$), N-containing heterocycle (—N=, —NR—), nitrate (—$ONO_2$), nitrito (—ONO) and the like.

The fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments encompass such naturally occurring fatty acids as well as non-naturally occurring fatty acids, which may contain an odd number of carbons and/or a non-naturally occurring linker including heteroatoms. Thus, some embodiments include fatty acids having an odd number of carbons of, for example, from 5 to 23 carbons, and in other embodiments, from 11 to 17 carbons. In yet other embodiments, the fatty acids of embodiments may have greater than 23 carbons. The naturally and non-naturally occurring fatty acids may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically, "cis" is the same as Z, and "trans" is the same as E but sometimes the IUPAC rules for naming compounds will give the opposite of this for non-carbon substituents, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is termed an E nitroalkene. Similarly, the nitroalkene analog of a "trans" double bond is termed a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments may include thiolate activated fatty acids having double bonds in either cis or trans configuration, and encompass compositions that may include combinations of cis and trans containing thiolated activated fatty acids and regioisomers of the thiolated activated fatty acids.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega ($\omega$)-3, $\omega$-5, $\omega$-6, $\omega$-7, $\omega$-9 carbon-carbon double bonds. Any such fatty acid may be useful. The symbol '$\omega$' is used to refer to the terminal methyl carbon of the aliphatic hydrocarbon chain. The placement of the double bond of the $\omega$-X fatty acid is the carbon-carbon bond X number of carbons from the w carbon. For example, an $\omega$-6 fatty acid has a double bond between the $6^{th}$ and 7th carbons counting backward from the $\omega$-carbon and an $\omega$-3 fatty acid has a double bond between the 3rd and 4th carbons counting backward from the $\omega$-carbon. Various embodiments include nitrated $\omega$-3 fatty acids, including, but not limited to, linolenic acid, alphalinolenic acid, eicosapentanoic acid, docosapentaenoic acid, docosahexaenoic acid and stearidonic acid; nitrated $\omega$-5 fatty acids including, but not limited to, myristoleic acid; nitrated $\omega$-6 fatty acids including, but not limited to, linoleic acid, gamma-linoleic acid, dihomo-gamma-linoleic acid and arachidonic acid; nitrated $\omega$-7 fatty acids including, but not limited to, conjugated linoleic and palmitoleic acid; and nitrated $\omega$-9 fatty acids including, but not limited to, oleic acid and erucic acid. Of course, the fatty acids may also be referred to using IUPAC nomenclature in which the placement of the double bond is determined by counting from the carbon of the carboxylic acid, and 'C-X' denotes the carbon in aliphatic hydrocarbons using IUPAC nomenclature wherein X is the number of the carbon counting from the carboxylic acid (including the carbonyl carbon itself). Embodiments also include synthetic equivalents to naturally occurring fatty acids and derivatives thereof.

Other embodiments include unsaturated or polyunsaturated non-naturally occurring fatty acids which may have an odd number of carbons such as, for example, 5, 7, 9, 11, 13, 15, 17, 19, 20, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups, which interrupt the aliphatic hydrocarbon chain. For example, in some embodiments, activated fatty acids may have one or more non-carbon-carbon linkage such as, for example, ester, ether, vinyl ether, thioether, amino, imine and the like at any position within the aliphatic hydrocarbon chain.

Various embodiments include unsaturated or polyunsaturated fatty acids that may have a carbon-carbon double bond between any two carbons of the aliphatic chain of the fatty acid, and any number of carbon-carbon double bonds may be present in such polyunsaturated fatty acids. For example, in some embodiments, polyunsaturated fatty acids may have 2, 3, 4, 5, 6 or more carbon-carbon double bonds. In such embodiments, each of the more than one carbon-carbon double bond may individually be in either cis or trans configuration. In some embodiments, thiolated activated fatty acids are derived from reaction with at least one of the carbon-carbon double bonds of a polyunsaturated fatty acid which has an associated electron withdrawing group, and in other embodiments, more than one of the carbon-carbon double bonds of such polyunsaturated fatty acids may have an associated electron withdrawing group. Additionally, in such embodiments, the electron withdrawing group may be associated with either carbon of the original carbon-carbon double bond or a carbon directly adjacent to either carbon of the carbon-carbon double bond, and the thiol may be associated with the other carbon of the original carbon-carbon double bond or a carbon directly adjacent to either carbon of the carbon-carbon double bond. For example, in some embodiments, an electron withdrawing group may be attached to the alpha (α) carbon of the former carbon-carbon double bond, and in other embodiments, an electron withdrawing group may be associated with the beta (β) carbon of the former carbon-carbon double bond. In those embodiments, a thiol would be attached respectively to the beta (β) carbon of the former carbon-carbon double bond, and in other embodiments, an electron withdrawing group may be associated with the alpha (α) carbon of the former carbon-carbon double bond.

In particular embodiments, an unsaturated fatty acid having at least one electron withdrawing group may be a conjugated fatty acid. In such embodiments, two carbon-carbon double bonds in an aliphatic chain are adjacent to one another such that there is no methylene group between them. Such conjugated compounds are commonly called 1,3-dienes, or conjugated fatty acids. Such 1,3-dienes may include one or more electron withdrawing groups at any of 6 positions, at the 1, 2, 3, and/or 4 positions of the 1,3-dienes and at the two carbons adjacent to the diene (at the 0 and 5 positions, in relation to the 1, 2, 3, 4 method of identifying carbons in a 1,3-diene). For example, one associated electron withdrawing group may be attached to any of the 6 positions identified above, that is to either the 1, 2, 3, or 4 positions on the diene or to either of the carbons adjacent to the 1,3-diene (at the 0 or 5 positions, as described above). In additional embodiments, two associated electron withdrawing groups could be attached to any two of the six possible positions, three associated electron withdrawing groups could be attached to any two of the six possible positions, four associated electron withdrawing groups could be attached to any two of the six possible positions, five associated electron withdrawing groups could be attached to any two of the six possible positions, and six associated electron withdrawing groups could be attached to any two of the six possible positions. In summary, any configuration of electron withdrawing groups attached to any of the six positions described above in a 1,3-diene are encompassed by embodiments of the compound.

In certain embodiments, the thiolated activated fatty acids may undergo an isomerization following preparation such that either the cis/trans configuration of the double bond, the location of the double bond in the carbon chain, or both, may change. For example, in some embodiments, a thiolated activated fatty acid may be prepared from a carbon-carbon double bond of having an electron withdrawing group attached to a gamma carbon of a carbon-carbon double bond. Following preparation, the carbon-carbon double bond may undergo an isomerization such that the electron withdrawing group is now conjugated with the carbon-carbon double bond after isomerization. Such isomerizations may occur spontaneously at any time following preparation, and may result in a composition which may have initially been prepared as including a single species of a thiolated activated fatty acid that subsequently includes a combination of isomers of the first-prepared activated fatty acid originally produced.

In still other embodiments, the carboxy-terminal end of the thiolated activated fatty acid may be modified. For example, in some embodiments, the thiolated activated fatty acid may include a glycerol associated with the carboxy-terminal end of the fatty acid to create a glycerolipid, and such glycerolipids may be mono-, di-, or tri-glycerides wherein at least one of the fatty acids of a di or tri-glyceride may be a thiolated activated fatty acid and any remaining fatty acids may be a saturated or unsaturated fatty acid. Similarly, in other embodiments, a carbohydrate may be associated with the carboxy-terminal end of a thiolated activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of a thiolated activated fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the activated fatty acids may be associated with a phosphate to form a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one thiolated activated the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In particular embodiments, carboxy-terminal modifications including a glycerol may not include a nitro group. Without wishing to be bound by theory, modification of the carboxy-terminal end of thiolated activated fatty acids may enhance partitioning of the activated fatty acid after administration and may also improve resilience of the activated fatty acid by inhibiting beta-oxidation in mitochondria following administration.

The compounds increase the bioavailability of the activated fatty acid present as a dimer within the thiolated molecule. Thiolation of the electrophilic alkene protects the molecule through the first pass metabolism of the intestinal tract and liver. This protection occurs by preventing reduction of the alkene by Prostaglandin Reductase 1 and by delaying the adduction with glutathione. Further, the longer polysulfide chain the greater the stability of the molecule, providing for an extended release of the activated fatty acid in circulation. When the thioloated nitro fatty acid releases the nitro fatty acid and a hydrogen sulfide, an additional protective measure is provided.

Compound (a)(iv)—Dicarboxylic Acid Compound Containing an Electron Withdrawing Group Compounds (a)(iv) are dicarboxylic acid compounds containing electron withdrawing groups, and in some embodiments such compounds may further contain alkenes associated with the electron withdrawing groups. Various embodiments are directed to alkyl esters of dicarboxylic acid compounds containing electron withdrawing groups, and in some embodiments such compounds may further contain alkenes associated with the electron withdrawing groups. Various embodiments of the invention are directed to compounds of Formulae XV to XXIV. Such compounds are described, for example, in PCT Publication No. WO 2017/151938. These electrophilic dicarboxylates are competent to alkylate functionally significant thiols and inactivate RAD51 or other DNA repair proteins.

The compounds may be of general Formulae XV or XVI:

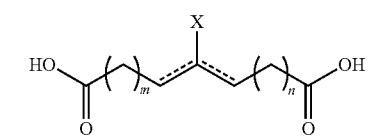

XV

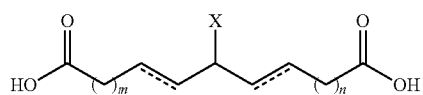

XVI wherein X is an electron withdrawing group, each ====== can, individually, be a single or double bond, and each m and n are, independently, an integer of 1 to 10. In particular embodiments, at least one ====== depicted in Formulae XV and XVI is a double bond. In some embodiments, both ====== depicted in Formulae XV and XVI may be single bonds, and in other embodiments, both ====== depicted in Formulae XV and XVI may be double bonds. In other embodiments, the compounds may be of general Formulae XVII and XVIII:

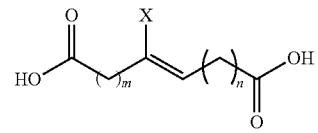

XVII

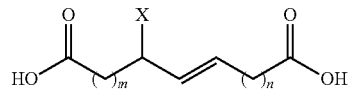

XVIII wherein X is an electron withdrawing group and each m and n are, independently, an integer of 1 to 10.

Further embodiments are directed to alkyl esters of the dicarboxylic acid compounds containing electron withdrawing groups such as, for example, compounds of general Formulae XIX and XX:

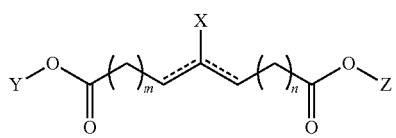

XIX

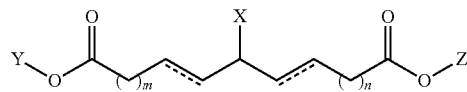

XX wherein X is an electron withdrawing group, each Y and Z is, individually, hydrogen or a $C_1$ to $C_{10}$ alkyl, each ====== is, individually, a single or double bond, and each m and n are, independently, absent or an integer of 1 to 10. In particular embodiments, at least one ====== depicted in Formulae XIX and XX is a double bond. In some embodiments, both ====== depicted in Formulae XIX and XX may be single bonds, and in other embodiments, both ====== depicted in Formulae XIX and XX may be double bonds. In some embodiments, the alkyl esters of dicarboxylic acid compounds containing electron withdrawing groups may be compounds of Formula XXI and XXII:

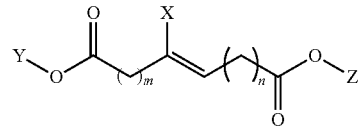

XXI

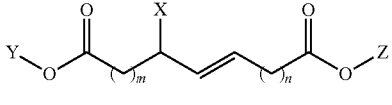

XXII wherein X is an electron withdrawing group, each Y and Z is, individually, hydrogen or a $C_1$ to $C_{10}$ alkyl, and each m and n are, independently, an integer of 1 to 10. In certain embodiments, each Y and Z of the compounds of Formulae XIX, XX, XXI, and XXII illustrated above may be methyl ($C_1$ alkyl) or ethyl ($C_2$ alkyl).

The alkylene created by m and n in each of the compounds of Formulae XV-XXII illustrated above may include carbon-carbon double bonds in addition to the double bonds depicted in Formulae XVII, XVIII, XXI, and XXII or optionally present as indicated by of Formulae XV, XVI, XIX, and XX. For Example, the compounds of some embodiments may be of Formulae XXIII and XXIV:

XXIII

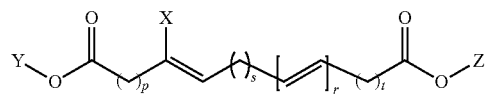

XXIV

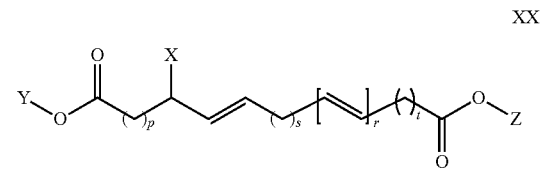

wherein X is an electron withdrawing group, each Y and Z is, individually, hydrogen or $C_1$ to $C_{10}$ alkyl, and each p and t are, independently, an integer of 1 to 10, each s is absent or an integer of 1 to 10, and each r is an integer of 1 to 5. In certain embodiments, each Y and Z of the compounds of Formulae XXIII and XXIV illustrated above may be methyl ($C_1$ alkyl) or ethyl ($C_2$ alkyl).

Additional embodiments are directed to dicarboxylic acid compounds containing electron withdrawing groups further containing at least one alkene associated with the electron withdrawing group of Formulae XV, XVII, XIX, XXI and XXIII, wherein at least one alkene associated with the electron withdrawing group has been reduced the introduction of a nucleophile "A" by means of a Michael addition reaction to yield compounds of Formulae XVA, XVIIA, XIXA, XIXB, XXIA and XXIIIA.

XVA

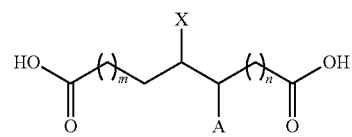

XVIIA

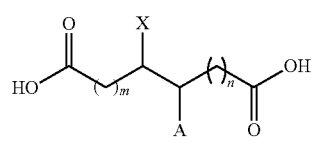

XIXA

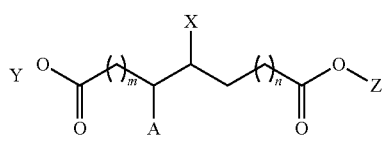

XIXB

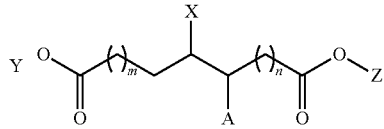

XXIA

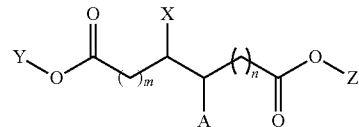

XXIIIA

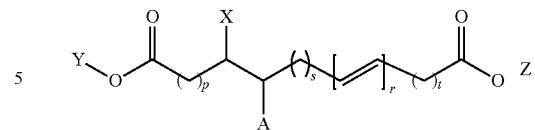

wherein X is an electron withdrawing group, A is a nucleophile, each Y and Z is, individually, hydrogen or $C_1$ to $C_{10}$ alkyl, and each m, n, p and t are, independently, an integer of 1 to 10, each s is absent or an integer of 1 to 10, and each r is an integer of 1 to 5. In certain embodiments, each Y and Z may be methyl ($C_1$ alkyl) or ethyl ($C_2$ alkyl).

It is envisioned that the compounds of Formulae XVA, XVIIA, XIXA, XIXB, XXIA and XXIIIA could be useful as either prodrugs of the compounds of Formulae XV, XVII, XIX, XXI and XXIII or as active therapeutic agents themselves. If used as prodrugs, it is envisioned that the compounds of Formulae XVA, XVIIA, XIXA, XIXB, XXIA and XXIIIA would metabolize in vivo after administration to a patient in need thereof to provide a therapeutically effective amount of the active agent according to Formulae XV, XVII, XIX, XXI and XXIII.

The term "nucleophile" is recognized in the art and denotes a chemical species that donates an electron pair to an electrophile to form a chemical bond in relation to a reaction. All molecules or ions with a free pair of electrons or at least one n-bond can act as electrophiles. Nucleophiles, i.e., A, may include but are not limited to, enols, hydroxide anion, alcohols, alkoxide anions, hydrogen peroxide, carboxylate anions, hydrogen sulfide, thiols, thiolate anions, anions of thiocarboxylic acids, anions of dithiocarbonates, ammonia, azide, amines and nitriles.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example, the Hammet constant for para substituted $NH_2$ (σ[P]) is about −0.7 and the σ[P] for a nitro group is about 0.8. Electron-withdrawing groups may include, but are not limited to, aldehyde (—COH) acyl (—COR), carbonyl (—CO), carboxylic acid (—COOH), ester (—COOR), halides (—Cl, —F, —Br, etc.), fluoromethyl (—$CF_n$), cyano (—CN), sulfonyl (—SO), sulfone (—$SO_2R$), sulfonic acid (—$SO_3H$), 1°, 2°, and 3° ammonium (—$NR^{3+}$), and nitro (—$NO_2$). In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium, or sulfonyl.

In certain embodiments, the dicarboxylic acid compound has the structure:

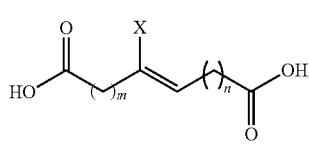

wherein m is from 1 to 10;
n is from 1 to 10;
the double bond is cis to trans; and
X is an electron withdrawing group selected from —NO₂, —CN, halide, $C_xF_{2,1}$, wherein x is from 1 to 5, SOR, wherein R is H or $C_1$-$C_6$ alkyl, SO₂R, wherein R is H or $C_1$-$C_6$ alkyl, or SO₃R, wherein R is H or $C_1$-$C_6$ alkyl.

In certain embodiments, X is —NO₂.

In certain embodiments, the compound is an alkyl ester of a dicarboxylic acid having a structure of:

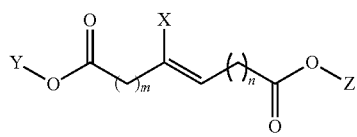

wherein m is from 1 to 10;
n is from 1 to 10;
the double bond is cis to trans;
Y and Z are each, independently a $C_1$ to $C_{10}$ alkyl, alkenyl or alkynyl;
and X is an electron withdrawing group selected from —NO₂, —CN, halide, $C_xF_{2,1}$, wherein x is from 1 to 5, SOR, wherein R is H or $C_1$-$C_6$ alkyl, SO₂R, wherein R is H or $C_1$-$C_6$ alkyl, or SO₃R, wherein R is H or $C_1$-$C_6$ alkyl.

In certain embodiments, m is 2 and n is 2.
In certain embodiments, Y and Z are each, independently a $C_1$ to $C_6$ alkyl, more particularly methyl or ethyl.
In certain embodiments, X is —NO₂.

In certain embodiments, the compound is an alkyl ester of a dicarboxylic acid having a structure of:

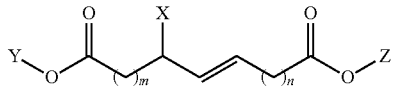

wherein m is from 1 to 10;
n is from 1 to 10;
the double bond is cis to trans;
Y and Z are each, independently a $C_1$ to $C_{10}$ alkyl, alkenyl or alkynyl;
and X is an electron withdrawing group selected from —NO₂, —CN, halide, $C_xF_{2,1}$, wherein x is from 1 to 5, SOR, wherein R is H or $C_1$-$C_6$ alkyl, SO₂R, wherein R is H or $C_1$-$C_6$ alkyl, or SO₃R, wherein R is H or $C_1$-$C_6$ alkyl.

hi certain embodiments, m is 2 and n is 2.
hi certain embodiments, Y and Z are each, independently a $C_1$ to $C_6$ alkyl, more particularly methyl or ethyl.
In certain embodiments, X is —NO₂.
hi certain embodiments, the compound is:

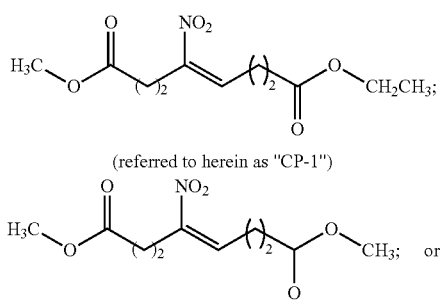

(referred to herein as "CP-1")

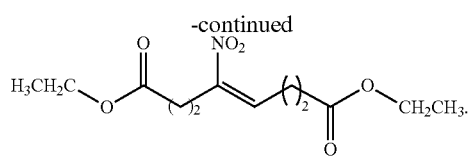

Compound (b)—Anti-Neoplastic Agents

In certain embodiments the anti-neoplastic agent is a DNA-damaging agent or DNA-damaging treatment. Illustrative anti-neoplastic agents include doxorubicin, cisplatin, olaparib, rucaparib, niraparib, talazoparib, veliparib, camptothecin, and irradiation treatment (IR).

In certain embodiments, co-administration of a compound (a) with the anti-neoplastic agents doxorubicin, cisplatin, IR or olaparib enhances the cell-killing, anti-proliferative, anti-tissue invasion and/or anti-metastatic effect(s) of these DNA damaging therapeutic strategies in TNBC cells. NO₂-OA was identified to suppress IR-induced RAD51 foci formation, inhibit RAD51 binding to ssDNA, decrease HR, induce phosphorylation of Ser139 H2AX (γH2AX), disrupt RAD51-ABL heterodimerization, and decrease RAD51 Tyr315 phosphorylation. These observations reinforce the concept that reactive species induce genomic perturbations in part via the disruption of HR and reveal a novel therapeutic strategy—that redox-derived soft electrophiles sensitize cancer cells to DNA-directed therapeutic strategies such as IR, cisplatin and doxorubicin.

Fatty acid nitroalkenes are endogenously produced products of nitric oxide- and nitrite-dependent nitration of unsaturated fatty acids. By virtue of kinetically rapid and reversible Michael addition, fatty acid nitroalkenes will mediate the PTM of susceptible Cys residues of proteins, in some cases modifying protein function and inducing signaling responses via pleiotropic mechanisms. The results disclosed herein indicate that NO₂-OA decreases the proliferation of TNBC cells, especially when co-administered with clinically-relevant DNA-directed therapeutics strategies (FIGS. 1A-1K). NO₂-OA also amplified the induction of DSB through IR or I-SceI DNA cleavage by limiting IR-induced nuclear RAD51 foci formation and DNA recombination, specifically via inhibiting HR and not NHEJ (FIGS. 2A-2D). The functionally-significant Cys319 of RAD51 was targeted by NO₂-OA, but not non-electrophilic native and nitroalkane-substituted control fatty acids (FIGS. 3A-3I). Cys319 alkylation by NO₂-OA disrupted RAD51 dimerization with ABL and decreased ABL-induced phosphorylation of RAD51 Tyr315 (FIGS. 3A-3I). NO₂-OA target proteins beyond RAD51 may additionally play a role in inhibition of HR. The reduction of RAD51 foci and induction of gamma H2AX staining (marker for DNA DSB breaks) by NO₂-OA is cancer cell selective, as it is not occurring in irradiated benign (non-tumorigenic) breast epithelial cells MCF-10A (FIG. 1J)

The potent anti-proliferative effect of olaparib, when administered in combination with NO₂-OA in TNBC cell lines, indicates the pharmacological induction of a BRCA-ness phenotype by NO₂-OA (FIGS. 1A-1K). Suppression of HR-mediated DNA DSB repair by NO₂-OA is specific for cancer cells and reflective of loss of function mutations in BRCA genes, which cause deficits in DNA repair capacity via impairment of HR. Breast cancer patients harboring BRCA1 loss of function mutations may also benefit from suppression of RAD51, as increased expression of RAD51 bypasses BRCA1 function and is a common feature of BRCA1-deficient breast tumors.

While functional HR is important for maintaining genome stability, an enhancement of homology-directed DNA repair activities impedes chemotherapeutic and ionizing radiation treatments for cancer. The elevated expression of RAD51 is positively correlated with breast cancer tumor grade and has been identified in several TNBC cell lines and metastatic patient samples. Several studies have attempted to harness RAD51 inhibition in order to promote lethality in cancer cells. Inhibition of RAD51 with small molecule inhibitors can sensitize cancer cells to chemotherapeutics or IR [e.g., DIDS, B02, RI-1 and IBR2]. For example, RI-1 was identified in a high-throughput screen to potentiate RAD51 filament formation and HR activity, fortuitously adducting Cys319. Unfortunately, RI-1 has multiple electrophilic centers in a complex biphenolic morpholino structure, thus inducing irreversible Michael addition and an incompatibility for in vivo applications due to toxicity.

The RAD51 Cys319 represents an important functional site within the RAD51 protein. Homomultimeric RAD51 filaments interface surrounding the Cys319 residue, which is located within a Src homology 3 (SH3) domain and nearby an ATPase domain (PDB: 1NOW). Posttranslational thiol modification or pharmacological targeting of Cys319 may thus disrupt RAD51 function through multiple mechanisms.

We now identify herein a specific target of electrophilic nitroalkenes, the Cys319 of RAD51, that upon alkylation inhibits RAD51 binding to ssDNA (FIGS. 3A-3I). Thus, the administration of synthetic homologs of endogenously-occurring fatty acid nitroalkenes offers a viable option for inactivating RAD51. The clinical administration of intravenous and oral formulations of $NO_2$-OA (IV IND, 122583; oral IND, 124524) is safe, having cleared multiple Phase I and drug-drug interaction studies, with an oral formulation now in multi-center Phase II trials for treating chronic inflammatory-related diseases.

Nitroalkene fatty acids possess anticancer pleiotropy that affects also other DNA DSB repair pathways besides HDR. A comparison of all 4 pathways repairing DNA DSBs showed that besides HDR, $NO_2$-OA also inhibits single strand annealing (SSA) a conserved DNA DSB repair pathway that is specific to homologous repeats and leads to deletion of sequences between repeats (FIGS. 14A and 14B). This supports other protein Cys as targets of nitrated fatty acids (NFA) within or upstream of SSA. In vivo combination therapy of $NO_2$-OA together with the PARPi talazuparib shows significant greater tumor reduction compared to talazoparib or $NO_2$-OA alone (FIG. 15) in a TNBC xenograft model (MDA-MB-231 cells).

The results disclosed herein indicate that exogenously-administered nitroalkene fatty acids play a role in modulating DNA repair and other signaling responses that can improve treatment of drug-resistant cancers.

In certain embodiments, the compounds disclosed herein inhibit cell migration and invasion. Invasion is a prerequisite for cancer cell spreading and metastasis.

In certain embodiments, inhibition of Rad51-mediated DNA repair by electrophilic nitroalkene fatty acids renders TNBC cells more sensitive to PARP inhibition, killing and potentially invasion and metastasis. About 15% of all breast cancers (BCs) are triple negative, being devoid of the three receptors that classify and define treatment strategies for most BCs: estrogen receptor (ER), progesterone receptor (PR) and ERB2 (also known as HER2). Thus, TNBC is an aggressive type of BC, has no targeted therapies and disproportionally affects younger women and those having African origins. Up to 20% of TNBC patients also carry a germline BRCA1 or BRCA2 mutation (gBRCAm), resulting in defects in homologous-directed DNA repair (HDR). Because of successful Phase 3 clinical trials signifying the advantage of PARPi monotherapy, as compared to chemotherapy for germline BRCA-mutant TNBC patients, olaparib and talazoparib are FDA approved for metastatic gBRCAm positive TNBC patients. These findings reinforce the concept that genetic defects in HDR pave a path to PARPi cancer cell killing, by inhibiting single strand DNA repair and underscore the significance of the co-administration approaches disclosed herein that chemically induce HDR-deficiency by inhibiting Rad51 and amplifying PARPi efficacy. Thus, the 80% of TNBC patients that are negative for gBRCAm and inconsistent in responses to PARPi, despite BRCA-like phenotypes (BRCAness), can then benefit from PARPi therapies. In particular:

i) By chemically-inducing Rad51 inhibition and limiting TNBC cell HDR, patient cohorts eligible for PARPi treatment can now also include those wild type for BRCA or having mutations in other HDR-related genes;

ii) Several cancers, including TNBC, have increased Rad51 expression. Preclinical models indicate that depletion of Rad51 by siRNA and shRNA sensitizes to a) PARPi, b) radiation treatment of pancreatic cancer and multiple myeloma, c) chemotherapy of non-small cell lung cancer (NSCLC) and glioma and d) the reduction of primary tumor growth and brain metastasis in murine TNBC models. The drug targeting of Rad51 is a coveted anti-cancer therapy, but to date no small molecule Rad51 inhibitors have been safe enough for entry into Phase 1/2 development;

iii) PARPi resistance is a problem for patients, a result of cancer cell restoration of BRCA1 or BRCA2 open reading frames, increased use of non-homologous end joining (NHEJ) for repair and Rad51 over-expression. The low toxicity and encouraging success of PARPi, along with data showing that co-treatment with PARPi and a nitroalkene fatty acid profoundly increases PARPi efficacy, offers a new opportunity for limiting drug resistance and enhancing TNBC cell killing In certain embodiments, cancer cell growth, and/or migration and/or invasion are suppressed by treatment with at least one of the nitroalkene fatty acids disclosed herein through modulation of NF-κB signaling. One embodiment contemplates administering to a subject having, suspected of having, at risk of developing, in treatment for, or in remission of, triple negative breast cancer a therapeutically effective amount of a nitroalkene fatty acid. For example, triple negative breast cancer cell growth, migration and invasion are suppressed by treatment with a nitroalkene fatty acid, particularly the electrophilic (10-nitro-octadeca-9-enoic acid, referred to herein as "$NO_2$-OA") through modulation of NF-κB signaling, while nontumorigenic breast epithelial cells are resistant to the effects of $NO_2$-OA because of more intact mechanisms for maintaining redox homeostasis.

Compared to other breast cancer phenotypes, TNBC is an aggressive subtype with a poor prognosis. Patients are four times more likely to show visceral metastases to the lung, liver and brain within five years after diagnosis. Because TNBC does not respond to endocrine therapy or other more targeted chemotherapeutic agents; DNA damage-inducing strategies such as ionizing radiation, cisplatin and doxorubicin remain mainstay treatments. Adverse systemic responses to DNA-directed chemotherapeutic agents, including cardiac and renal toxicity, limit chemotherapy options because of cytotoxic effects on non-cancerous cells.

NO$_2$-OA inhibited cultured TNBC cell viability, motility and tumor cell proliferation-related signaling reactions to an extent where in vivo tumor growth in MDA-MB-231 xenografted mice was attenuated by oral dosing of NO$_2$-OA. This observation also motivates more detailed dose-timing and dose-response studies of NO$_2$-OA effects on the tumor growth and metastasis of multiple breast cancer phenotypes in preclinical animal models.

Figure 6A:
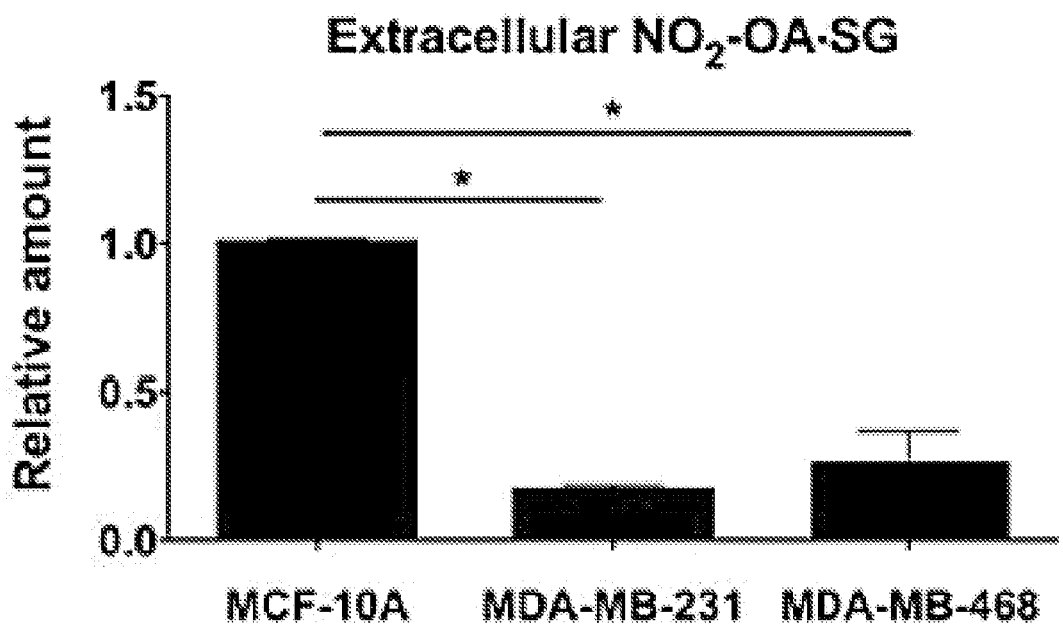

At lower concentrations, there was selective cytotoxicity of NO$_2$-OA towards TNBC cells, compared with non-tumorigenic MCF-10A breast ductal epithelial cells. One significant explanation for this selectivity of action stemmed from the analysis of both basal GSH levels and the formation and fate of NO$_2$-OA-SG adducts in control and TNBC cells. Because of the abundance and reactivity of the GSH thiol, GSH is the primary intracellular reaction target of endogenously-generated and exogenously-administered oxidants and electrophilic species. The rates of MRP1-mediated efflux of GSH-adducted electrophiles from cells contributes to defining the net intracellular concentration, half-life, target protein reactions and cellular and tissue responses to lipid electrophiles. MRP1 was highly expressed in MCF-10A cells compared to TNBC cells, motivating the LC-MS/MS determination of extracellular NO$_2$-OA-SG levels in the media of NO$_2$—OA-treated MCF-10A versus MDA-MB-231 and MDA-MB-468 cells. Consistent with relative extents of MRP1 expression, MCF-10A cells formed and exported 4-5-fold greater amounts of NO$_2$-OA-SG adducts into the extracellular compartment compared with TNBC cells (FIG. 6A). This more extensive export of NO$_2$-OA-SG by MCF-10A, relative to MDA-MB-231 and MDA-MB-468 cells, was also notable because basal GSH concentrations and the GSH:GSSG ratio in MCF-10A cells were more stable after treatment with NO$_2$-OA. In contrast, the GSH concentrations and GSH:GSSG ratio in MDA-MB-231 and MDA-MB-468 cells quickly decreased after treatment with NO$_2$-OA. These results indicate that MRP1 export of NO$_2$-OA-SG and the more sufficient antioxidant capacity of the MCF10A cell line, as opposed to TNBC cells, plays a role in defining the vulnerability of TNBC cells to NO$_2$-OA signaling actions. Another electrophile, 2-cyano-3,12-dioxooleana-1,9-dien-28-oic acid (CDDO), displays antitumor activity by inducing apoptosis in a variety of cancers. CDDO rapidly decreases mitochondrial GSH and induces increased ROS generation in pancreatic cancer cells. In contrast, NO$_2$-OA did not significantly impact cellular rates of H$_2$O$_2$ production after both short term and extended (6 hr) treatment of TNBC cells, indicating that NO$_2$-OA inhibition of TNBC cell growth and viability are not due to induction of ROS.

When the MRP1 transport activity of MCF-10A cells was inhibited by the organic acid probenecid, a more TNBC-like phenotype was conferred in the context of sensitivity to NO$_2$-OA. For example, the impact of NO$_2$-OA on cell growth arrest and killing (FIG. 6CD), cell cycle arrest (cyclin D1, p21) and apoptosis-regulating mediators (PARP-1, caspase-3) all supported the concept that NO$_2$-OA signaling actions are enhanced in MRP1-depleted cells because of more favorable pharmacokinetics in the intracellular compartment. This affirms that the cellular concentrations of GSH, the reaction of GSH with NO$_2$-OA and the subsequent MRP1 export of NO$_2$-OA-SG influence downstream responses to NO$_2$-OA. It is possible that other mechanisms, yet to be described, are also responsible for this differentiation of breast epithelial cell responses.

Figure 8A:
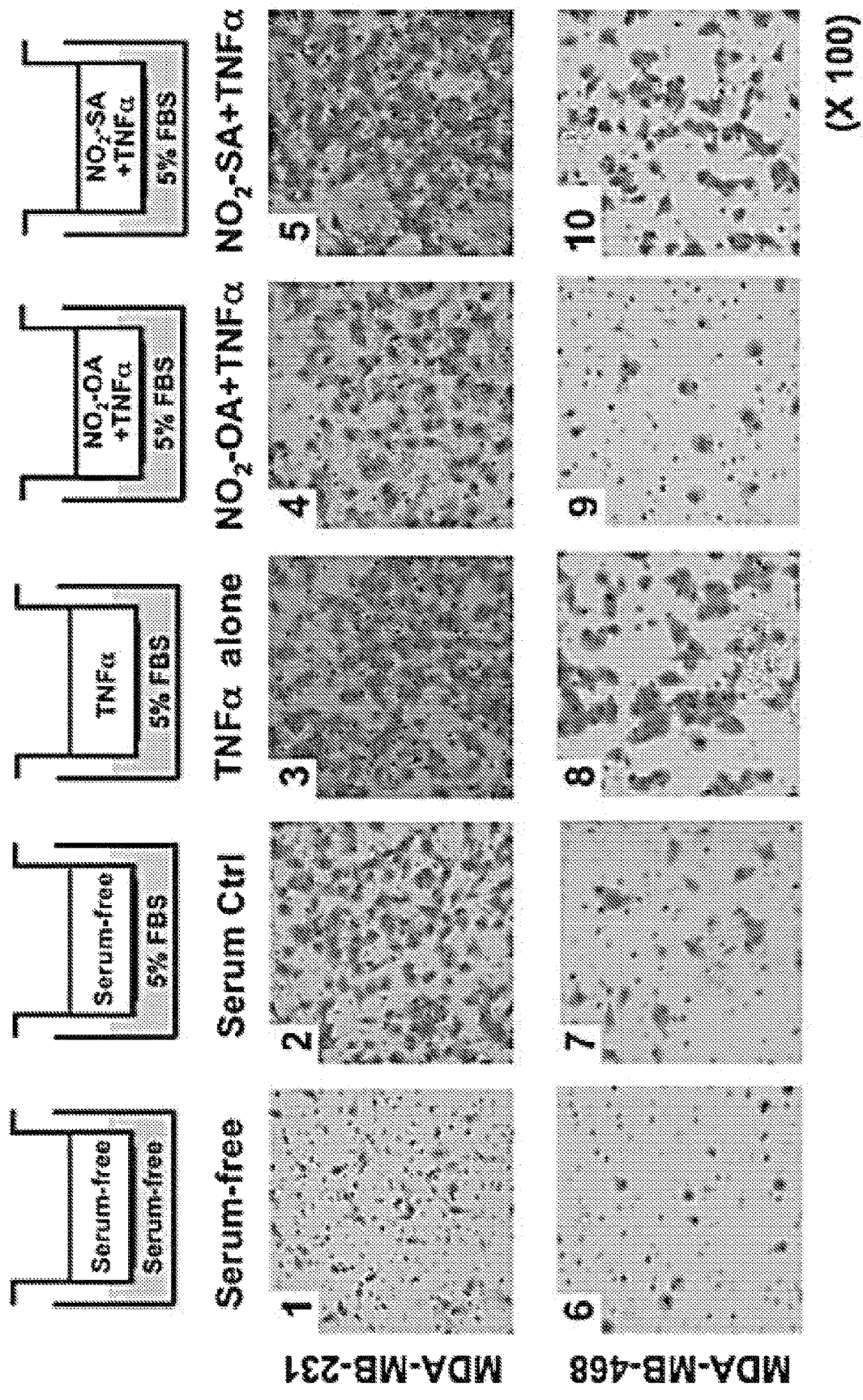
Figure 9A:
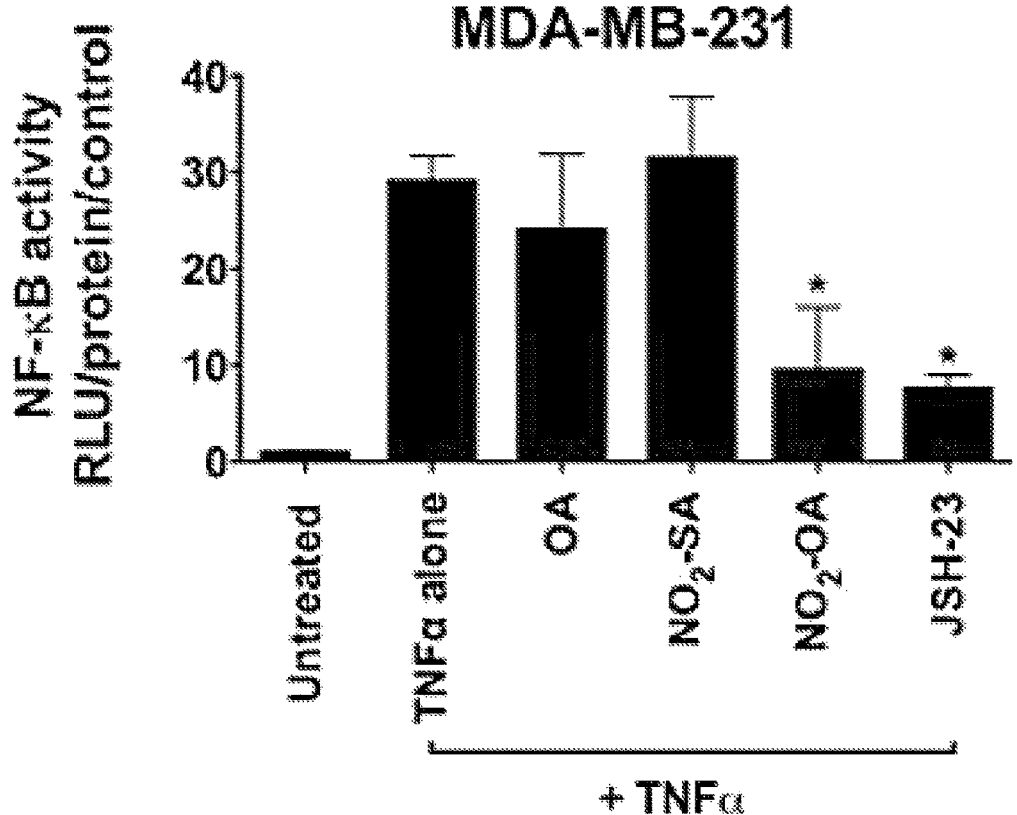
Figure 9B:
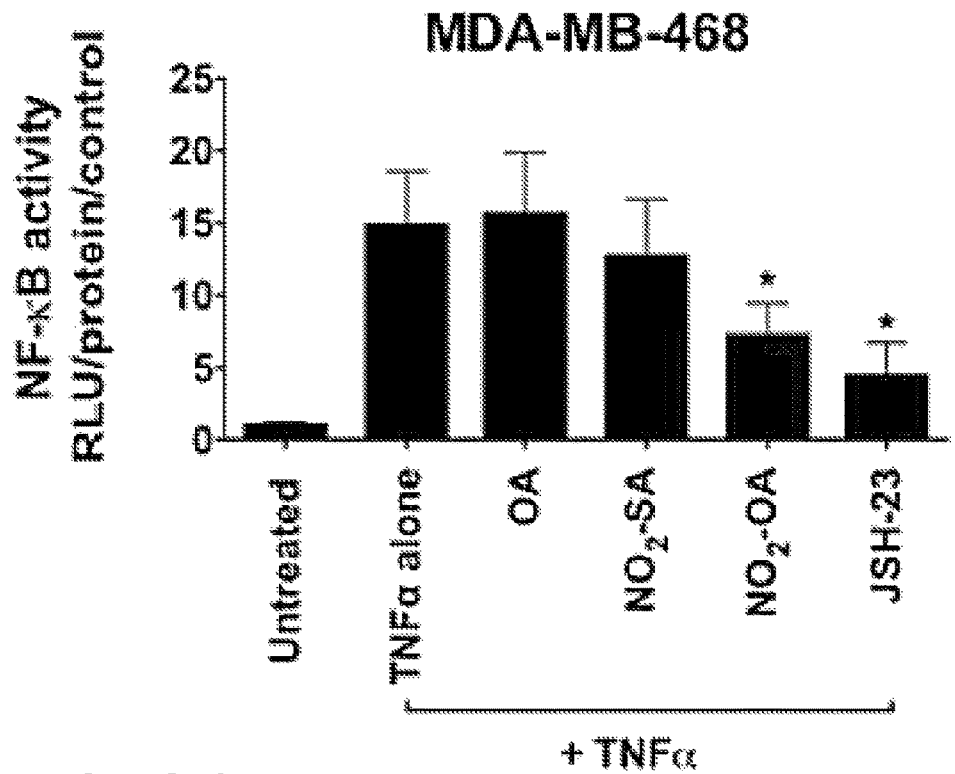
Figure 9C:
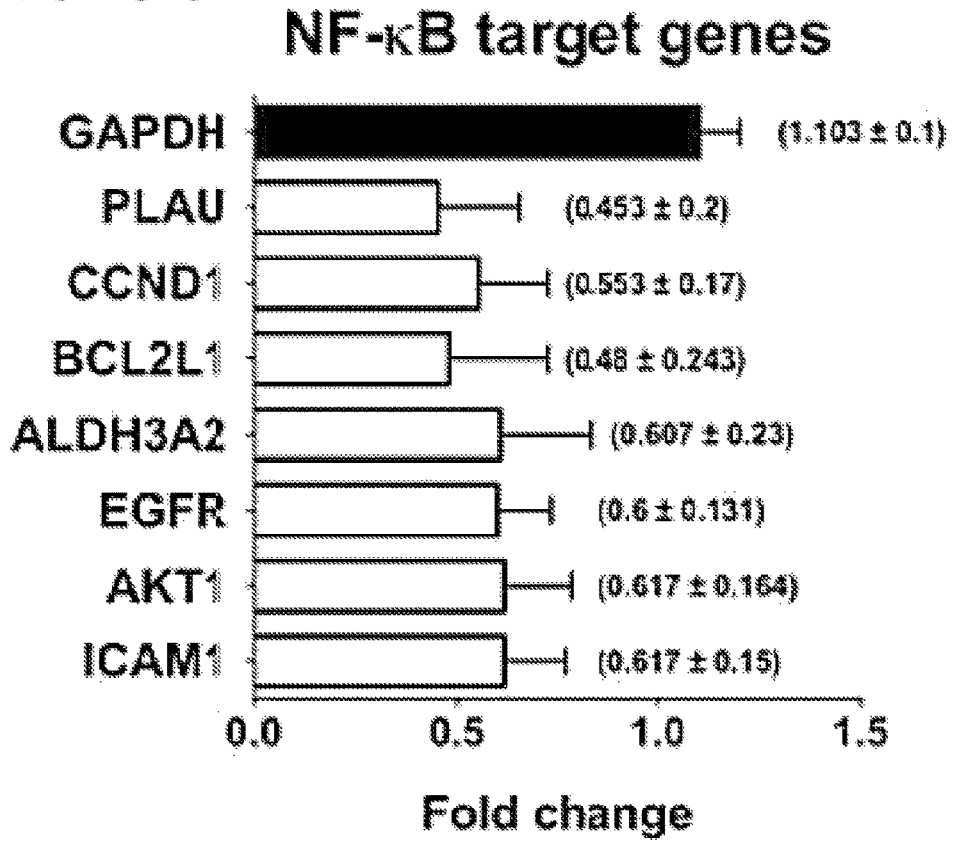
Figure 9D:
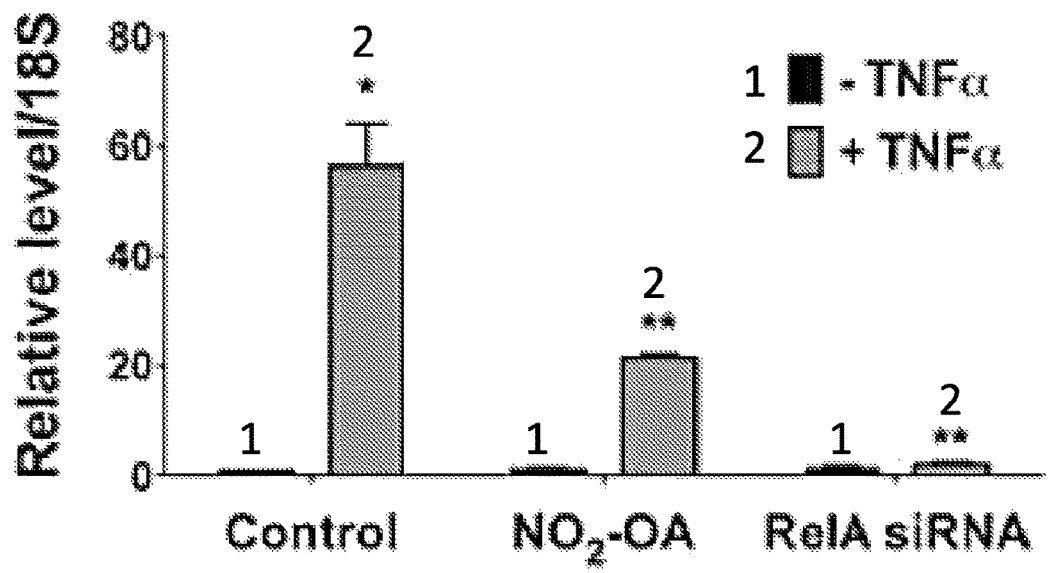

Anti-proliferative actions of NO$_2$-OA on macrophages, vascular smooth muscle cells and fibroblasts are observed in models of chronic vascular and pulmonary disease, but the impact of fatty acid nitroalkenes on cancer cell proliferation had not been considered. This motivated experimental consideration, since there are a limited number of reports suggesting that the upregulation of Nrf2 signaling may result in intrinsic or acquired chemoresistance. In contrast, we observed the in vitro and in vivo inhibition of TNBC growth by NO$_2$-OA (FIG. 4B-E). This growth inhibition of TNBC cells was the result of alterations in signaling responses specific to TNBC cells and not non-transformed MCF-10A cells. Increased p21 and decreased cyclin D1 expression (FIG. 5D) was observed along with an increase in the sub-G1 population of TNBC cells (FIG. 5A-C). Two distinct pathways of apoptotic signaling were engaged by NO$_2$-OA in TNBC cells, initiated by both mitochondrial (caspase-9 activation) and death receptor (caspase-8 activation; FIG. 5F) regulated mechanisms. In aggregate, these data reveal that NO$_2$-OA displays pleiotropic anti-cancer properties via the inhibition of cell proliferation and induction of apoptosis in TNBC. At this point, more detailed mechanisms of NO$_2$—OA-induced apoptotic cell death remain to be defined; however, the electrophilic thiocyanate sulforaphane also decreases Bcl-2 expression, activates cytochrome c release from the mitochondria, and increases FasL expression in TNBC cells. These actions imply that electrophilic fatty acid nitroalkene derivatives might mediate similar actions in the regulation of apoptosis. The inhibition of NF-κB signaling by NO$_2$-OA also limits TNBC cell migration and invasion. Proinflammatory cytokines such as TNFα enhance the metastatic potential of TNBC, with the up-regulation of TNFα expression and activity in TNBC patients strongly linked with tumor metastasis phenotype. TNFα stimulates the expression of epithelial mesenchymal transition (EMT) and chemokine genes via the activation of AP-1 and NF-κB signaling in TNBC cells. Herein, NO$_2$-OA significantly inhibited TNFα-induced TNBC cell migration and invasion (FIG. 6). Decreased expression of the prometastasis genes uPA and ICAM-1, via a decrease in NF-κB transcriptional activity, was also induced by NO$_2$-OA (FIG. 9DE). Consistent with this, electrophilic 15-deoxy-$\Delta^{12,14}$-prostaglandin J$_2$, dithiolethione and dimethyl fumarate also inhibit breast cancer cell migration. NO$_2$-OA also reduced migration of MDA-MB-231 cells in the absence of TNFα induction (FIG. 8B). It is likely that NO$_2$-OA inhibits cell mobility upon reaction with molecular targets in addition to NF-κB, since the electrophilic cyclopentenone 15-deoxy-$\Delta^{12,14}$-prostaglandin J$_2$ also interferes with mammary cancer cell migration via inhibition of F-actin reorganization and focal adhesion disassembly.

The proteolytic degradation of NF-κB subunits contribute to the termination of NF-κB activation. RelA protein is regulated by ubiquitinand proteasome-dependent degradation signals that terminate NF-κB activation. Thiolalkylating and S-nitrosating agents also promote the degradation of the NF-κB subunit p50 via posttranslational modification of Cys62 in HT29 and HCT116 tumor cell lines. Thus, the NO$_2$-OA alkylation of NF-κB RelA induces functional responses similar to other alkylating agents. Notably, the alkylation of RelA by NO$_2$-OA induced an increase in RelA ubiquitination in TNBC cells, an effect not observed for non-electrophilic NO$_2$—SA (FIG. 10D). Peroxisome proliferator activated receptor-γ (PPARγ) acts as an E3 ubiquitin ligase, inducing RelA protein ubiquitination and degradation via physically interacting with RelA protein. The PPARγ ligands troglitazone and pioglitazone increase PPARγ E3 ligase activity by promoting its interaction with RelA protein, in turn, decreasing RelA half-life. Because NO$_2$-OA is a partial agonist of PPARγ, one can speculate that $NO_2$-OA also activates PPARγ E3 ligase activity, thus further destabilizing RelA protein in TNBC.

The inhibition of NF-κB signaling represents a viable anticancer strategy, especially since the aberrant activation of NF-κB is closely linked with the development of diverse human cancers. The immunomodulatory electrophile dimethyl fumarate, FDA-approved as an oral drug for treating multiple sclerosis, also inhibits NF-κB activity in breast cancer cells and inhibits TNBC cell proliferation. The present results, in which $NO_2$-OA inhibited multiple TNBC cell functions: proliferation, survival, mobility and invasion, imply that electrophilic lipid nitroalkene species may also have utility as chemotherapeutic agents.

The lipid electrophile $NO_2$-OA impacts NF-κB signaling in TNBC at multiple levels, including the suppression of IKKβ phosphorylation, inhibition of IκBα degradation and enhanced ubiquitination and proteasomal degradation of RelA. These actions in turn contribute to the inhibition of TNBC cell migration and invasion in vitro. TNBC cells are in part more sensitive to $NO_2$-OA due to lower GSH concentrations and suppression of $NO_2$-OA export as the $NO_2$-OA-SG adduct, a consequence of lower MRP1 expression. This GSH-insufficient redox vulnerability of TNBC cells promotes more extensive protein thiol alkylation and oxidation reactions and instigates chemotherapeutic signaling responses at lower electrophile concentrations. The concentrations of endogenous free, non-protein adducted $NO_2$—FAs in healthy human plasma and urine are typically 1-5 nM. The oral administration of $NO_2$-OA increased murine tumor $NO_2$-OA levels to an extent sufficient to induce pharmacological responses, as evidenced by inhibition of MDA-MB-231 xenograft tumor growth.

In some embodiments, the methods disclosed herein involve administering to a subject in need of treatment a pharmaceutical composition, for example a composition that includes a pharmaceutically acceptable carrier and a therapeutically effective amount of one or more of the compounds disclosed herein. The compounds may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The compounds are preferably formulated into suitable pharmaceutical preparations such as tablets, capsules, or elixirs for oral administration or in sterile solutions, emulsions or suspensions for parenteral or topical administration or inhalation. Typically, the compounds described above are formulated into pharmaceutical compositions using techniques and procedures well known in the art.

In some embodiments, one or more of the disclosed compounds (including compounds linked to a detectable label or cargo moiety) are mixed or combined with a suitable pharmaceutically acceptable carrier to prepare a pharmaceutical composition. Pharmaceutical carriers or vehicles suitable for administration of the compounds provided herein include any such carriers known to be suitable for the particular mode of administration. Remington: The Science and Practice of Pharmacy, The University of the Sciences in Philadelphia, Editor, Lippincott, Williams, & Wilkins, Philadelphia, PA, 21' Edition (2005), describes exemplary compositions and formulations suitable for pharmaceutical delivery of the compounds disclosed herein. In addition, the compounds may be formulated as the sole pharmaceutically active ingredient in the composition or may be combined with other active ingredients.

Upon mixing or addition of the compound(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the compounds exhibit insufficient solubility, methods for solubilizing may be used. Such methods are known and include, but are not limited to, using co-solvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions. The disclosed compounds may also be prepared with carriers that protect them against rapid elimination from the body, such as time-release formulations or coatings. Such carriers include controlled release formulations, such as, but not limited to, microencapsulated delivery systems. Formulations may also be obtained by dissolution with mid and long chain natural oils.

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed compound and a second therapeutic agent (such as an anti-retroviral agent) for co-administration. The compound and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

The active compound is included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems for the treated disorder. In some examples, a therapeutically effective amount of the compound is an amount that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 0.1 mg to 1000 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. In additional examples, the compounds can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

It should be apparent to one skilled in the art that the exact dosage and frequency of administration will depend on the particular compounds administered, the particular condition being treated, the severity of the condition being treated, the age, weight, general physical condition of the particular subject, and other medication the individual may be taking as is well known to administering physicians or other clinicians who are skilled in therapy of retroviral infections, diseases, and associated disorders.

Examples

EXPERIMENTAL PROCEDURES—Nitroalkene fatty acids impair RAD51 function and potentiate the effects of DNA-damaging agents on growth of triple-negative breast cells Cell Culture and Reagents.

HEK 293T, MDA-MB-231, MDA-MB-468, Hs578T and BT-549 cells (American Type Culture Collection) were cultured at 37° C. with 5% $CO_2$ in Dulbecco's modified Eagle's medium containing (DMEM) (Gibco) supplemented with 5% FBS (HyClone), 100 units/ml penicillin, 100 mg/ml streptomycin (Gibco), non-essential amino acids (Gibco) and 2 mM 1-glutamine (Gibco). Doxorubicin (Selleckchem), cisplatin (Sigma) or olaparib (Selleckchem) were dissolved in DMSO or DMF (cisplatin). Nitro-oleic acid (10-octadeca-9-enoic acid) ($NO_2$-OA) and biotinylated $NO_2$-OA were synthesized as previously described. Pure $NO_2$-OA was diluted in DMSO and added to cells after solvation in assay media. Relative cell numbers were compared by measuring the luminescent signal generated by ATP using the CellTiter-Glo (Promega) assay. Cells were plated in a 96-well plate at 5,000 (MDA-MB-231) or 6,600 (BT549 or Hs578T) cells per well. Cells were treated with doxorubicin, cisplatin, or olaparib at the indicated concentrations for 72 h in the presence or absence of 2 μM $NO_2$-OA, which was replenished every 24 h.

$NO_2$—OA In Vivo.

Animals used for this study were approved by and conducted according to the guidelines of the University of Pittsburgh IACUC. MDA-MB-231 cells (0.5×106) were injected into the mammary fat pad (left 4th gland) of 6-wk-old female nude mice in a volume of 20 μL sterile saline. When tumors reached an average volume of 100 mm$^3$, mice were treated with OA+vehicle (n=8), OA-$NO_2$+vehicle (n=7), OA+talazoparib (0.3 mg/kg) (n=10) or OA-$NO_2$ (15 mg/kg)+talazoparib (n=11). Tumor volume was measured by caliper over time in P-values: *<0.01, *<0.001, **<0.0001. The surgical procedure has been previously described.

Plasmids.

The direct repeat green fluorescent protein (DR-GFP) reporter and I-SceI pCAGGS plasmids were a kind gift from Prof. Maria Jasin. pLVX Neo-RAD51 was cloned by PCR amplification of RAD51 with PCR primers incorporating SpeI (5') and BamHI (3') restrictions sites. The PCR product was then ligated into the corresponding restrictions sites of pLVX-Neo (Clonetech) and transformed into DH5a Max efficiency cells (Invitrogen). pLVX Neo RAD51 cysteine to serine mutant plasmids (137, 312, or 319) were produced using the QuikChange II site-directed mutagenesis kit (Agilent) using pLVX Neo-RAD51 as a template.

DSB Repair Assays.

Measurements of NHEJ, HR, Alt-EJ and SSA assays were performed as previously described. HR activity was measured by counting GFP-positive cells by flow cytometry at the MWRI flow cytometry core using a BD LSRII (BD Biosciences). RAD51 overexpressing cells were generated by stable transfection of pLVX RAD51 IRES Neo and selection with geneticin (Invitrogen).

Kinetic DSB Repair Assays.

U2OS cells were prepared as above, but 5 h following compound treatment, cells were transferred into the Incucyte Zoom (Essen) live-cell imaging automated fluorescence microscope at 37° C. with 5% CO2. Cell confluence and green object count per mm2 were determined using Incucyte Zoom software. Green object count per field was normalized to cell confluency to correct for $NO_2$—OA-induced effects on cell proliferation.

Immunostaining and Imaging.

To analyze RAD51 foci formation, 10,000 cells were plated to CultureWell 16-well chambered cover glass (MID-SCI) coated with poly-L-lysine (Sigma) and incubated overnight in 5% FBS media. Cells were then treated with $NO_2$-OA and irradiated (Gammacell 40 Exactor γ-Irradiator, Best Medical) with 5 Gy and incubated for 6 h. Cells were fixed with 10% formalin for 20 min at 4° C. and immunostained with RAD51 (Santa Cruz) or γH2AX (EMD Biosciences) antibodies. Z-stack images were acquired using a Nikon AIR confocal microscope with 60× oil objective and acquisition performed using NIS elements software. Quantification of z-stacks and foci were completed using ImageJ software.

Cell Cycle Analysis.

Cell cycle analysis was performed with propidium iodide on MDA-MB-231 cells treated with DMSO or 5 μM $NO_2$-OA. Samples were analyzed at the Flow Cytometry Core at MWRI utilizing a BD LSRII (BD).

Western Blotting and Immunoprecipitation.

Cell lysates and immunoprecipitation were prepared. For immunoprecipitation analysis, one million HEK 293T cells were transiently transfected with Fugene 6 (Promega) and 2 μg pQCXIP (EV) or FLAG-RAD51 pQCXIP plasmids and precipitated with Anti-FLAG M2 Affinity Gel (Sigma).

Biotinylated OA-NO2 Affinity Capture of RAD51.

HEK 293T were transiently transfected with Fugene 6 (Promega) and 5 μg RAD51 expressing vectors (wild-type, C312S, or C319S). Cells were treated 24 h later with 5 μM biotin-$NO_2$-OA or biotin-SA-$NO_2$ for 1 h in 5% FBS medium. Cells were prepared as above. Precipitation of biotinylated $NO_2$-OA was accomplished with 8 μl of streptavidin agarose beads with 1 mg total cell lysates incubated for 16 h at 4° C. Detection of RAD51 was accomplished by immunoblot with RAD51 antibody (1:2000) with actin antibody (1:3000) probed as loading control.

Protein Purification for In Vitro RAD51-ABL Binding Assay.

Recombinant His-tagged RAD51 in the pET21a vector were transformed into *E. coli* BL21(DE3)pLysS cells (EMD Millipore) and purified.

DNA Binding Assays.

Reactions were performed in black 96-well plates (Greiner) in 50 μL reaction volumes in 20 mM HEPES pH 7.5, 10 mM MgCl2, 0.25 μM BSA, 2% glycerol, 30 mM NaCl and 4% DMSO. Purified RAD51 protein (Abcam) and OA (negative control) or $NO_2$-OA was pre-incubated for 5 mM at 25° C. 2 mM ATP and 100 nM 5'-Alexa Fluor 488 ssDNA poly-dT (Integrated DNA technologies) were added to the reaction and incubated for 90 min at 37° C. DNA binding was measured using fluorescence polarization (FP) on a Tecan Spark 20M (ex/em 480 nm/535 nm). Compound fluorescence quenching was detected as above in the absence of RAD51 protein.

Molecular Modeling.

Structures for RAD51 (PDB: 1NOW (30) and $NO_2$-OA were aligned using PyMOL 1.7.1. The structure of $NO_2$-OA 2 was generated using ChemDraw 15 (PerkinElmer) and converted to 3D structure using Open Babel version 2.3.1.

Statistical analysis.

Data represent the mean±SEM from 3 independent experiments unless otherwise noted. A p value<0.05 was considered statistically significant. Non-linear curves were generated in GraphPad Prism 7.0 (GraphPad Software, La Jolla, CA, USA) for statistical analysis. EC50 values and standard error were calculated from three independent experiments utilizing a non-linear dose response variable slope model. Significance was tested by one-way ANOVA for multiple groups with Tukey posttest or by t-test when groups were less than three. RAD51 foci number was analyzed with ImageJ. Nuclear boundaries were individually identified in more than 50 cells per treatment group in three independent experiments.

RESULTS—Nitroalkene fatty acids impair RAD51 function and potentiate the effects of DNA-damaging agents on growth of triple-negative breast cells $NO_2$—OA Inhibits TNBC Cell Growth, RAD51 Foci Formation and Sensitivity to Ionizing Radiation.

Figure 1B:
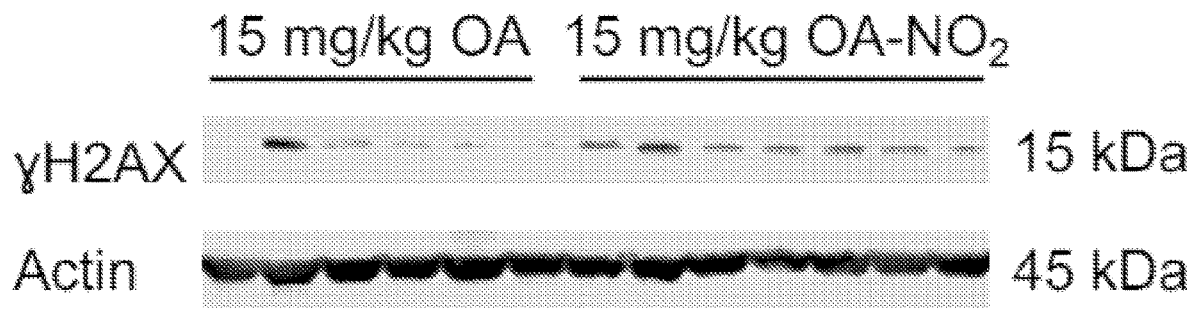

Data indicates that $NO_2$-OA inhibited multiple aspects of TNBC epithelial cell, but not non-tumorigenic breast epithelial cell, NF-κB signaling, by alkylating functionally-significant thiols in a) the inhibitor of NF-κB subunit kinase b (IKK b), thus limiting downstream IκKa phosphorylation and (b) the NF-κB RelA protein, thus preventing DNA binding and promoting RelA polyubiquitination and proteasomal degradation. Whether $NO_2$-OA could also enhance TNBC DNA damage in vivo was also assessed. MDA-MD-231 cells were implanted into the mammary gland of mice and when tumors reached a volume of 100 $mm^3$, mice were treated with 15 mg/kg of the non-electrophilic fatty acid oleic acid (OA) or $NO_2$-OA by gavage for 4 wk. Mice treated with $NO_2$-OA had significantly decreased tumor growth rates when compared to OA treated controls (FIG. 1A). Probing tumor levels of the DNA damage biomarker γH2AX by immunoblotting showed OA-$NO_2$ treated mice displayed higher levels of γH2AX. (FIG. 1B). Densitometric quantification of tumoral γH2AX/β-actin protein levels in OA and $NO_2$-OA treated mice increased γH2AX in $NO_2$-OA treated mice. This response became statistically significant after Grubbs outlier detection and elimination of OA treated mouse #2. The orthotopic tumor in OA mouse #2 was the largest tumor in the study, with necrosis potentially causing enhanced γH2AX levels.

Figure 1C:
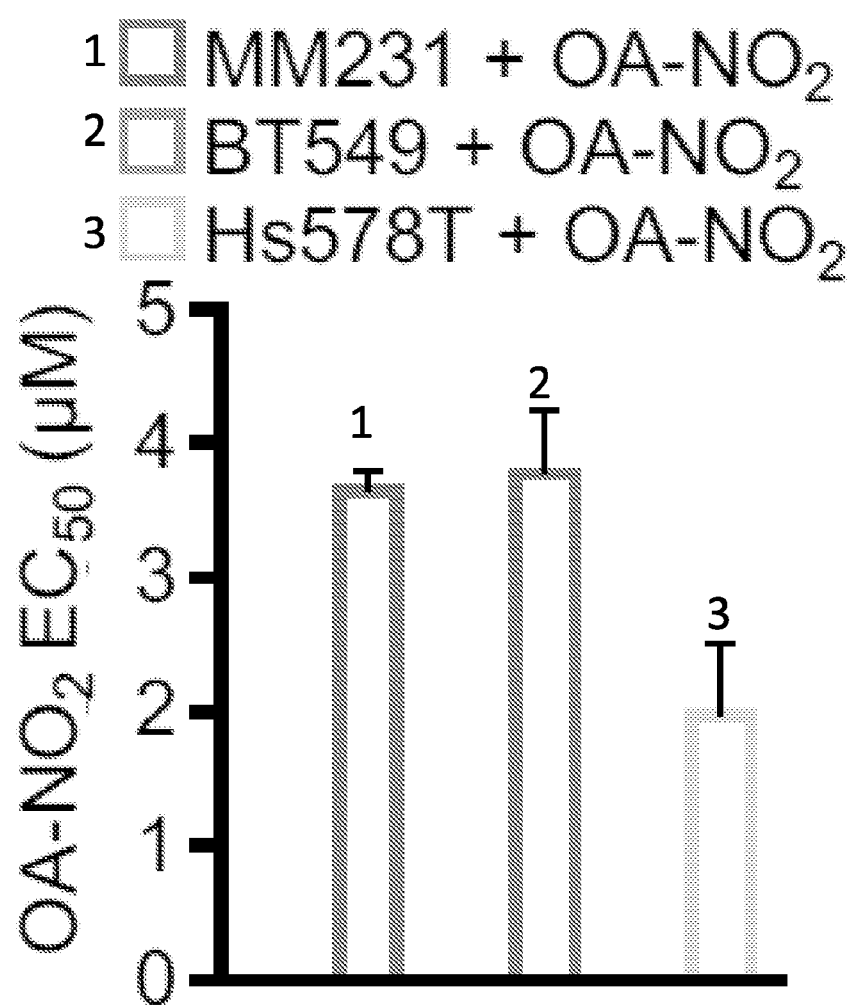
Figure 1D:
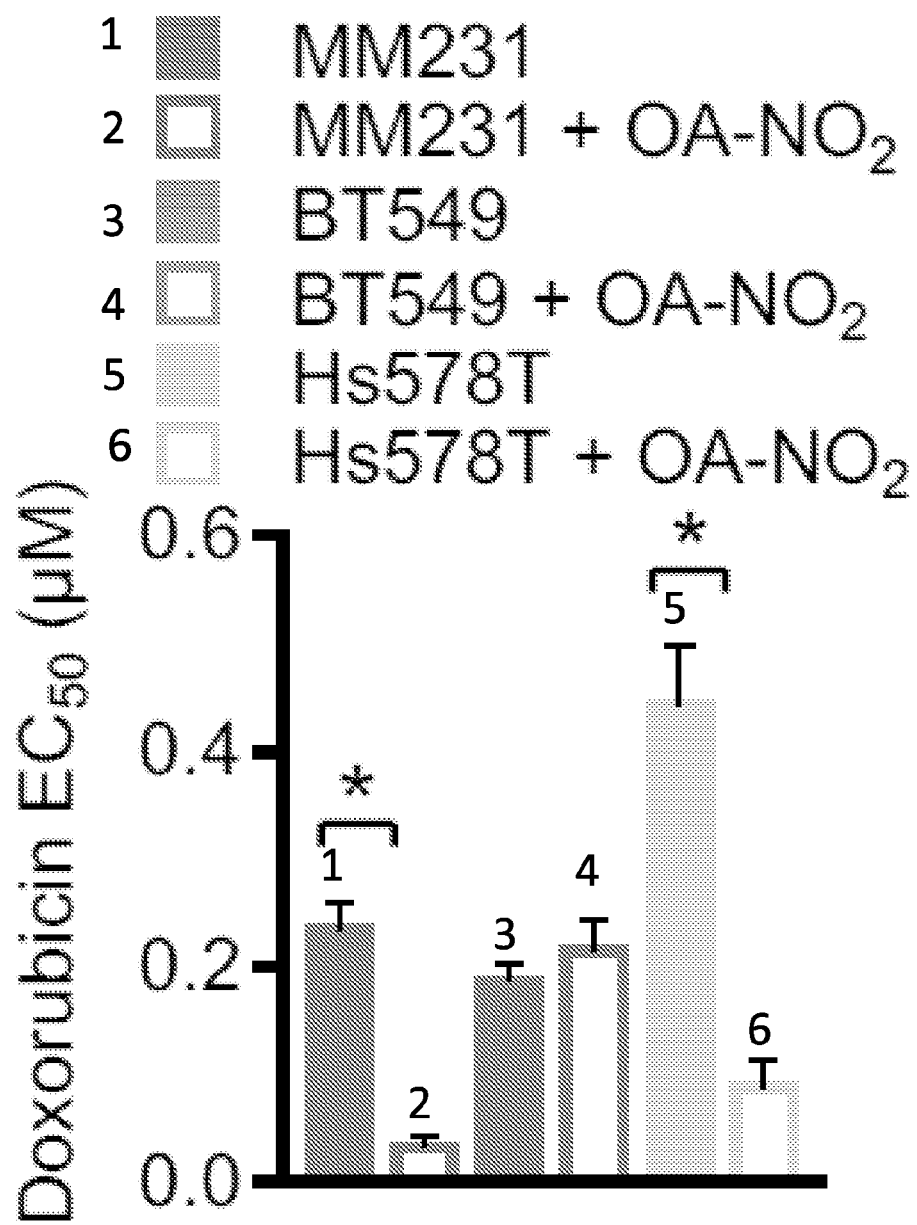
Figure 1F:
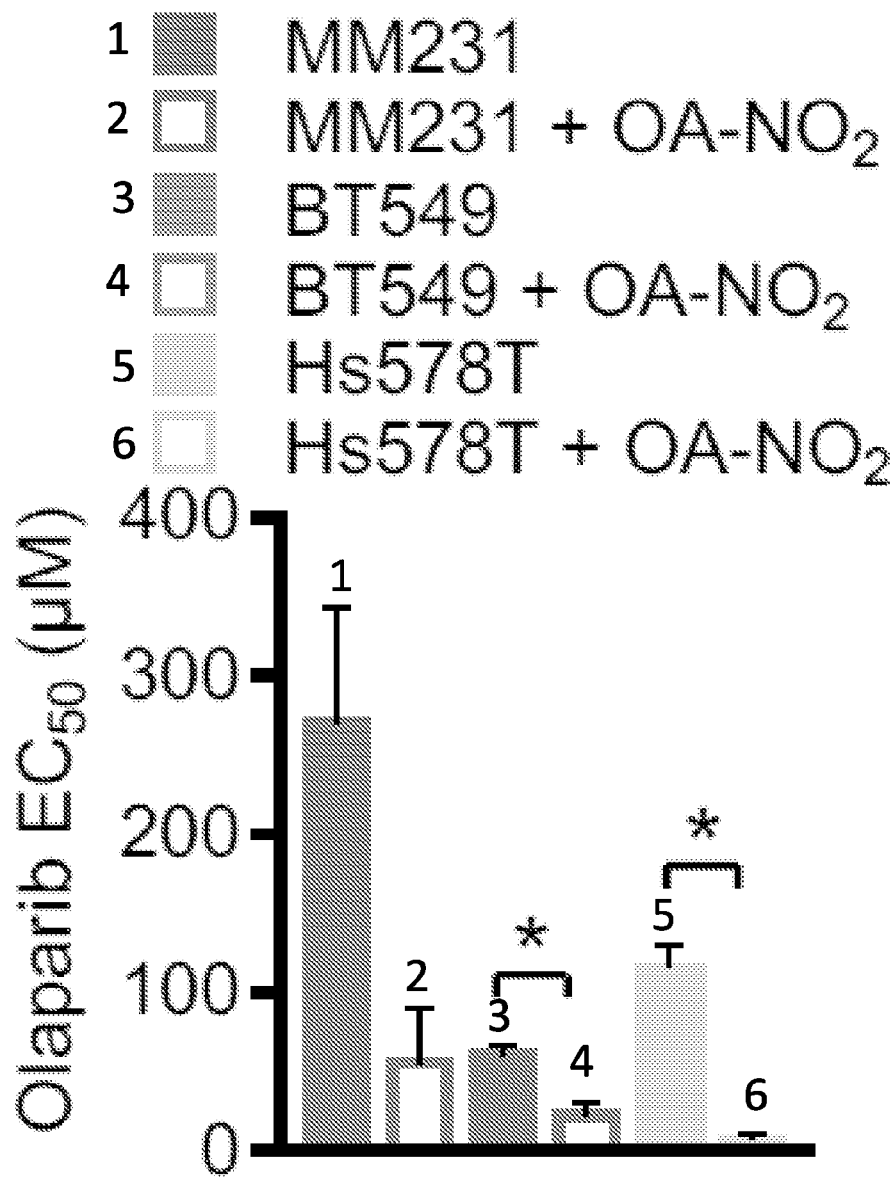
Figure 1G:
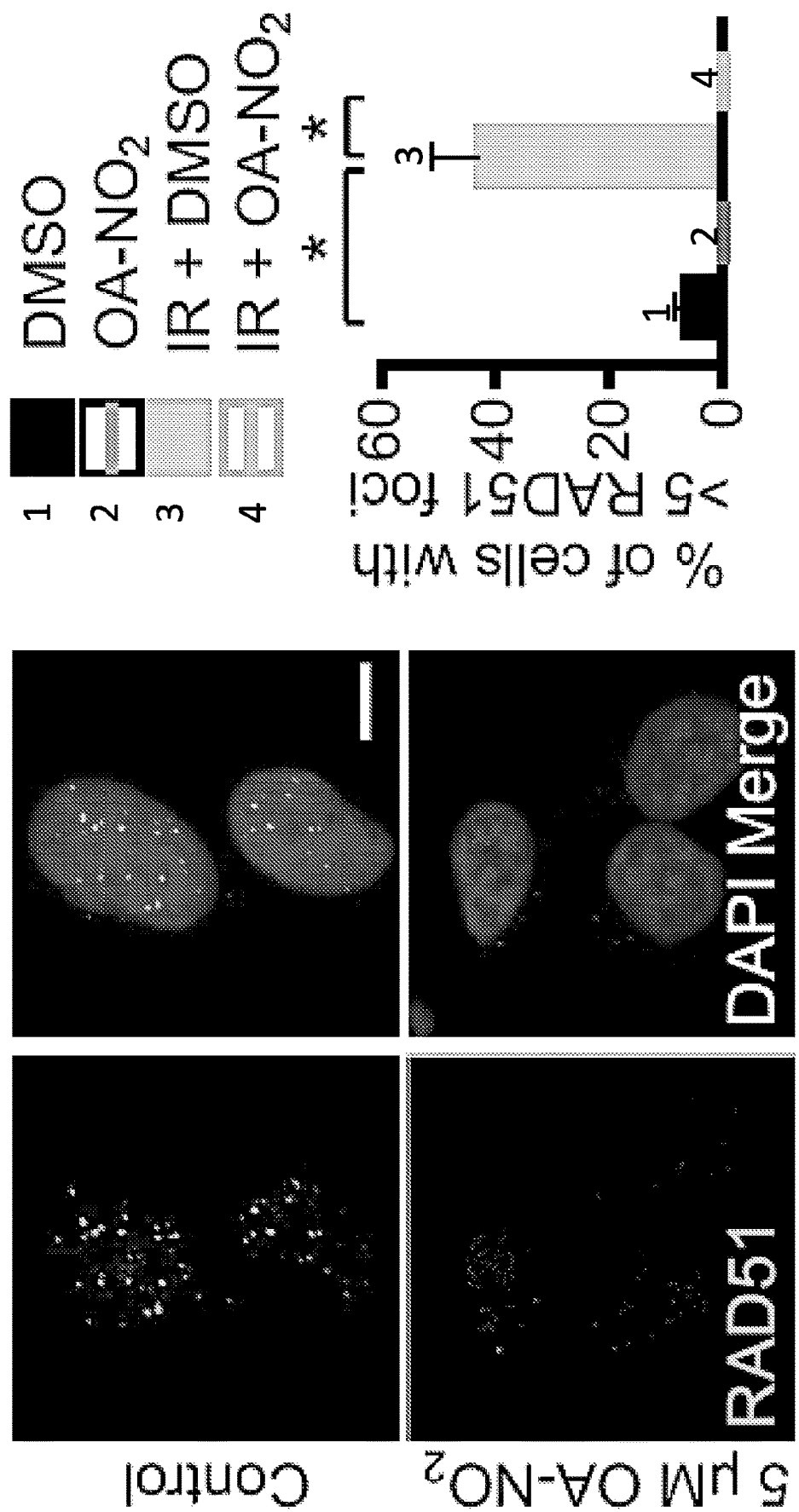

The TNBC growth inhibitory effects of $NO_2$-OA were then evaluated in combination with DNA damaging agents. The cell lines MDA-MB-231, BT-549 and Hs578T were treated with $NO_2$-OA daily for 3 d and relative cell numbers were quantified by measuring the ATP-dependent luminescent signal generated using Ultra-Glo luciferase with the substrate luciferin. The $EC_{50}$ values for growth inhibition of TNBC cells ranged from 1.98±0.52 μM (Hs578T) to 3.78±0.48 μM (BT-549), with MDA-MB-231 cells displaying an EC50 value of 3.66±0.14 μM (FIG. 1C). We next tested the DNA damaging agents doxorubicin and cisplatin in combination with daily treatment with 2 μM $NO_2$-OA. $NO_2$-OA enhanced growth inhibition of doxorubicin in MDA-MB-231 and Hs578T cells, by 7- and 5-fold, respectively (FIG. 1D). The growth of BT-549 cells was not affected. Co-treatment of $NO_2$-OA with cisplatin showed a similar trend for MDA-MB-231 and Hs578T cells, displaying increased growth inhibition by 6- and 3-fold, respectively, while growth inhibition of BT-549 cells were suppressed 1.4-fold (FIG. 1E). A subset of TNBC cells are sensitive to PARP inhibition and display a BRCAness phenotype in the presence of wild-type BRCA1, so the PARP-1 inhibitor olaparib was evaluated to determine if a combination treatment with $NO_2$-OA enhanced potency. MDA-MB-231, Hs578T and BT-549 cells all displayed enhanced growth inhibition when olaparib was combined with $NO_2$-OA by 5-, 17- and 3-fold, respectively (FIG. 1F). To specifically show that combination treatment of olaparib with NO$_2$-OA, but not OA affected proliferation and to evaluate the effect of daily olaparib media exchanges, MDAMB-231 cell proliferation was quantified in dose response assays. Daily administration of olaparib in combination with OA did not significantly alter the EC50 of olaparib in MDA-MB-231 cells. In contrast, olaparib in combination with NO$_2$-OA significantly inhibited growth (FIG. 1G). Next, another PARPi talazoparib was tested in combination with NO$_2$-OA for growth inhibition and determination of a combination index using the Chou-Talalay method. MDA-MB-231 cells were plated in a 96 well plate and treated with talazoparib (0.01-75 µM) plus OA-NO$_2$ or NDA-NO$_2$ (0.2-12 µM) daily for 3 days. Growth inhibition (relative cell numbers) of MDA-MB-231 cells was determined by luminescent detection of ATP (CellTiter-Glo) (FIG. 1K). Growth inhibition was nearly 100% in wells treated with 12 or 6.0 µM NO-OA and 0.01-75 µM of talazoparib (FIG. 1K, upper half). This translated into a robust combination index indicating drug synergism (CI<1) of NO$_2$-OA with talazoparib (FIG. 1K, lower half). Thus, standard TNBC chemotherapeutic drugs as well as targeted PARP-1 inhibition exhibited enhanced anti-proliferative effects in a synergistic, as opposed to an additive effect, when co-administered with NO$_2$-OA in TNBC cells.

Figure 1I:
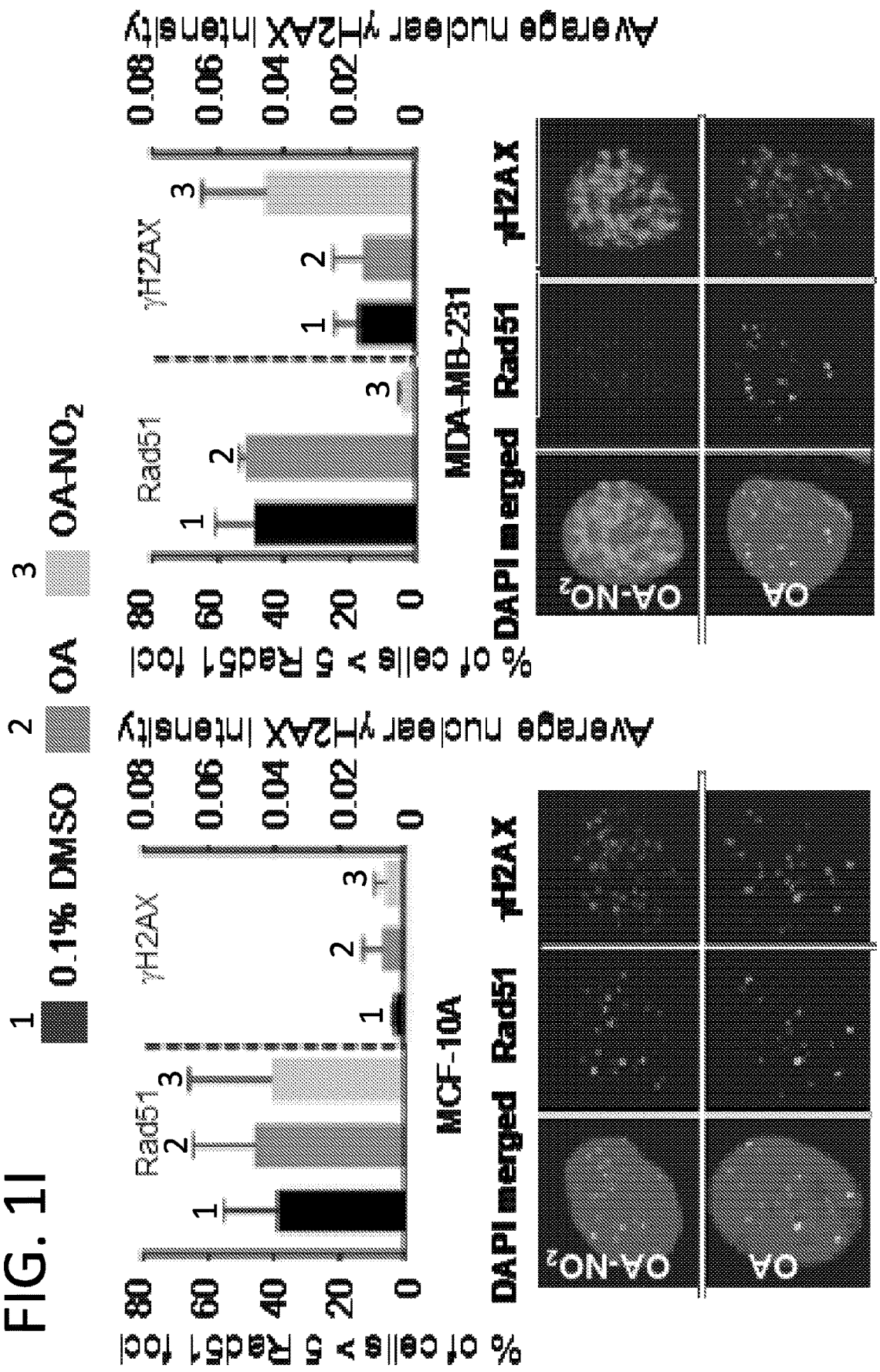

The heightened tumor γH2AX levels in vivo and sensitization of TNBC cells to DNA damaging agents, especially in the context of olaparib-induced responses, led to further exploration of DNA damage repair modulation by NO$_2$-OA. As olaparib sensitivity is a hallmark of HR-deficient cells, it was evaluated whether NO$_2$-OA impacted DNA repair by HR. To specifically probe DNA double-strand break repair, MDA-MB-231 cells were challenged with 5 Gy IR and RAD51 foci were quantified. The treatment of breast cancer cells with NO$_2$-OA inhibited RAD51 foci formation, as reflected by a) the number of cells with more than 5 foci and b) responses of vehicle treated cells following IR (FIG. H). Cell cycle analysis of MDA-MB-231 cells confirmed that no significant changes to the cell cycle occurred, that might indirectly alter RAD51 foci formation. Evaluation of nuclear γH2AX staining to probe for DNA damage of MDA-MB-231 cells in the presence or absence of 5 Gy IR found NO$_2$-OA significantly increased nuclear γH2AX localization in irradiated MDAMB-231 cells compared to vehicle controls indicating increases in DSBs and overall DNA damage (FIG. 1I). Increasing concentrations of NO$_2$-OA also enhanced breast cancer cell death in a clonogenic assay following irradiation with 2 Gy IR. Evaluation of the DNA damaging effects of OA and NO$_2$-OA on non-transformed MCF10A and MDA-MB-231 cells following 5 Gy IR found nuclear γH2AX staining was only increased in TNBC cells treated with NO$_2$-OA2, not MCF10A cells.

NO$_2$—OA Decreases HR, but not NHEJ Efficiency.

Figure 2A:
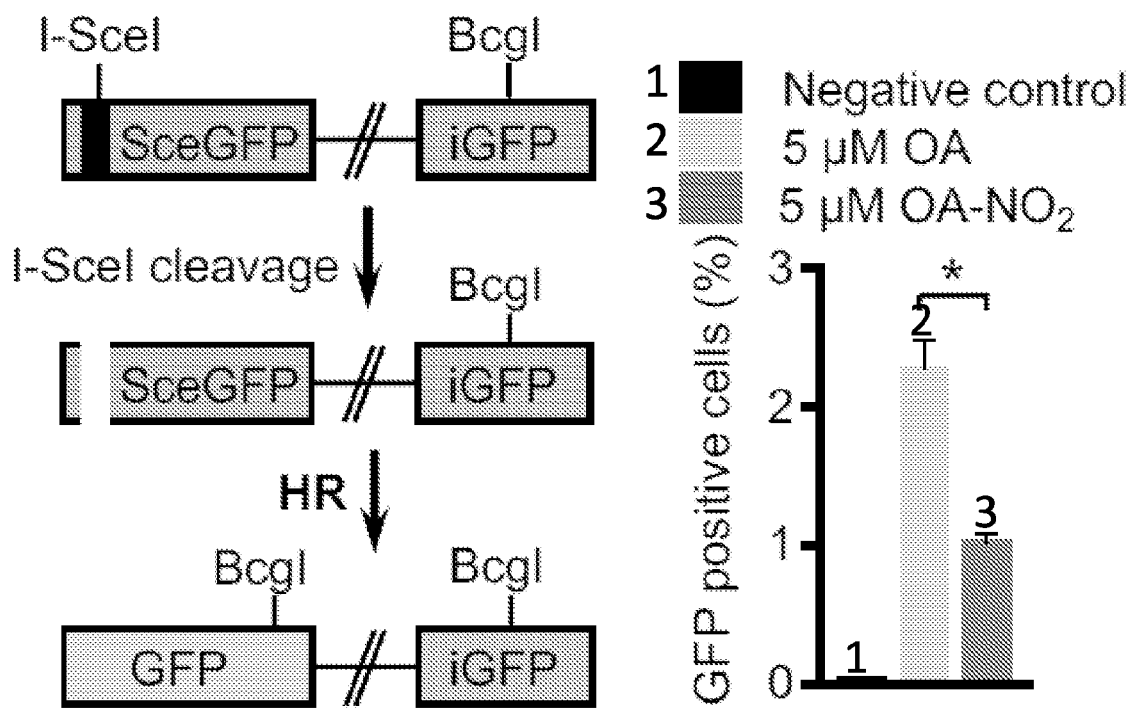
FIGS. 2A-2D. Inhibition of homologous recombination, but not non-homologous end joining by $NO_2$-OA.
Figure 2B:
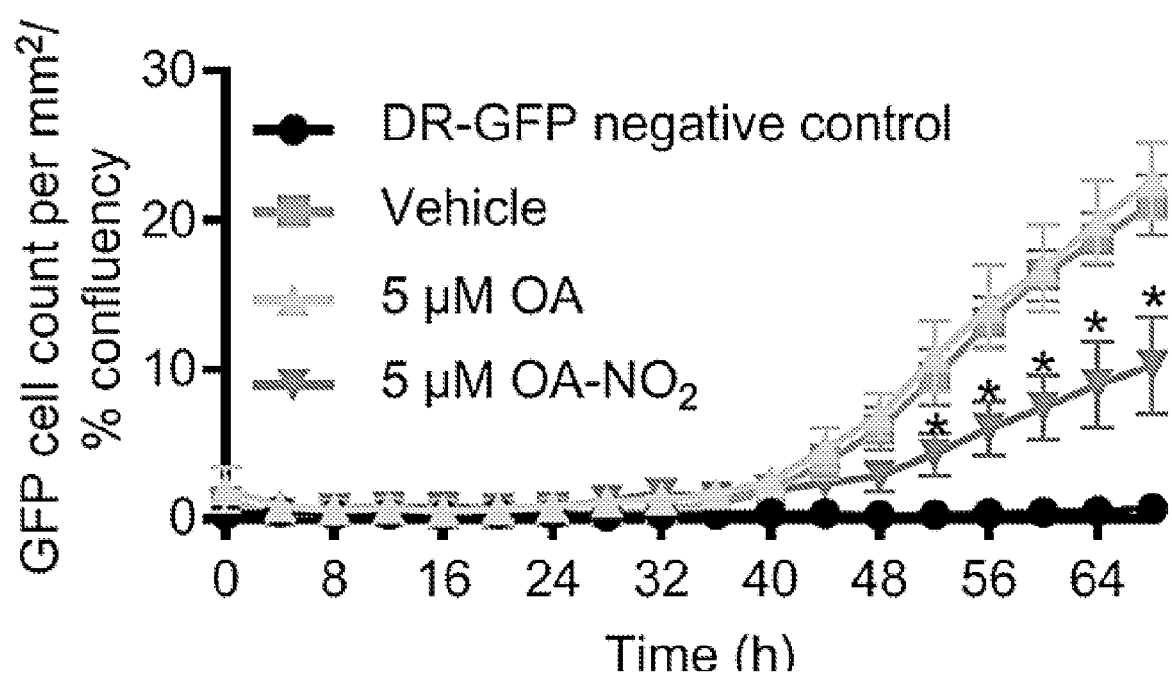
Figure 2C:
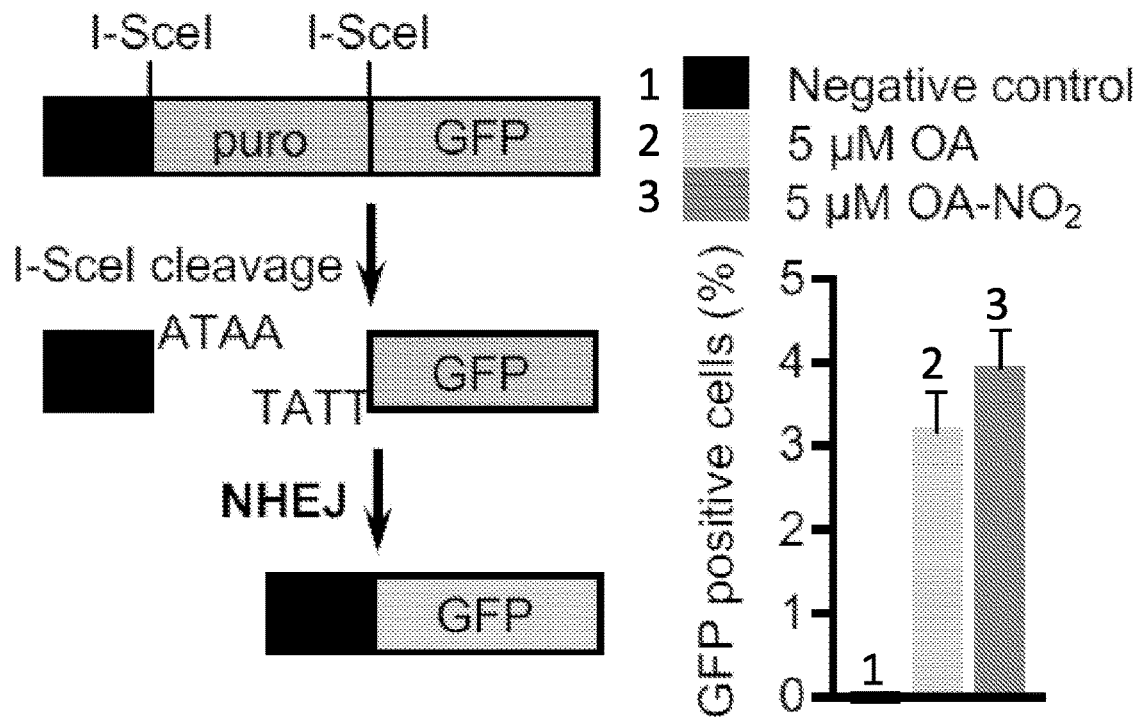
Figure 2D:
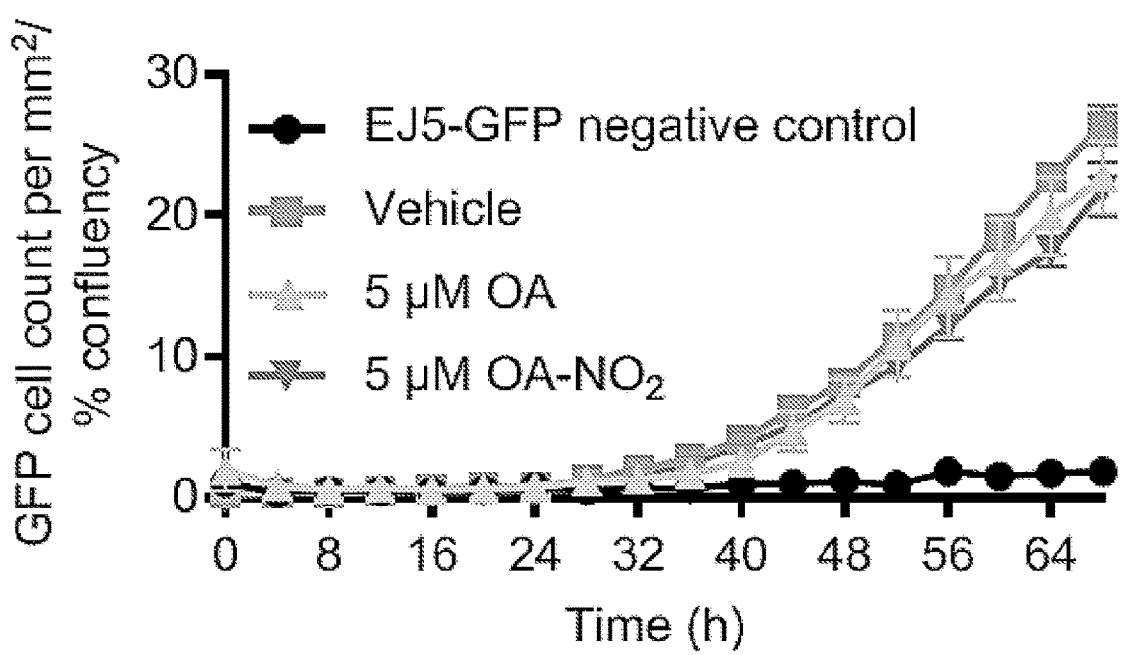

NO$_2$-OA-dependent effects on HR DNA repair were further investigated by utilizing a DRGFP reporter assay. This analysis quantifies intracellular recombination of an integrated cDNA cassette of two tandem non-fluorescent GFP constructs following introduction of an I-SceI cleavage to the system by measuring the fluorescent GFP protein that is produced following successful recombination. Daily NO$_2$-OA treatment of U2OS cells harboring the DR-GFP construct revealed that after I-SceI transfection, the number of GFP positive cells was significantly decreased by 2-fold when compared to native OA or vehicle control after 48 h (FIG. 2A). A novel strategy was used to measure the kinetics of changes in HR in live cells by using automated fluorescence microscopy to track the emergence of GFP positive cells over time in monolayers, as opposed to making static measurements of detached cells using flow cytometry. To account for changes in cell density over time, cell confluency was measured following treatment of DR-GFP U2OS cells with vehicle, 5 µM OA or NO$_2$-OA every 4 h for 3 d. The emergence of GFP positive cells subsequent to I-SceI-induced cleavage was quantified and normalized to cell confluency over time to compare NO$_2$-OA with OA and untreated cells. Daily administration of 5 µM NO$_2$-OA decreased the number of GFP-positive cells by 2-fold over 68 h when compared to controls (FIG. 2B). The impact of NO$_2$-OA on suppression of DSB repair through both the HR and NHEJ pathways was examined by utilizing the EJ5-GFP NHEJ reporter assay, which separates GFP cDNA from a transcriptional promoter with a puro gene flanked by two I-SceI cleavage sites. In contrast to the effects seen by DR-GFP-mediated HR measurements, EJ5-GFP U2OS cells showed no effect of OA-NO$_2$ on NHEJ. This was indicated by an absence of changes in the number of GFP positive cells following I-SceI cleavage after 48 h by flow cytometric analysis or over 68 h by live-cell fluorescence microscopy (FIGS. 2C, 2D).

NO$_2$—OA Targets RAD51 Cys319 and Decreases RAD51 Phosphorylation.

Figure 3A:
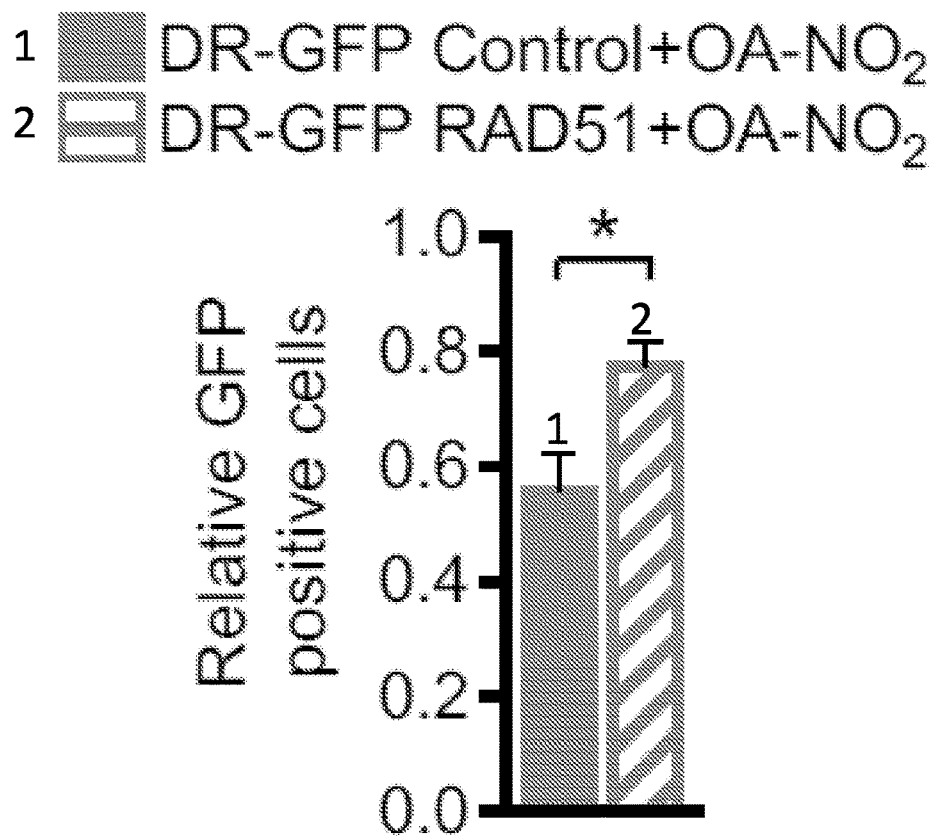
FIGS. 3A-3I. $NO_2$-OA binds covalently to RAD51 at Cys319 and blocks ABL heterodimerization.
Figure 3B:
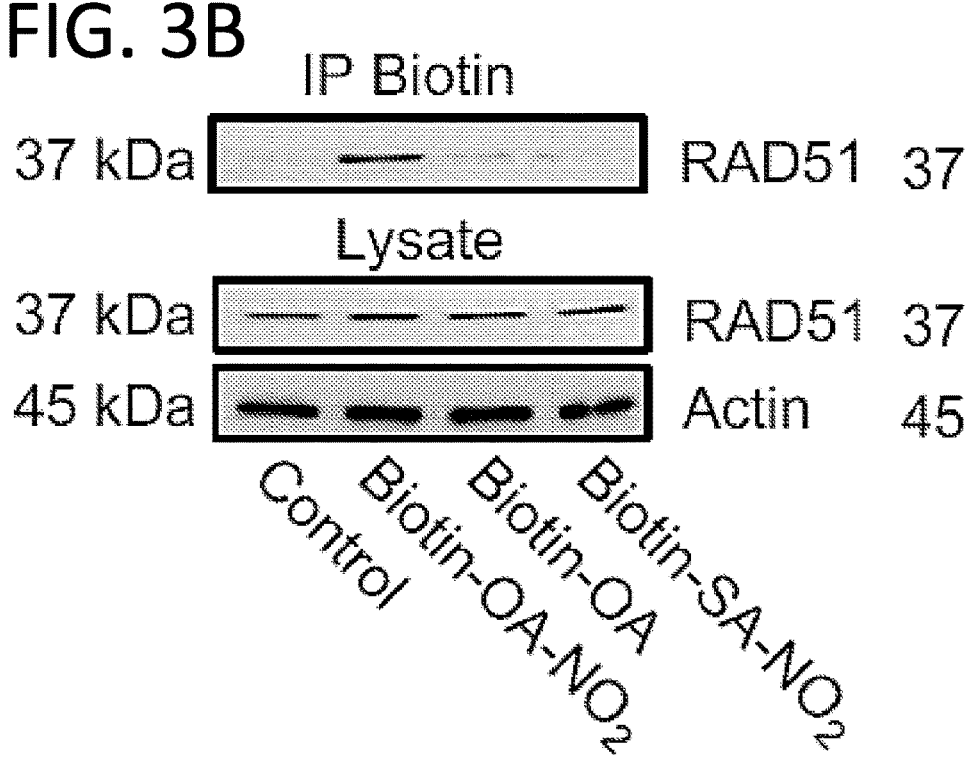
Figure 3C:
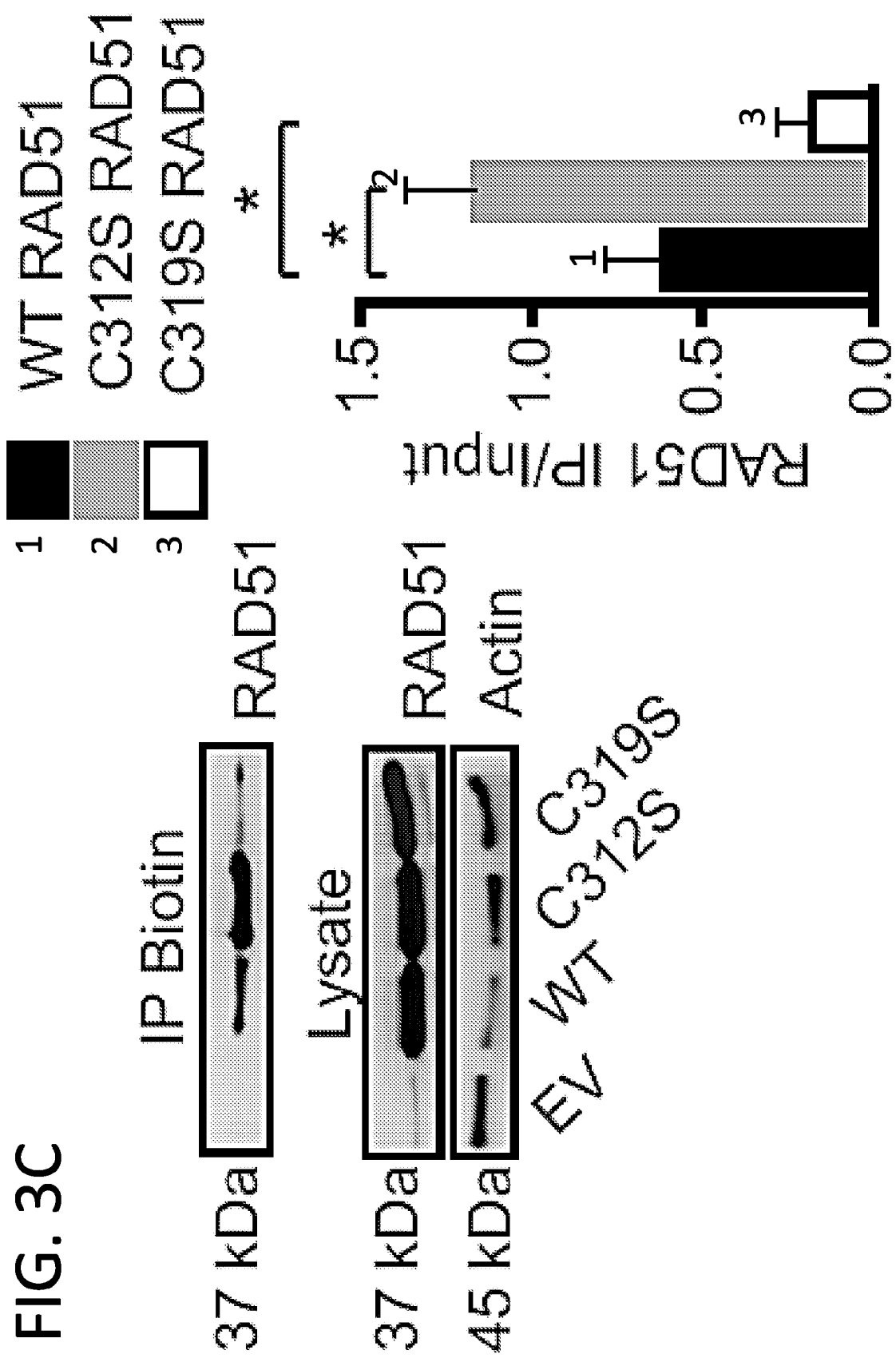
Figure 3D:
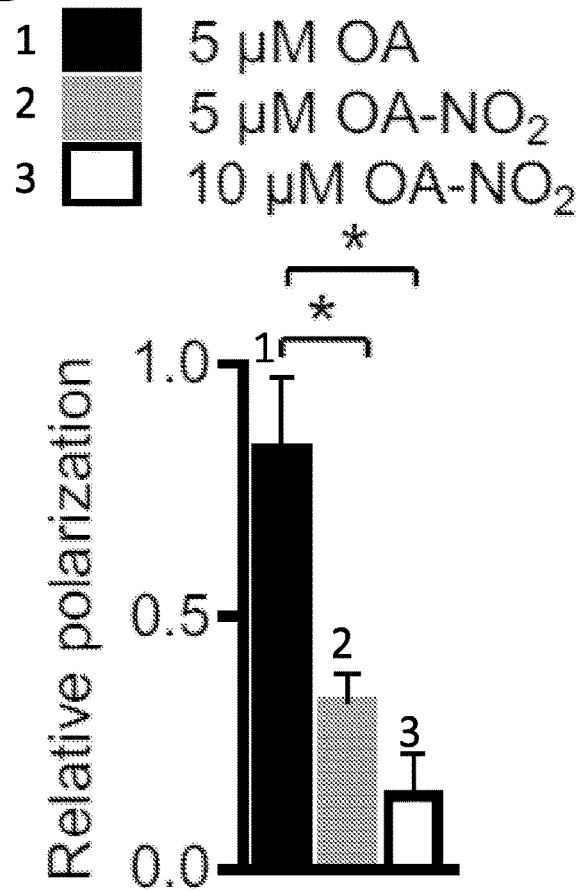
Figure 3E:
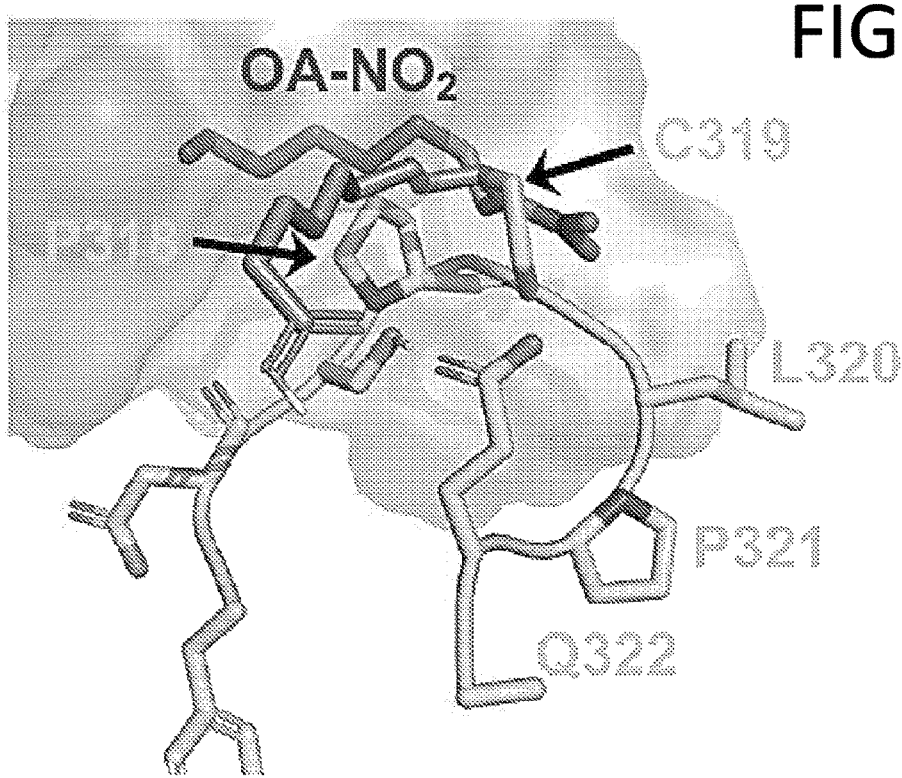

Inhibition of IR-induced RAD51 foci formation and DR-GFP HR reporter functionality by NO$_2$-OA was further studied by testing if overexpression of the critical HR protein RAD51 in the HR reporter cells could rescue the effects of NO$_2$-OA. HR activity, as measured by the percentage of GFP positive cells relative to OA control treatment, was significantly increased in U2OS DR-GFP reporter cells stably overexpressing RAD51 treated with 5 µM NO$_2$-OA in comparison to control reporter cells (FIG. 3A). Protein structural data (PDB: 1NOW) shows Cys319 is a solvent-exposed nucleophile within the RAD51 C-terminus that is susceptible to reaction with RI-1, a reagent also having Michael acceptor qualities. Moreover, fluorophore adduction of Cys319 disrupts RAD51 filament formation in vitro. It was hypothesized that NO$_2$-OA would react with RAD51 Cys319. Indeed, biotin-NO$_2$-OA, but not the non-electrophilic biotin-oleic acid (OA) and biotin-10-nitro-octadecanoic acid (SA-NO$_2$), supported affinity precipitation of RAD51 from cell lysates with streptavidin-labeled beads (FIG. 3B). Comparing RAD51 Cys312Ser or Cys319Ser mutant reaction with biotin-OA-NO$_2$, revealed a preferential reaction of NO$_2$-OA with Cys319 (FIG. 3C). RAD51Cys312Ser and RAD51 WT controls were readily affinity precipitated by biotin-NO$_2$-OA, as opposed to when RAD51Cys319Ser was expressed in mutant cells. Of note, the RAD51Cys312Ser mutant displayed enhanced precipitation of NO$_2$-OA, which may reflect interruption of a disulfide bond between RAD51Cys312 and Cys319 or another intracellular protein that obscures Cys319. The ability of NO$_2$-OA to specifically disrupt RAD51 binding from DNA was probed by quantifying changes in fluorescence polarization of an Alexa Fluor 488 conjugated single-stranded oligonucleotide in vitro. NO$_2$-OA, but not OA, decreased the relative polarization of RAD51 in the presence of ATP and DNA (FIG. 3D). Control experiments found OA and NO$_2$-OA did not cause non-specific effects through fluorophore quenching to decrease fluorescence polarization. Computational analysis revealed that NO$_2$-OA alkylation of RAD51 Cys319 is further stabilized by hydrophobic interactions with Pro318 of RAD51 and hydrogen bonding with Glu322 (FIG. 3E).

Figure 3F:
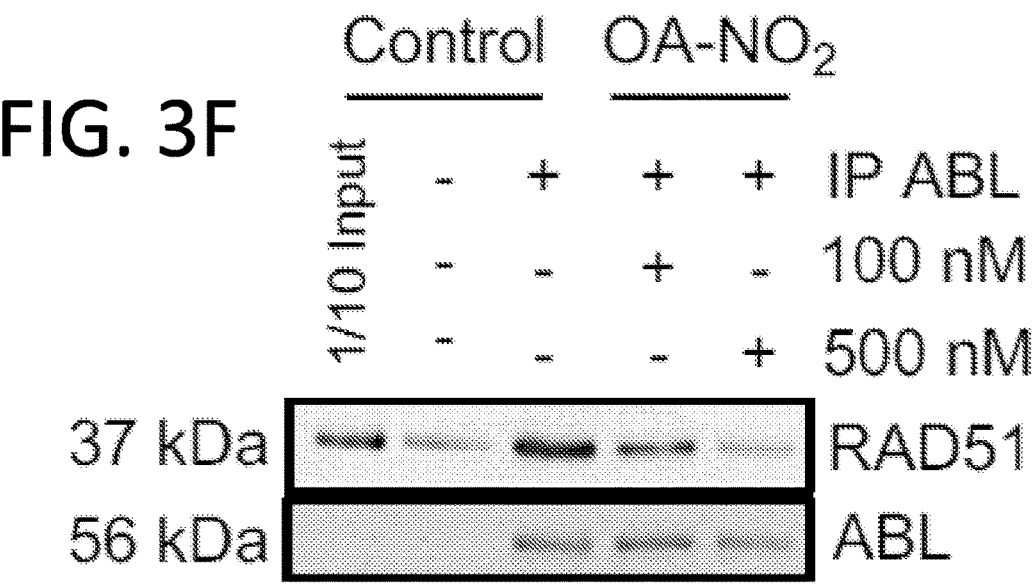
Figure 3G:
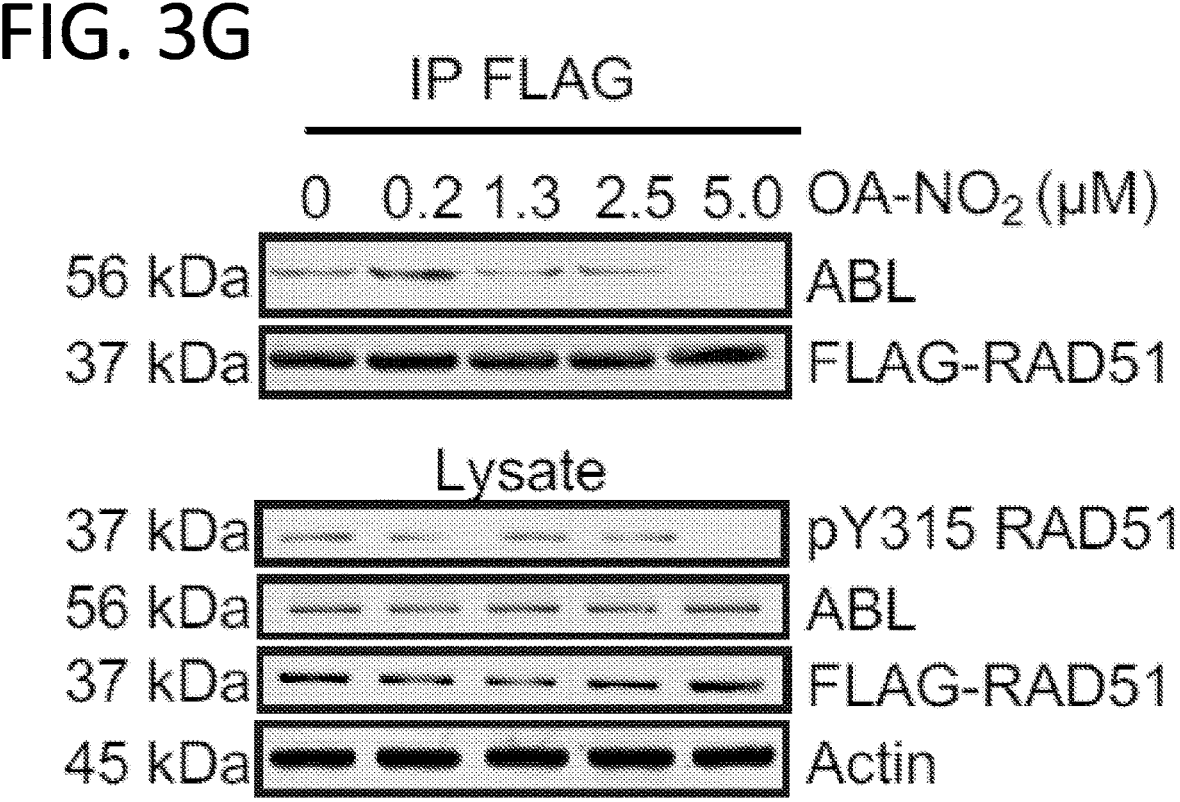
Figure 3H:
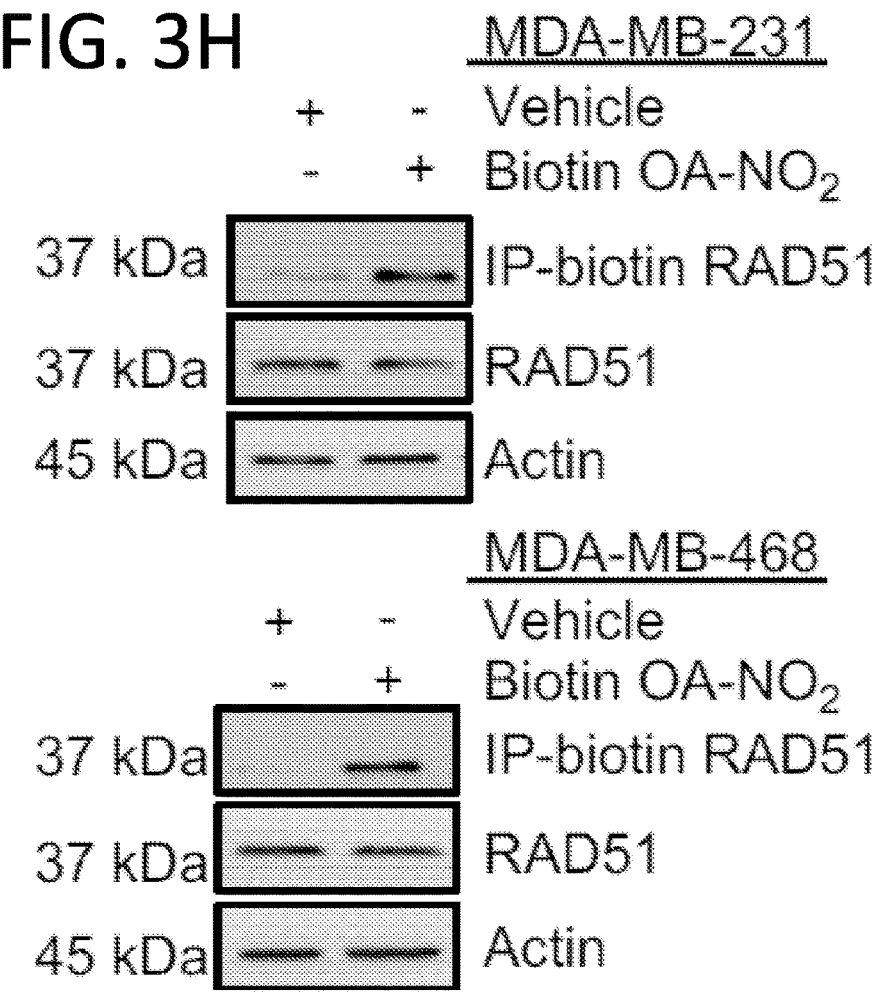
Figure 3I:
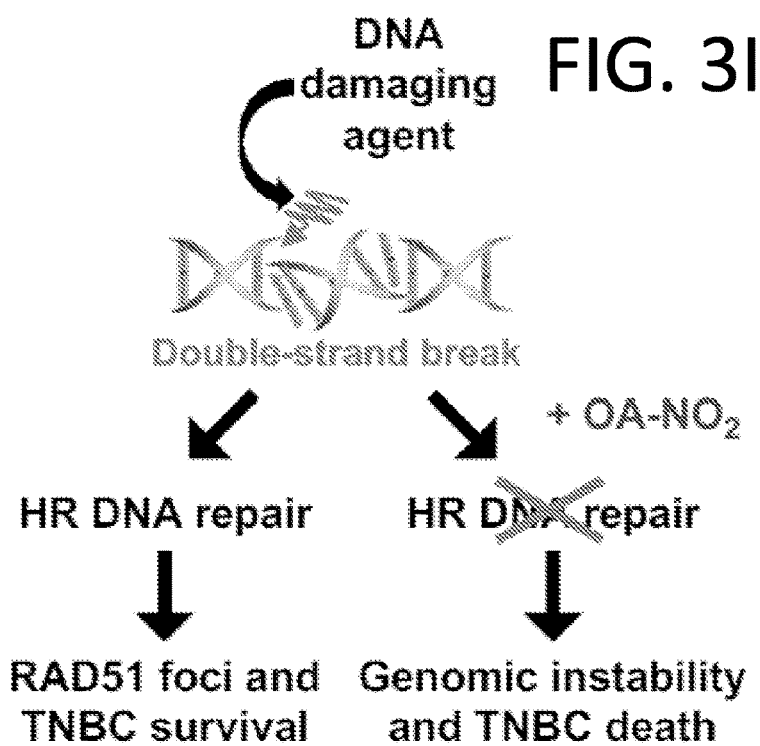

Cys319 is located in the RAD51 C-terminus within one of the two ABL-SH3 binding domains (amino acids 283-286 and 318-321). In addition to RAD51 filament disruption, NO$_2$-OA inhibited heterodimerization of RAD51 and ABL. IP analysis revealed that purified RAD51 and catalytic ABL core (SH2, SH3 and kinase domain only) complex formation was abolished by NO$_2$-OA (FIG. 3F). ABL regulates RAD51 activity via sequential phosphorylation of RAD51 Tyr54 and then Tyr315. By transfecting FLAGRAD51 and ABL core into 293T cells, the impact of NO$_2$-OA on RAD51-ABL complex formation and RAD51 Tyr315 phosphorylation was examined. After treating cells with 0 to 5 μM NO$_2$-OA for 1 h, FLAG IP analysis revealed that NO$_2$-OA decreased the amount of ABL bound to RAD51 (FIG. 3G). Along with the inhibition of RAD51-ABL complex formation, RAD51 Tyr315 phosphorylation was also inhibited by NO$_2$-OA in FLAG-RAD51 and ABL expressing cells. To define whether NO$_2$-OA alkylates endogenous RAD51 in TNBC cells, biotin-NO$_2$-OA was added to MDA-MB-231 and MDA-MB-468 cells. Biotin-NO$_2$-OA-RADS1 complex formation upon streptavidin precipitation was observed in lysates of both cell lines (FIG. 3H). Overall, these data reveal that NO$_2$-OA inhibited HR by forming adducts with RAD51 and possibly additional HR-related target proteins to enhance sensitivity to DNA-directed cancer therapies (FIG. 3I).

EXPERIMENTAL PROCEDURES—Nitroalkene fatty acid inhibition of triple negative breast cancer cell viability, migration, invasion and tumor growth Cell Culture and Reagents.

Cell lines were purchased from ATCC. MDA-MB-231 and MCF7 cells were cultured in Dulbecco's modified Eagle's medium and MDA-MD-468 cells were cultured in Improved Minimum Essential medium (Gibco, Gaithersburg, MD), each supplemented with 5% fetal bovine serum (Hyclone, Logan, UT). MCF-10A cells were cultured in growth medium consisting of DMEM:F12 (1:1) in 5% horse serum (Hyclone), and supplemented with 0.5 ng/mL hydrocortisone, 0.1 ng/mL cholera toxin, 20 ng/mL EGF, and 10 ng/mL insulin (Sigma-Aldrich, St. Louis, MO). Cells were incubated at 37° C. in a 5% CO$_2$ atmosphere. siRNA directed against human RelA (L-003533-00-0005), human MRP1/ABCC1 siRNA (L-007308-00-0005) and non-targeting control siRNA (D-001810-10-05) were purchased from Dharmacon RNAi Technologies. Lipofectamine 2000 or 3000 (Life Technologies) was used for cell transfection. The MRP1 inhibitor Probenecid (4-[(dipropylamino)sulfonyl] benzoic acid) was purchased from Enzo Life Sciences and dissolved in 1 M sodium hydroxide. The NF-κB inhibitor JSH-23 (4-Methyl-N1-(3-phenyl-propyl)-benzene-1,2-diamine) and proteasome inhibitor MG-132 (Z-LLeu-D-Leu-L-Leu-al) were purchased from Sigma-Aldrich. The IKKβ inhibitor Bay 11-7082 (3[(4-methylphenyl)sulfonyl]-(2E)-propenenitrile) was purchased from Calbiochem and TNFα was from BD Biosciences.

Cell Treatment for IKKβ Phosphorylation, IκBα Phosphorylation, and IκBα Degradation.

All studies used two TNBC cell lines, MDA-MB-231 and MDA-MB-468. To determine the effect of NO$_2$-OA on IKKβ phosphorylation induced by TNFα in TNBC cells, cells were pretreated with NO$_2$-OA (5 μM), NO$_2$-SA (5 μM), or BAY11-7082 (10 μM) in serum-free media (DMEM containing 0.1% fatty acid-free BSA) for 2 hr before TNFα (20 ng/mL) stimulation for 5 min. For IκBα degradation, cells were treated as described above and stimulated with 20 ng/mL TNFα for 10 min. For IκBα phosphorylation, cells were pretreated with MG-132 (10 μM) in combination with NO$_2$-OA (5 μM), NO$_2$-SA (5 μM), or BAY11-7082 (10 μM) in serum free media for 2 hr before TNFα (20 ng/mL) stimulation for 10 min.

NO$_2$—FA Synthesis and Use.

Oleic acid (OA; octadec-9-enoic acid) was purchased from Nu-Chek Prep (Elysian, MN). Nitro-stearic acid (NO$_2$—SA; 10-nitro-octadecanoic acid) was obtained by the reduction of 10-nitro-oleic acid. Specifically, NO$_2$-OA was dissolved in THF/methanol and cooled, then sodium borohydride was added. The flask was stirred and aliquots were monitored by UV analysis until there was full loss of the nitroalkene, then the reactions were quenched with acetic acid. NO$_2$—SA was purified by first adducting any remaining NO$_2$-OA with added cysteine, then NO$_2$-SA was chromatographically fractionated on silica gel, using an ethyl acetate/hexane gradient. OA, NO$_2$-OA, and NO$_2$-SA were dissolved in absolute methanol and diluted in culture medium immediately before use in all experiments, at a maximum methanol concentration of 0.1%, vol/vol. Biotinylated NO$_2$—FAs (Bt-NO$_2$-OA, Bt-NO$_2$—SA, and Bt-OA) were synthesized from corresponding free fatty acids and biotin-(polyethylene glycol)-amine.

Cell Growth Assay.

Cells were plated at a cell density of 5000 cells per well in 96-well plates. After attachment overnight, the media was replaced and cells were treated with 0 to 15 μM NO$_2$-OA, NO$_2$—SA, or 0.1% methanol (vehicle) for 48 hr. In an MRP inhibition study, MCF-10A cells were pretreated with 0.25 mM probenecid for 1 hr followed by 0 to 25 μM NO$_2$-OA for 48 hr. Cells were counted using the FluoReporter dsDNA quantitation kit (Molecular Probes) according to the manufacturer's instructions. Fluorescence was measured using a SpectraMax M2 plate reader (Molecular Devices). The half maximal inhibitory concentration (IC50) of NO$_2$-OA was determined by using CalcuSyn software from Biosoft. Three individual experiments were done (n=5/each), and statistical comparison between two cell lines across doses was determined by two-way analysis of variance followed by Tukey post-test.

Fluorescence-Activated Cell Sorting (FACS).

MCF-10A, MDA-MB-231, and MDA-MB-468 cells were plated at a cell density of 2.5×105 cells in 6-well plates for 24 hr before treatment with 0.1% methanol (vehicle), 5 μM NO$_2$-OA, NO$_2$-SA, or OA for 24 hr. Adherent and nonadherent cells were collected, centrifuged at 2000×rpm for 10 min, washed with ice-cold phosphate-buffered saline, fixed with cold 70% ethanol at 4° C. for 30 mins, and stained with 50 μg/mL propidium iodide (Sigma-Aldrich). FACS analysis was performed at the University of Pittsburgh Department of Immunology Unified Flow Core Facility. Three individual experiments were done, and statistical comparisons among phases (G0/G1, S, and G2/M) were determined by one-way analysis of variance followed by Tukey post-test.

Cell Migration Analysis.

MDA-MB-231 and MDA-MB-468 cells were subjected to cell migration analysis in Boyden chambers. The bottom of a 12-well membrane filter (BD Biosciences) was coated with 10 μg/mL fibronectin for 12 hr before each experiment. Cells were pre-treated with 5 μM NO$_2$-OA or NO$_2$—SA for 1 hr and then in the absence or presence of TNFα (20 ng/mL) for an additional 2 hr in culture medium containing 1% FBS. Cells were trypsinized and washed with migration media (DMEM containing 0.1% fatty acid-free BSA) to remove serum. Cells at a density of 10$^5$/well were then placed in the upper chamber with migration media containing the same pretreatment conditions. The cells were allowed to migrate towards the 5% FBS chemoattractant for 5 hr. Non-migrated cells from the top surface were removed with cotton swabs. Migrated cells were fixed with 4% paraformaldehyde (Electron Microscopy Sciences), then stained with 0.5% crystal violet (Sigma-Aldrich) for 15 min. Migrated cell density on the filters was observed by microscopy. The crystal violet on migrated cells was de-stained with 10% acetic acid, and the absorbance in individual filters was determined at A573 nm. Images are representative of three individual experiments, and statistical comparison among treatments was determined by one-way analysis of variance followed by Tukey post-test.

Cell Invasion Assay.

MDA-MB-468 cells were pre-treated with $NO_2$-OA (5 µM), $NO_2$-SA (5 µM), or NF-κB inhibitor JSH-23 (10 µM) for 1 hr and then in the absence or presence of TNFα (20 ng/mL) for an additional 2 hr in culture medium containing 1% FBS. Cells were then suspended in migration media and placed in the top well of invasion chambers (EMD Millipore). Chemoattractant (5% FBS) was placed in the lower chamber for 24 hr at 37° C. to attract invasive cells. Cells were then harvested and invasion rates were determined according to manufacturer's protocol. Three individual experiments were done, and statistical comparison among treatments was determined by one-way analysis of variance followed by Tukey post-test.

Luciferase Analysis of NF-κB Activity.

Luciferase-chemiluminescence-based analysis of NF-κB transcriptional activity was performed. MDA-MB-231 and MDA-MB-468 cells (~70% confluence) in 12-well plates were transiently transfected with a NF-κB-luciferase reporter plasmid (Stratagene, La Jolla, CA) with Lipofectamine 3000. After transfection (24 hr), cells were pre-treated with $NO_2$-OA (5 µM), $NO_2$-SA (5 µM), OA (5 µM), or JSH-23 (20 µM) for 2 hr, followed by 20 ng/mL TNFα for an additional 4 hr. Each transfection was performed in triplicate. Luciferase activity was measured using the Dual-luciferase assay kit (Promega). Relative light units (RLU) were measured using a 96-well plate luminometer, according to the manufacturer's instructions (Victor II, PerkinElmer Life Sciences). Protein concentration was determined using the BCA Assay (Thermo Fisher Scientific). Data represents the ratio of treated samples to controls in the context of mean RLU/protein content, +/−SD. Three individual experiments were done, and statistical significance was determined by Kruskal-Wallis test followed by Dunn's post-test with Bonferroni corrections for multiple comparisons.

$NO_2$-FA Protein Alkylation Reactions.

To determine whether $NO_2$—FAs bind to RelA (p65) or IKKβ in TNBC cells, MDA-MB-231 or MDA-MB-468 cells were treated with 5 µM biotinylated (Bt) lipids Bt-$NO_2$-OA, Bt-$NO_2$—SA, or Bt-OA in DMEM containing 5% FBS. After 2 hr cells were harvested in lysis buffer containing 1% Triton X, 10% glycerol, 150 mM NaCl, 10 mM HEPES, 1 mM EDTA, 1 mM EGTA, and supplemented with a mixture of protease and phosphatase inhibitors (Roche Applied Science). Total cell lysates (0.5-1 mg) were mixed and incubated with streptavidin agarose beads (Sigma-Aldrich) at 4° C., overnight. Beads were washed three times using lysis buffer. After SDS-PAGE, immunoblotting was performed using anti-RelA mouse monoclonal antibody (Santa Cruz Biotechnology) or anti-IKKβ rabbit polyclonal antibody (Cell Signaling). Proteomics analysis for the alkylation of RelA by $NO_2$-OA was also conducted using recombinant RelA protein and LC-MS/MS analysis.

Immunoprecipitation and $NO_2$—OA-Induced RelA Protein Polyubiquitination.

To determine the induction level of RelA protein polyubiquitination by $NO_2$—FA, MDA-MB-231 and MDA-MB-468 cells were treated with 0.1% methanol (vehicle), $NO_2$-OA (5 µM), or $NO_2$-SA (5 µM) for 6 hr, then cell lysates were harvested in lysis buffer supplemented with a mixture of protease and phosphatase inhibitors. Lysates were clarified by centrifugation at 14,000×g for 10 min. Protein lysates (1 mg) were incubated with anti-RelA antibody and Protein G/A conjugated agarose beads (EMD Millipore, Bedford, MA) at 4° C., overnight. Immunoprecipitation fraction were obtained by centrifugation at 14,000×g for 1 min at RT and washed with lysis buffer three times. The immunoprecipitated RelA was resolved by 8% SDSPAGE gel, and transferred to nitrocellulose membrane (Bio-Rad) for immunoblotting probed with an anti-ubiquitin antibody (Santa Cruz Biotechnology). The blot was then stripped and probed with an anti-RelA antibody to assess amounts of RelA protein pull-down.

Western Blotting.

Western blotting was performed. 20-60 µg of total lysates per lane were loaded on 7%, 10%, or 12% SDS-PAGE and transferred onto nitrocellulose or polyvinylidene difluoride membranes (Bio-Rad). The membranes were probed with primary antibodies against caspase-3, multi-drug resistance protein-1 (MRP1), poly [ADP ribose] polymerase-1 (PARP-1), ubiquitin, RelA; cyclin D1, p21, caspase-9, MRP4, IKKβ, pIKKβ, IκBα, or pIκBα (Cell Signaling); caspase-8 (R&D Systems). Samples were normalized to β-actin (Sigma-Aldrich) or GAPDH (Trevigen).

Protein bands were visualized and digitized images quantified using Image Lab software (Bio-Rad). Immunoblots are representative of at least three individual experiments. Quantitative results are an average of ≥3 individual experiments, and statistical significance was determined by one-way analysis of variance followed by Tukey post-test.

RNA Extraction, qPCR, and RT2 Profiler PCR Array.

To determine the effect of $NO_2$-OA on expression of NF-κB target genes in TNFα-induced MDA-MB-231 and MDA-MB-468 cells, cells were pretreated with $NO_2$-OA (5 µM) for 2 hr and then stimulated with TNFα (20 ng/mL) for 6 hr. Total RNA samples of tissues or cells were extracted using TRIZOL reagents according to the manufacturer's instructions (Invitrogen). Total RNA (1 µg) was reverse transcribed using the iScript cDNA kit (Bio-Rad) according to manufacturer instructions. cDNA (25 ng) was used for each subsequent quantitative real-time PCR (qRT-PCR) reaction. All qRT-PCR was performed on the StepOne PLUS PCR system (Thermo Fisher Scientific) using TaqMan gene expression assays. Fold change was calculated using the ΔΔCt method with 18S ribosomal RNA or human β-actin RNA serving as the internal control. Three individual experiments were done, and statistical significance was determined by one-way analysis of variance followed by Tukey post-test. For the $RT^2$ profiler PCR array, MDA-MB-468 cells were treated or untreated with $NO_2$-OA (5 µM) for 24 hr. The expression of 84 human NF-κB target genes was analyzed with 96-well plate format as instructed in the manufacturer's handbook (Qiagen). PCR amplification was conducted by StepOne PLUS PCR system and fold change of gene expression was calculated according to the manufacturer's instruction.

Analysis of $NO_2$—OA GSH Conjugates ($NO_2$—OA-SG) and $NO_2$—OA in Cell Media.

MCF-10A, MDA-MB-231 or MDA-MB-468 cells were cultured in 6-well plates ($1\times10^6$ cells per well) for 24 hr.

Before treatments, cell media was replaced with DMEM containing 5% FBS. NO$_2$-OA (5 µM) was added to the media and cells were incubated at 37° C. for 60 mM before the cell culture media was collected. For MRP1 inhibition studies, MCF-10A cells were pretreated with 1 mM probenecid for 1 hr and then co-treated with 5 µM NO$_2$-OA for an additional 1 hr. For MRP1 siRNA knockdown studies, MCF-10A cells were transiently transfected with non-target siRNA (Scrambled) or MRP1 siRNA for 48 hr before treatment with 5 µM NO$_2$-OA for 1 hr. Cells were washed with PBS and then gently scraped off the plate in 1 mL PBS. 100 µL of cell suspensions were lysed by sonication and used for protein concentration measurements via BCA protein assay. The remaining 0.9 mL of cell suspension was used to determine the amount of intracellular NO$_2$-OA-SG. NO$_2$-OA-SG and free NO$_2$-OA were extracted using a modified Bligh-Dyer method with NO$_2$-OA-SG partitioning into the polar phase and NO$_2$-OA into the organic. The cell culture media was spiked with $^{15}$NO$_2$-d4-OA (5 nM) as internal standard for free NO$_2$-OA before extraction. Samples were centrifuged at 2,800 rpm, RT for 5 min. The bottom (organic) layer was transferred to a clean vial, dried and reconstituted in methanol before MS analysis. The upper (aqueous) layer containing NO$_2$-OA-SG was desalted and concentrated using 3 mL C18 SPE columns (Thermo Fisher Scientific). Columns were preconditioned with one column volume of 100% methanol, followed by 2 column volumes of 5% methanol before sample addition. Samples were vortexed and equilibrated at 4° C. for 5 min prior to extraction. Samples were washed with two column volumes of 5% methanol and the column dried under vacuum for 30 min before elution with 3 mL of 100% methanol. Solvent was then evaporated under N$_2$ and the samples were reconstituted in methanol for further analysis.

GSH and GSSG Extraction and Analysis.

MCF-10A, MDA-MB-231, and MDA-MB-468 cells were seeded in 24-well plates at a density of 3×10$^5$ cells/well. Cells were cultured overnight prior to treatment with 5 µM NO$_2$-OA for the indicated times. At each time point, cell media was aspirated and washed 2 times with sterile PBS. Cells were then incubated with PBS containing 25 mM N-ethylmaleimide (NEM) for 15 min at 37° C. Derivatizing solution (50 µL of 15% MeOH, 40 mM HEPES, 50 mM NaCl, 1 mM EDTA, 2 µM [$^{13}$C$_2$$^{15}$N]-GSH, 2 µM [$^{13}$C$_4$$^{15}$N2]-GSSG, and 25 mM NEM) was added to each well and incubated for 15 min at room temperature. Next, 50 µL, of 10% (w/v) sulfosalicylic acid solution was immediately added to each well to stabilize GSH and GSSG. Supernatant was collected by centrifugation at 15,000 RPM for 10 min at 4° C. Samples were diluted 1:5 in 5% sulfosalicylic acid and 20 µL, was injected for HPLC-MS/MS analysis. Cell numbers at time 0 hr were quantitated by Hoechst 33258 DNA stain assay and used to normalized GSH or GSSG levels expressed as nmol/cells (×10$^6$).

Liquid Chromatography Mass Spectrometry (LC-MS/MS).

NO$_2$-OA, NO$_2$-OA-SG, GSH and GSSG were analyzed by high performance liquid chromatography-electrospray ionization tandem mass spectrometry (LC-MS/MS) using a Shimadzu/CTC PAL HPLC coupled to a Sciex 5000 triple quadrupole mass spectrometer (Sciex, San Jose, CA). NO$_2$-OA, NO$_2$-OA-SG gradient solvent systems consisted of water+0.1% acetic acid (solvent A) and acetonitrile+0.1% acetic acid (solvent B). NO$_2$-OA and its metabolites were resolved using a Luna C18 reversed phase column (2 mm×100 mm, Phenomenex, Torrence, CA) at a flow rate of 0.65 mL/min. Samples were applied to the column at 30% B and eluted with a linear increase in solvent B (30-100% in 9.7 min). The column was washed at 100% B for 3 min before returning to initial conditions for equilibration (2 min). NO$_2$-OA-SG conjugates were resolved using a Luna C18 reversed phase column (2 mm×150 mm, Phenomenex) at a 0.25 mL/min flow rate. Samples were applied to the column at 20% B held for 5 min and eluted with a linear increase in solvent B (20-98% solvent B in 20 min), followed by a wash step at 98% B for 4.5 min, and switched back to initial conditions for 4 min. MS analyses for NO$_2$-FAs used electrospray ionization in the negative ion mode with the collision gas set at 5 units, curtain gas 40 units, ion source gas #1 55 units and #2 60 units, ion spray voltage −4500V, and temperature 600° C. The declustering potential was −80 eV, entrance potential −5, collision energy −35, and the collision exit potential −3. Multiple reaction monitoring (MRM) was used for the analysis of lipids showing loss of a nitro group (m/z 46) upon collision-induced dissociation. (MRM: 326.2/46 and 331/47 for NO$_2$-OA and $^{15}$NO$_2$-d4-OA, respectively) in negative ion mode. The following parameters for the mass spectrometers were used for NO$_2$-OA-SG conjugates in positive ion mode: gas #1 50 and gas #2 55, ion spray voltage 5000 V and the source temperature was set at 550° C., the declustering potential was 70 eV, entrance potential 5, collision energy 17 and the collision exit potential 5. The following MRM transitions were used 635.2/506.2 and 640.2/511.2 for NO$_2$-OA-SG and $^{15}$NO$_2$-d4-OA-SG, respectively. The method for simultaneous determination of GSH and GSSG involved sample (20 µL) separation on a Phenomenex C18 (2.1×150 mm, 3.5µ pore size) column. The solvent system employed aqueous 0.1% formic acid (A) and 0.1% formic acid in acetonitrile (B) with a net flow rate of 0.6 mL/min. A linear gradient of 2% B to 75% B from 0.1-6.2 min, followed by wash with 100% B for 2 min, and re-equilibration with 2% B for 6 min was employed for separation. Unlabeled and $^{13}$C$_4$$^{15}$N$_2$ GSSG eluted at 2 min, while unlabeled and $^{13}$C$_4$$^{15}$N GS-NEM eluted at ~2.7 min. The Sciex 5000 mass spectrometer settings were the following: CAD 4 units, curtain gas 40 units, GS1 45units, GS2 50units, ion spray voltage 5500 V, source temperature 550° C., EP 5V, and CXP 10V. Multiple reaction monitoring was performed in positive ion mode. Transitions for respective species were as follows: GSH (Q1 308.3→Q3 179.1; declustering potential (DP) 60V, collision energy (CE) 18.5V). $^{13}$C$_4$$^{15}$N GSH (Q1 311.3→Q3 182.1; DP 60V, CE 18.5V). GS-NEM (Q1 433.0→Q3 304.2; DP 65V, CE 38V); $^{13}$C$_4$$^{15}$N GS-NEM (Q1 436.0→Q3 307.2; DP 65V, CE 38V); GSSG (Q1 613.2→Q3 355.2; DP 60V, CE 24V); $^{13}$C$_4$$^{15}$N GSSG(Q1 619.2→Q3 361.2; DP 60V, CE 24V). Calibration curves were generated using known GSH and GSSG standards and isotopic internal standards and showed linearity over 5 orders of magnitude and the limit of quantification for both GS-NEM and GSSG was 1 nM. Sample [GSH] and [GSSG] were determined from analyte:I.S. area ratios, and intracellular GSH and GSSG were normalized to cell number (10$^6$), with results expressed as nmol GSH or GSSG per 10$^6$ cells.

Statistical Analysis.

Data analyses were conducted using Prism 6 software (GraphPad Software). Results are presented as mean±SD except tumor volumes except FIG. 4E, which is presented as mean±SEM. Statistical analysis was performed using Student's t-test, one-way or two-way analysis of variance as appropriate. Statistical significance was achieved with $p < 0.05$.

RESULTS—Nitroalkene fatty acid inhibition of triple negative breast cancer cell viability, migration, invasion and tumor growth $NO_2$-OA Inhibits TNBC Cell Growth and Viability.

Figures 4A, 4B:
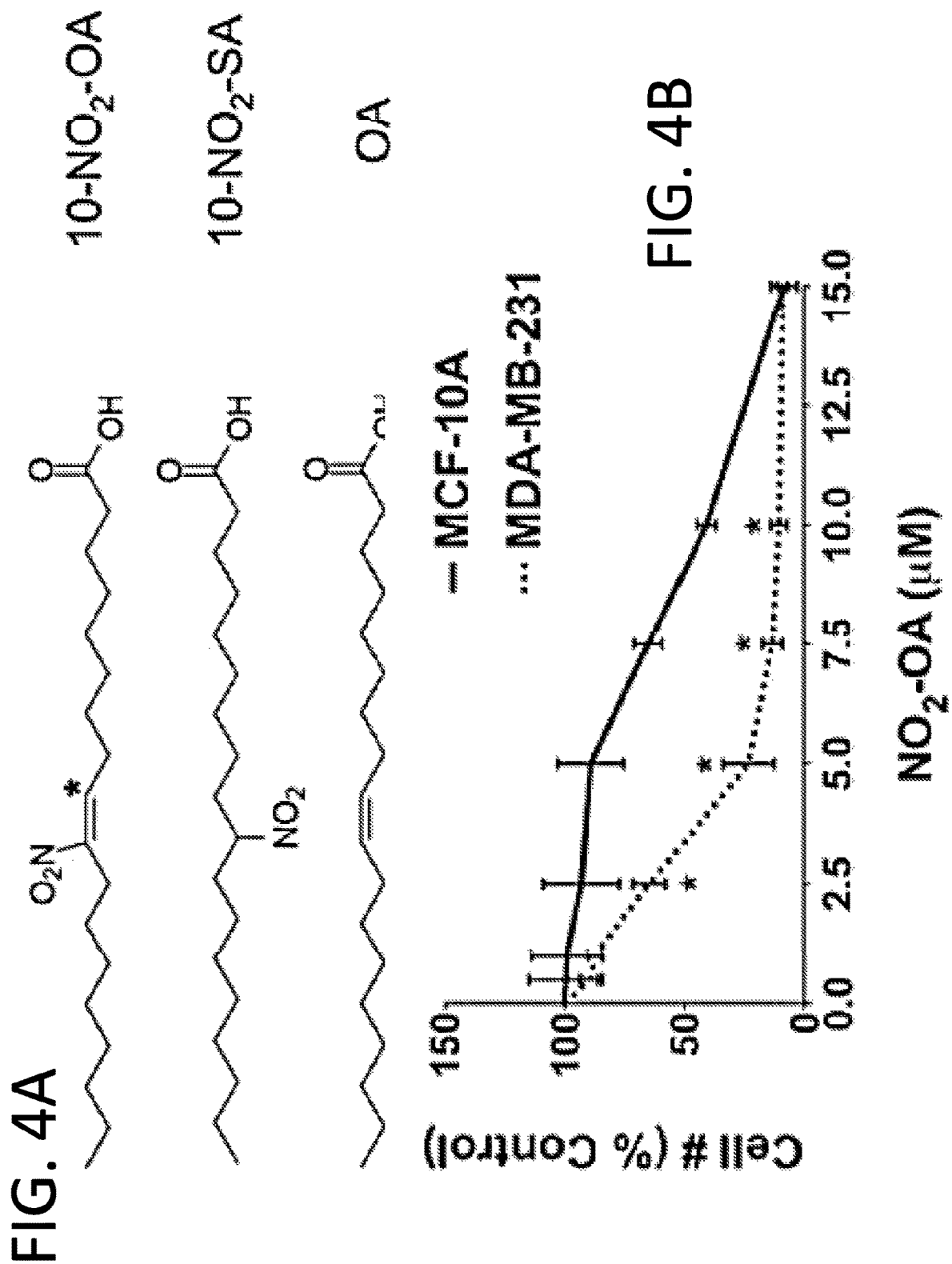
FIGS. 4A-4F. $NO_2$-OA inhibits TNBC cell growth in vitro and in vivo.
Figure 4C:
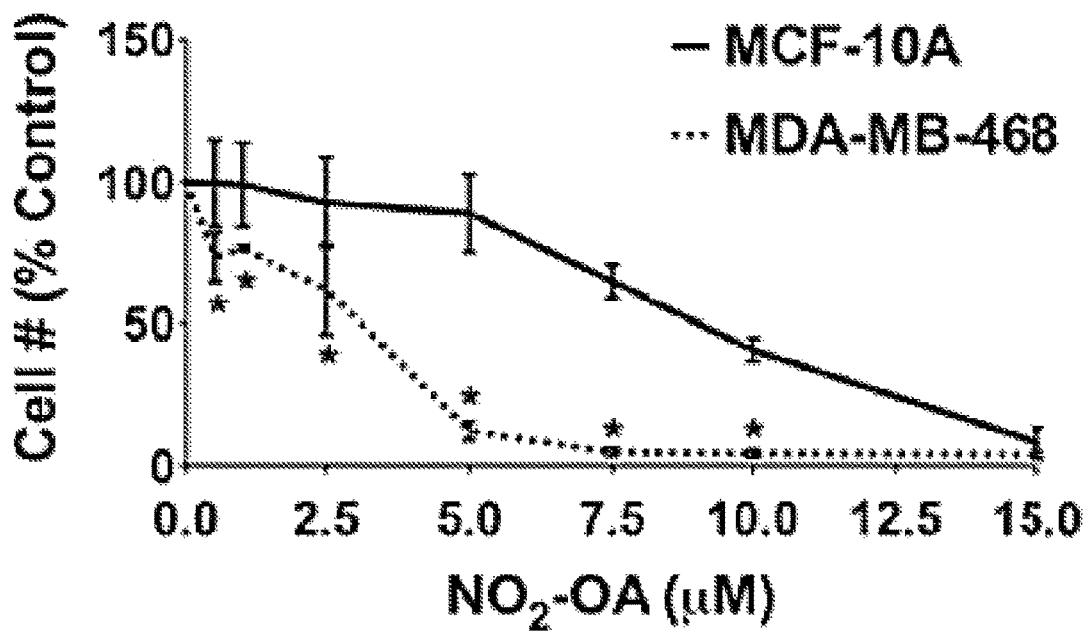
Figure 4D:
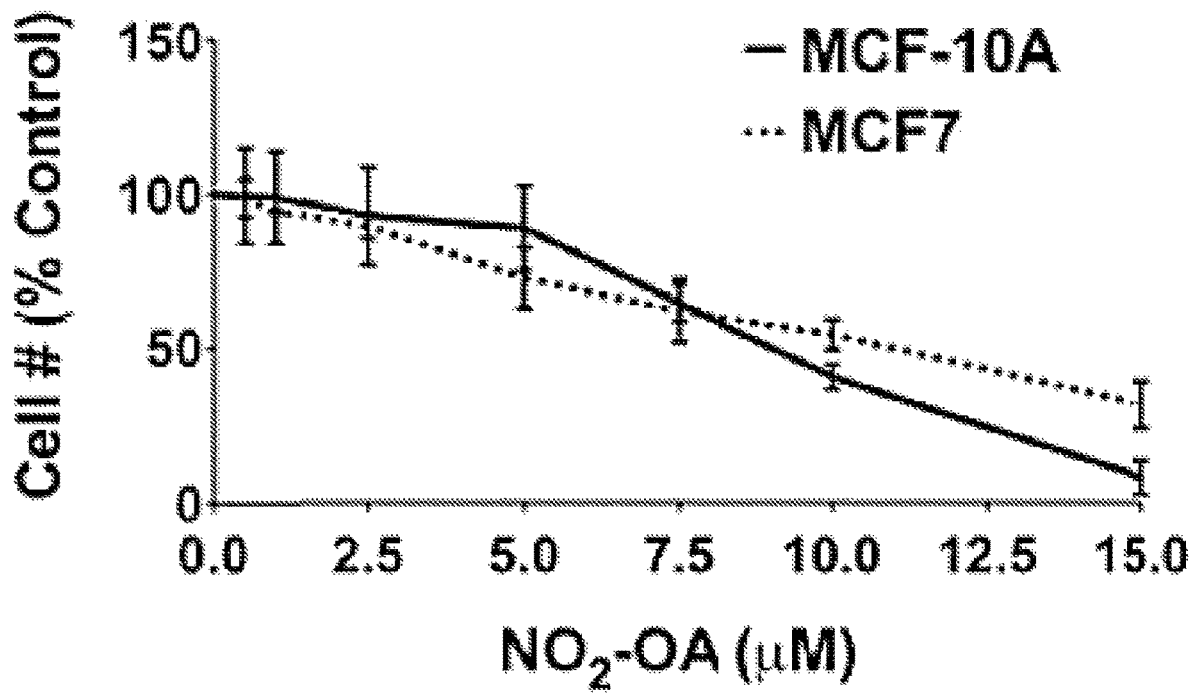
Figures 4E, 4F:
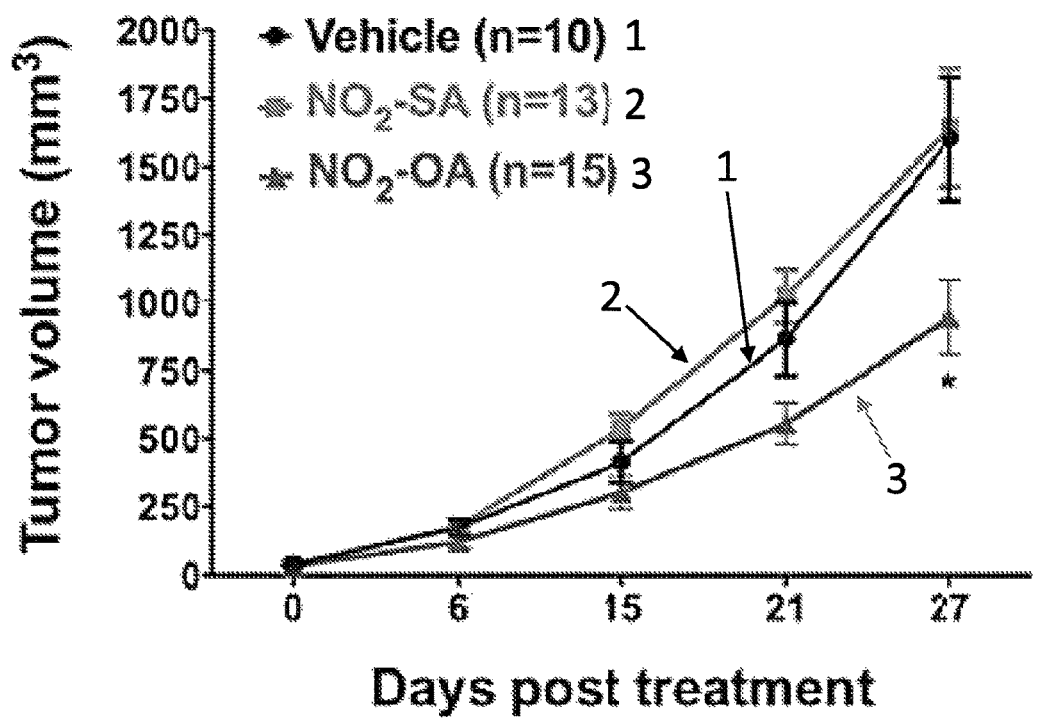
Figure 5C:
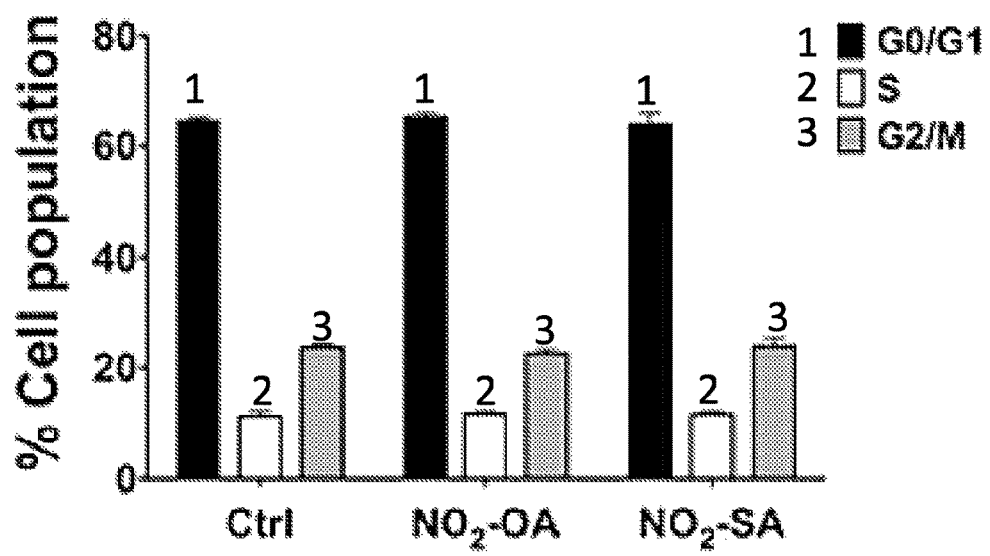

The endogenously-occurring lipid electrophile $NO_2$-OA and its non-electrophilic control fatty acids ($NO_2$-SA and OA) were evaluated for their impact on normal and cancerous breast ductal epithelial cell growth and signaling responses (FIG. 4A). To examine whether $NO_2$-OA preferentially inhibited TNBC cell growth, Hoechst 33258 was used for counting non-tumorigenic breast epithelial cells (MCF-10A), an ER+ breast cancer cell line (MCF7), and two TNBC cell lines (MDA-MB-231 and MDA-MB-468). Each cell line was treated with a range of $NO_2$-OA concentrations (0-15 µM) for 48 hr. $NO_2$-OA significantly inhibited the growth of both TNBC cell lines but not ER+ or MCF-10A cells (FIGS. 4B, 4C, 4D). The IC50 for $NO_2$-OA was significantly greater for non-cancerous MCF-10A cells (7.7±1.93 µM) and MCF7 (11.61±3.59 µM), as opposed to TNBC MDA-MB-231 (2.7±0.11 µM) and MDAMB-468 (1.6±0.11 µM) cells (FIG. 4E). In addition to preferential TNBC cell growth inhibition, MTT detection of intact cell electron transfer mechanisms revealed that $NO_2$-OA also significantly reduced the viability of both MDA-MB-231 and MDA-MB-468 cells, but not MCF7 or MCF-10A cells. No cytotoxicity was detectable in any cell line for up to 24 hr at the 5 µM $NO_2$-OA concentrations typically used for subsequent cell signaling and functional studies that had durations ranging from 1-8 hr. Non-electrophilic $NO_2$—SA, structurally related to $NO_2$-OA (FIG. 4A), did not affect TNBC cell growth, affirming that $NO_2$—OA-mediated TNBC cell growth inhibition is attributed to the electrophilic nitroalkene moiety.

$NO_2$—OA Reduces MDA-MB-231 Xenograft Tumor Growth.

Given that TNBC cell growth and viability are inhibited by $NO_2$-OA, the efficacy of $NO_2$-OA on tumor growth was examined in a murine xenograft model of TNBC. MDA-MB-231 cells were injected into the fourth inguinal mammary fat pad of 6-week-old female athymic nude mice. Oral gavage with $NO_2$-OA (7.5 mg/kg/day), $NO_2$—SA (7.5 mg/kg/day), or sesame oil (vehicle control) was initiated and continued for 4 weeks after the average tumor sizes reached between 50-100 $mm^3$. There was significantly reduced tumor growth in the mice treated with $NO_2$-OA versus vehicle controls and $NO_2$—SA treated mice at 27 days post-treatment (FIG. 4F). During the course of treatment, there was no weight loss in $NO_2$-OA-treated or control mice.

These results support that $NO_2$-OA mediates in vivo growth suppression of MDA-MB-231 cells with no overt toxic effects.

$NO_2$—OA Induces Cell Cycle Arrest and Apoptotic Cell Death in TNBC Cells.

Figure 5D:
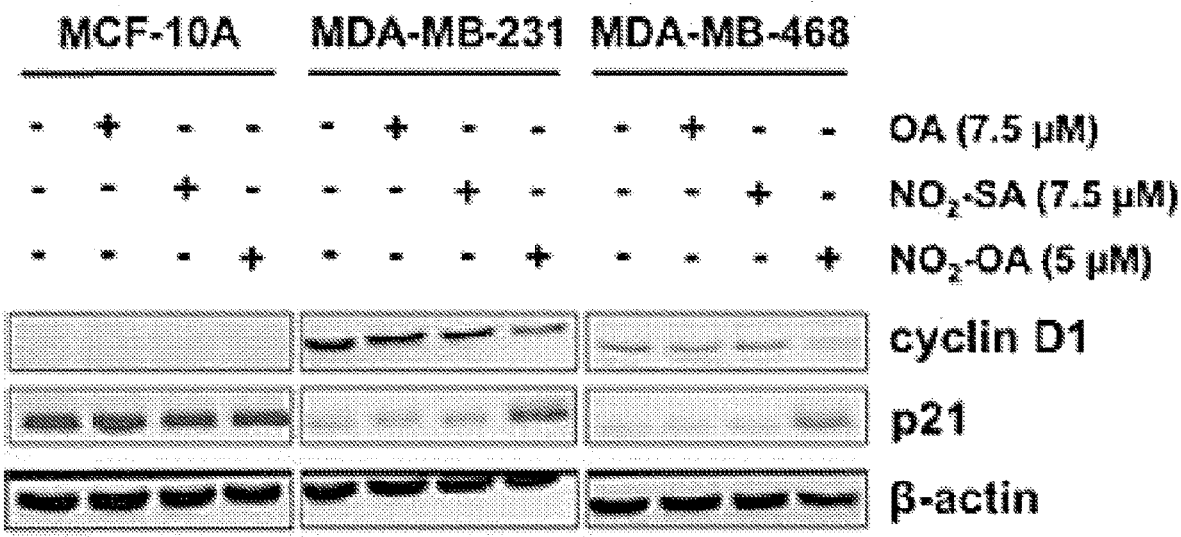
Figure 5E:
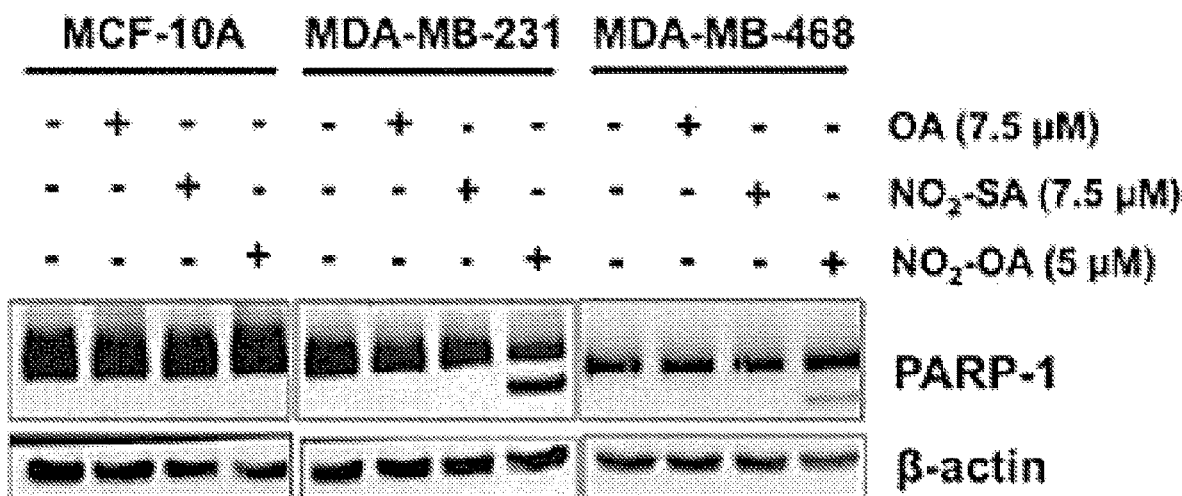
Figure 5F:
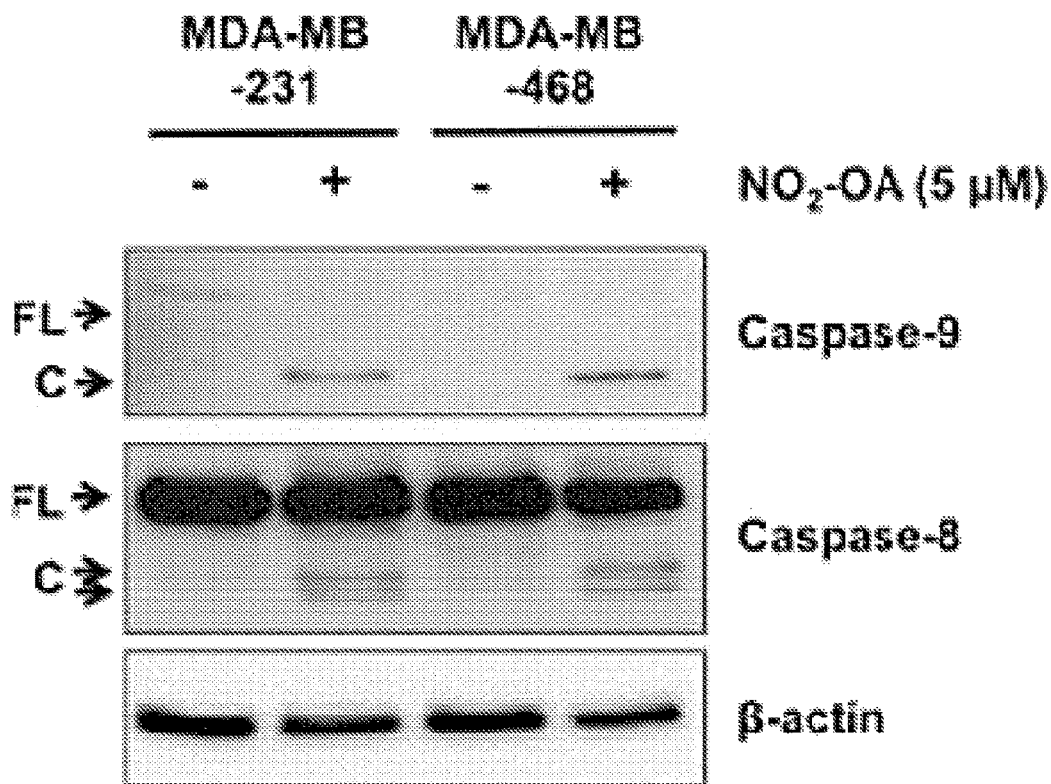

To determine whether the decreased cell numbers were due to $NO_2$-OA-induced cell cycle alterations, fluorescence-activated cell sorting analysis (FACS) was performed. $NO_2$-OA significantly increased the percentage of cells at G2/M phase and decreased the percentage of cells in G0/G1 upon 24 hr treatment in MDA-MB-231 and MDA-MB-468 cells, (FIGS. 5A, 5B). Notably, all cell cycle phase populations (G0/G1, S, and G2/M) of MCF-10A cells were not affected by $NO_2$-OA (FIG. 5C). The cell cycle inhibition by $NO_2$-OA was accompanied by an increase in p21 and a decrease in cyclin D1 protein expression in both MDA-MB-231 and MDA-MB-468 cells, but not MCF-10A cells (FIG. 5D). Consistent with the lack of an effect on cell growth and viability, $NO_2$—SA did not affect cell cycle populations or the expression of cell cycle regulatory proteins in MCF-10A, MDA-MB-231, and MDA-MB-468 cells (FIG. 5D). The gene expression of cyclin D1 and p21 was also determined by quantitative RT-PCR. $NO_2$-OA down-regulated cyclin D1 and up-regulated p21 gene expression after 24 hr treatment of MDA-MB-231 and MDA-MB-468 cells, but not MCF-10A cells. These results indicate that $NO_2$-OA selectively induced cell cycle arrest in TNBC cells. Increased sub-G1 cell populations were apparent in both MDA-MB-231 and MDA-MB-468 cells 24 hr after $NO_2$-OA treatment. To determine whether the effect of $NO_2$-OA on sub-G1 cells in TNBC cells was apoptosis-mediated, cleavage of PARP-1 was examined by western blotting. Treatment with $NO_2$-OA for 24 hr promoted caspase-3-mediated cleavage of PARP-1 (FIG. 5E) in MDA-MB-231 and MDA-MB-468 cells, but not in MCF-10A cells, indicating that $NO_2$-OA preferentially induced TNBC apoptosis through caspase-3 activation. Also, it is possible that the increase in p21 blocks cell cycle entry into the S phase, resulting in the increase in sub-G1 cells. To further investigate apoptotic signaling responses to $NO_2$-OA in TNBC cells, the activation of initiator caspases (caspase-8 for the extrinsic pathway and caspase-9 for the intrinsic pathway) was analyzed using antibodies that detect both the pro-caspase and activated (cleaved) forms of these initiator caspases. $NO_2$-OA treatment increased cleavage of caspase-8 and caspase-9 in both MDA-MB-231 and MDA-MB-468 cells, suggesting that $NO_2$-OA induced apoptosis through both intrinsic (mitochondrial-dependent) and extrinsic (death receptor-dependent) apoptotic signaling mechanisms in TNBC cells (FIG. 5F). In aggregate, these results confirm that $NO_2$-OA selectively modulates cell cycle arrest and apoptosis in TNBC cells versus MCF-10A cells.

Extracellular $NO_2$-OA-Glutathione Adduct Efflux is Linked with MRP1 Expression.

Figure 6B:
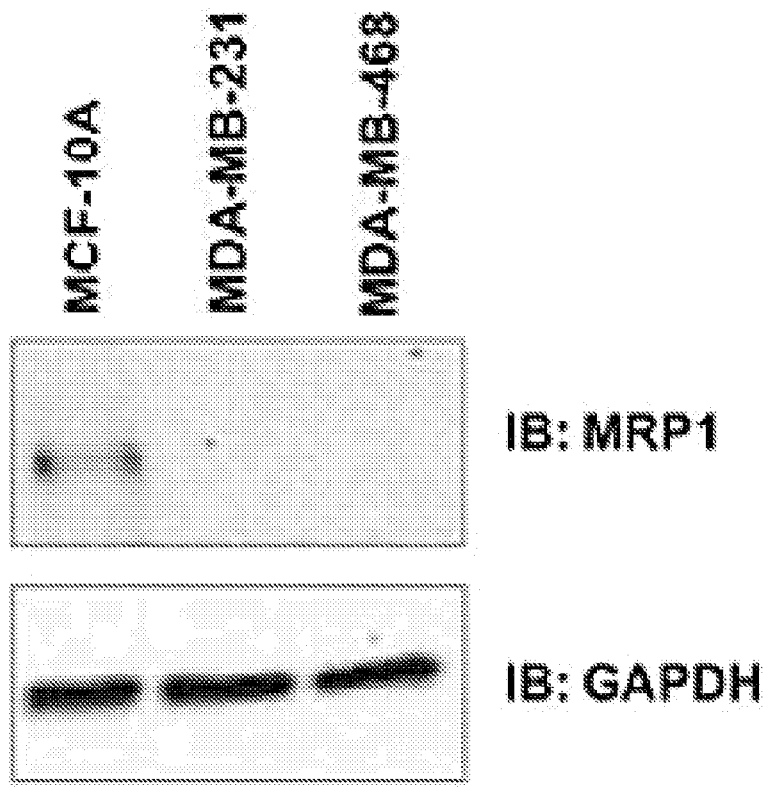

In the intracellular compartment, GSH and its reactive Cys moiety is more abundant than protein thiols, thus GSH and other low molecular weight thiols are the primary targets for oxidation and alkylation by free radicals, oxidants and electrophiles. In the case of $NO_2$-OA, which readily diffuses and gains access to the intracellular compartment and subcellular organelle protein targets, GSH conjugates ($NO_2$-OA-SG) are formed that can be actively transported from cells by the GSH-conjugate efflux pump MRP1. This phenomenon was further investigated by measuring concentrations of extracellular $NO_2$-OA-SG in the media of MCF-10A, MDA-MB-231, and MDA-MB-468 cells after 1 hr treatment with 5 µM $NO_2$-OA. There were significantly lower levels of $NO_2$-OA-SG being exported into the media of both MDA-MB-231 and MDA-MB-468 cells, as opposed to that released by MCF-10A cells (FIG. 6A). This 4- to 5-fold difference in extracellular $NO_2$-OA-SG levels produced by MCF-10A and TNBC cells prompted comparing relative extents of expression of MRP1 protein and the GSH and GSSG content of TNBC and non-cancerous cell lines. Western blot analysis detected MRP1 protein expression in MCF-10A cells, but MRP1 was undetectable in both TNBC cell lines (FIG. 6B). MRP4 mRNA was detected at low levels in all 3 cell types, but protein expression was not evident by western blotting.

MRP1 Influences $NO_2$-OA Bioactivity in MCF-10A Cells.

Figure 6E:
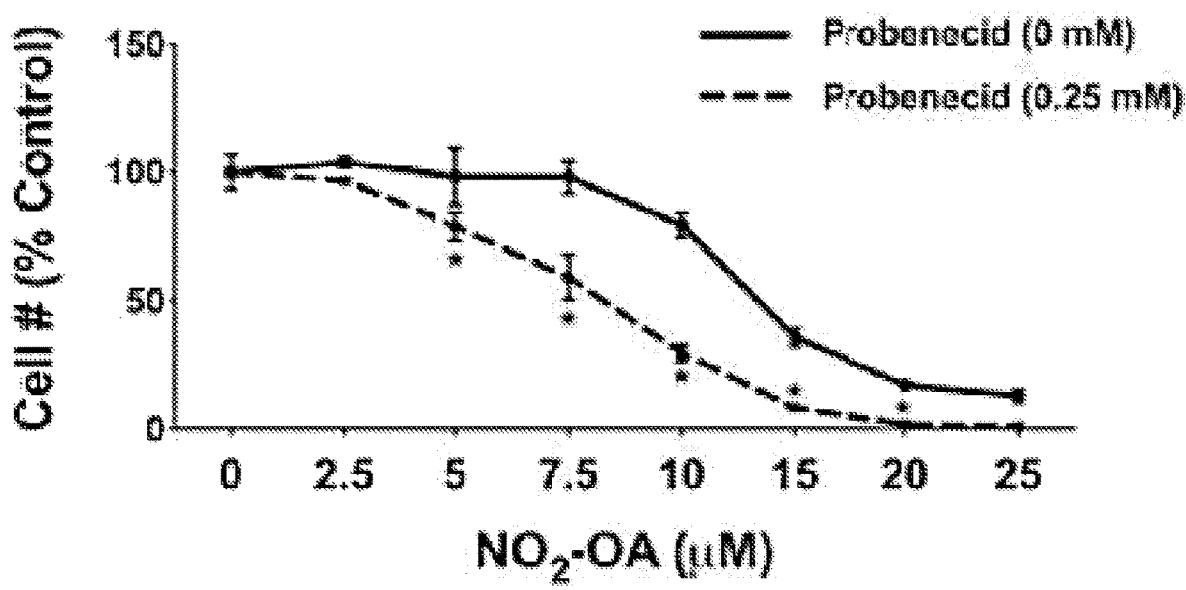
Figure 6F:
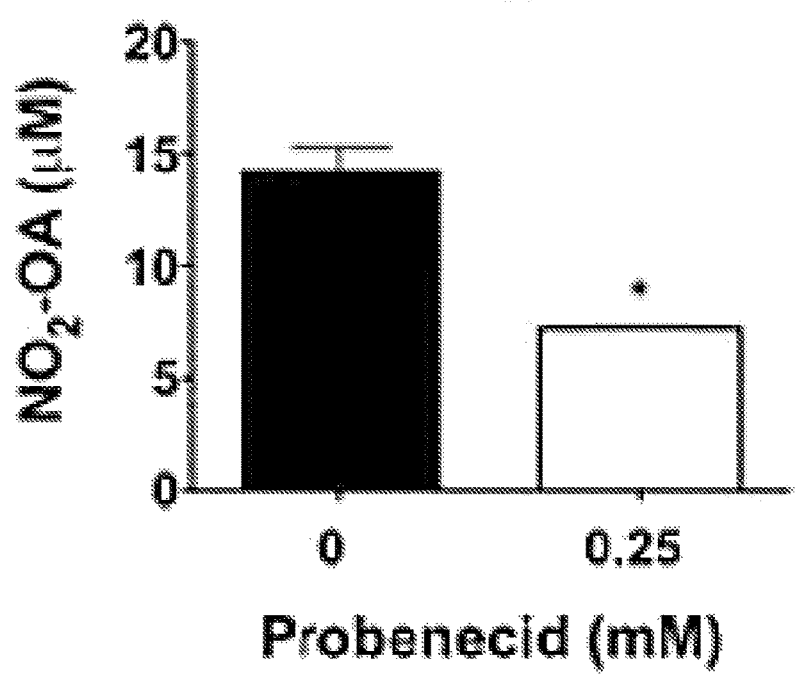
Figure 6G:
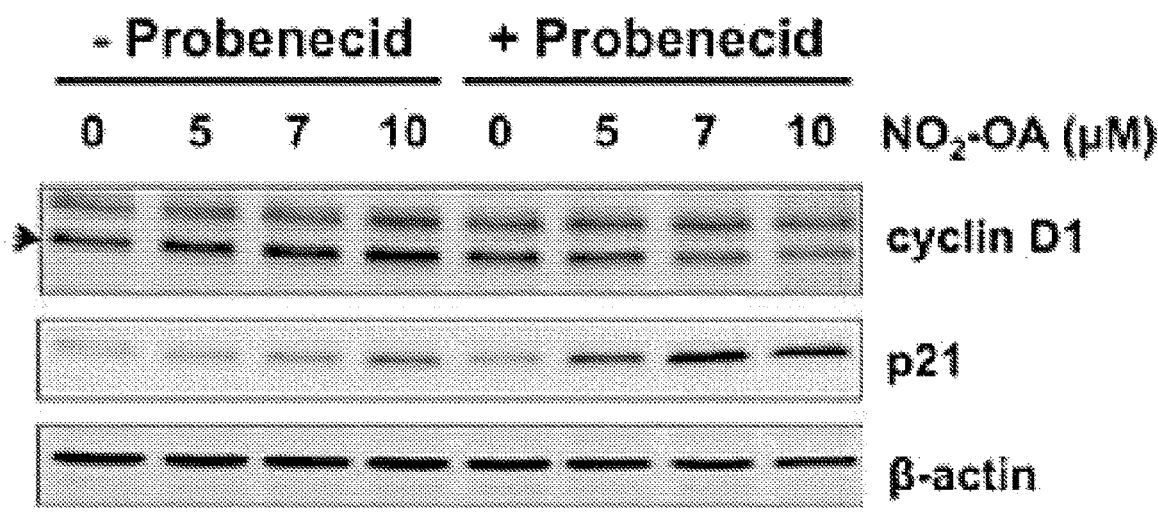
Figure 6H:
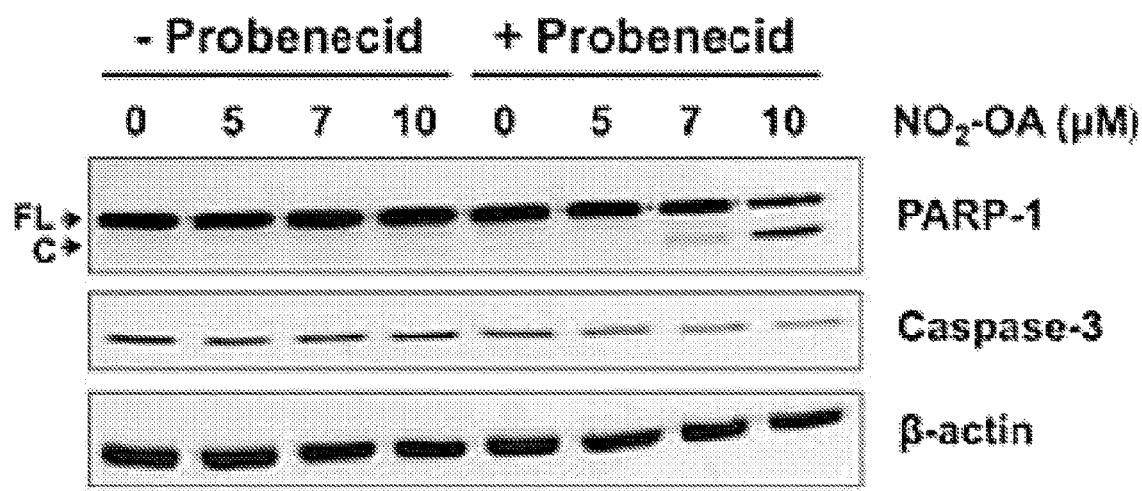

Two strategies, use of the organic anion transport inhibitor probenecid, often used as an MRP inhibitor, and siRNA knockdown of MRP1, facilitated investigation of the role of MRP1 in cellular responses to $NO_2$-OA. Both probenecid and MRP1 siRNA knockdown (about 70% knock-down efficiency) enhanced intracellular levels of $NO_2$-OASG adducts in MCF-10A cells (FIG. 6CD). Notably, probenecid also significantly enhanced MCF-10A cell growth inhibition by $NO_2$-OA (FIG. 6E). The $IC_{50}$ of $NO_2$-OA (7.23±0.15 μM) was decreased 2-fold in MCF-10A cells pretreated with probenecid, compared with only $NO_2$-OA treatment (14.23±1.05 μM; FIG. 6F). Moreover, probenecid increased the extent of $NO_2$—OA-induced cell cycle arrest of MCF-10A cells, as reflected by increased p21 levels and a concomitant decrease in cyclin D1 expression (FIG. 6G). Probenecid also enhanced $NO_2$-OA-induced apoptosis in MCF-10A cells in the context of increased caspase-3 activation and PARP-1 cleavage (FIG. 6H). These observations are consistent with both the intracellular concentrations and the cell growth/cell survival signaling actions of $NO_2$-OA being influenced by extents of $NO_2$-OA reaction with GSH and subsequent MRP1 export of $NO_2$-OA-SG.

GSH and GSSG Responses to $NO_2$—OA in MCF-10A Cells Versus TNBC Cells.

Figure 7A:
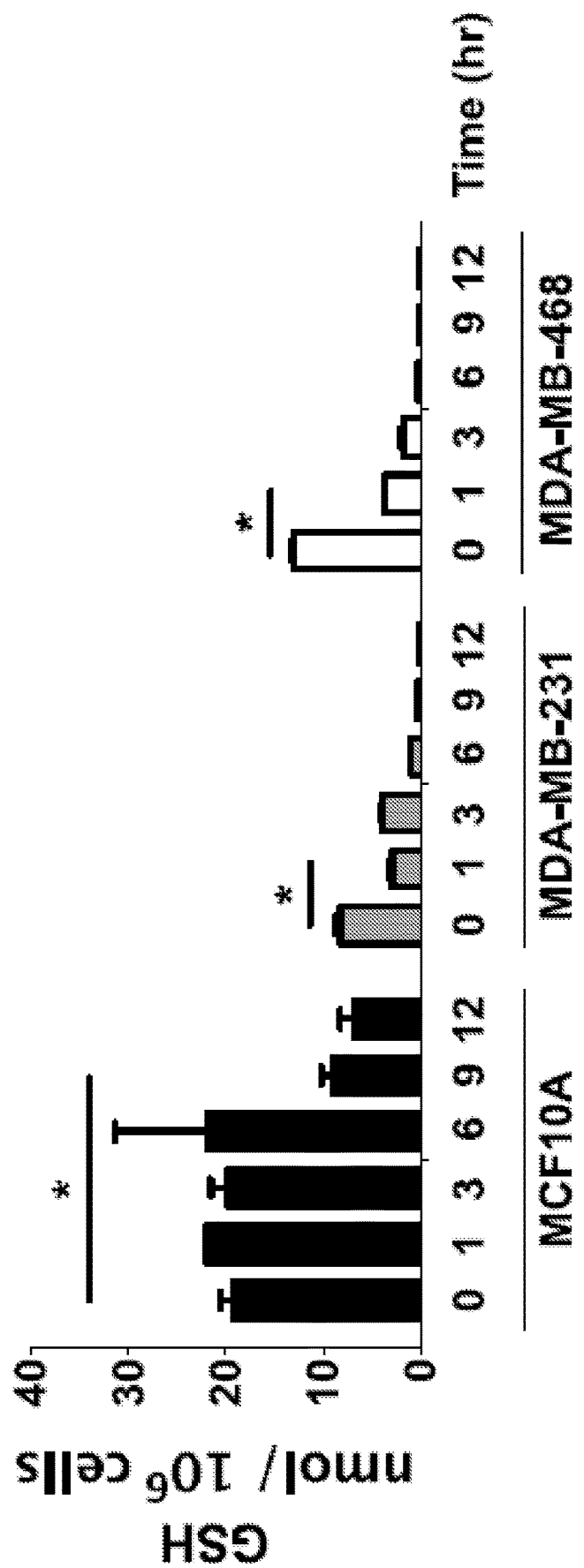

LC-MS quantitation of GSH and GSSG from 0 to 12 hr after treatment with 5 μM $NO_2$-OA revealed that basal GSH levels in MCF-10A cells (19.3±1.9 nmol/$10^6$ cells) was >2-fold that of MDA-MB-231 (8.3±0.8 nmol/$10^6$ cells) and ~1.5-fold greater than MDA-MB-468 cells (12.9±0.5 nmol/$10^6$ cells) (FIG. 7A). GSSG levels (FIG. 7B) at time zero were greater in MCF-10A cells, resulting in an initial GSH:GSSG ratio of 82±16 compared to 653±68 for MDA-MB-231 cells and 2003±163 in MDA-MB-468 cells. MCF-10A cells maintained the GSH:GSSG ratio over the first 6 hr after $NO_2$-OA treatment, whereas the GSH:GSSG ratio rapidly decreased in MDA-MB-231 and MDA-MB-468 cells due to decreased GSH concentrations. In aggregate, the data in FIGS. 6 and 7 support that there will be a more extensive reaction expected between $NO_2$-OA and cellular protein targets in TNBC cells because of the more favorable pharmacokinetics (greater intracellular concentration and longer t0.5) lent by the lower GSH concentrations and the suppression of $NO_2$-OA-SG export by the MRP1-deficient TNBC cell phenotype. In MCF-10A cells $NO_2$-OA will be more readily glutathionylated and exported, thus limiting reactions with signaling pathway proteins.

$NO_2$—OA Inhibits TNFα-Induced TNBC Cell Migration and Invasion.

Figure 8D:
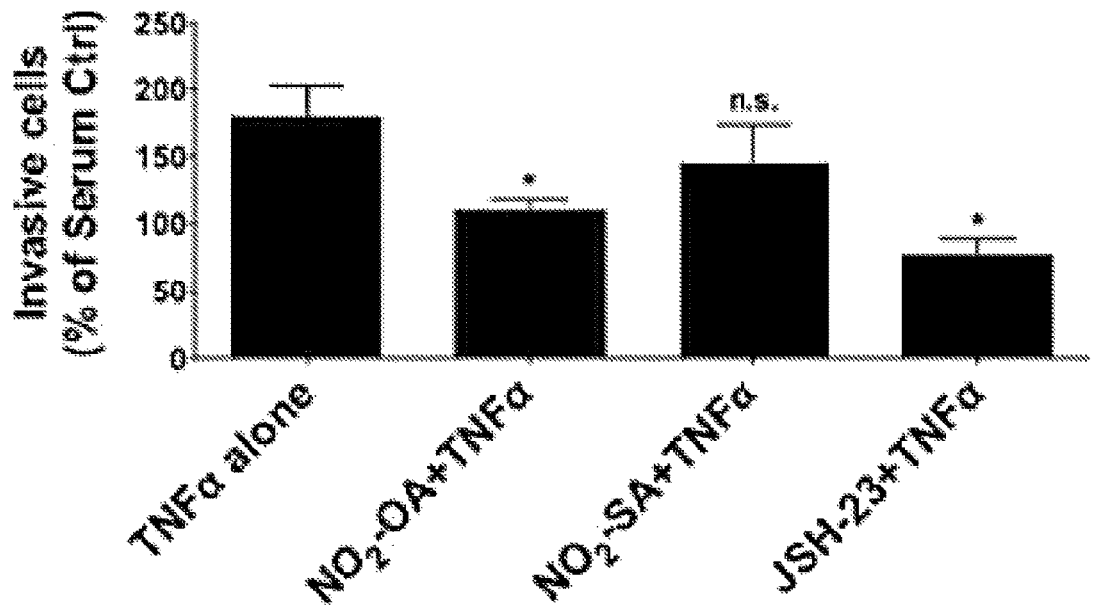

Inflammatory stimuli such as TNFα induce responses in the tumor microenvironment that promote TNBC tumor metastasis and invasion. Since electrophilic $NO_2$—FAs mediate anti-inflammatory signaling actions, the impact of $NO_2$-OA on TNFα-induced TNBC cell migration was evaluated. Boyden chamber migration analyses indicated that TNFα augmented migration of both MDA-MB-231 and MDA-MB-468 cells (FIG. 8A, images 3 and 8), compared to basal conditions (FIG. 8A, image 2 and 7). $NO_2$-OA significantly inhibited both MDA-MB-231 and MDA-MB-468 cell migration induced by TNFα (FIG. 8A, images 4 and 9; FIGS. 5, B and C). $NO_2$-OA modestly inhibited the basal, non-stimulated migration of MDA-MB-231 and MDA-MB-468 cells (FIGS. 8, B and C). Next, cells were placed in transwell permeable supports coated with matrigel for invasion assays to assess the potential effect of $NO_2$-OA on the invasive phenotype of TNBC cells. TNFα-induced invasion was significantly inhibited by $NO_2$-OA treatment of MDA-MB-468 cells, whereas the non-electrophilic control fatty acid ($NO_2$—SA) displayed marginal effects on tumor cell invasion (FIG. 8D). The inhibitory actions of $NO_2$-OA on MDA-MB-468 invasion was compared with cell responses to the NF-κB inhibitor JSH-23, which inhibits nuclear translocation of the RelA subunit. Similar to JSH-23, $NO_2$-OA inhibited TNFα-induced invasion in MDA-MB-468 cells (FIG. 8D).

$NO_2$—OA Inhibits TNFα-Induced NF-κB Transcriptional Activity in TNBC Cells.

The inhibition of MDA-MB-468 cell invasion by JSH-23 (FIG. 8D) suggests that $NO_2$-OA may also inhibit TNFα-induced breast cancer cell mobility due to a capacity to inhibit NF-κB signaling. To test this concept, the effect of $NO_2$-OA on TNFα-activated NF-κB transcriptional activity in TNBC cells was examined. MDA-MB-231 and MDA-MB-468 cells were transiently transfected with an NF-κB luciferase reporter plasmid and treated with 5 μM $NO_2$-OA for 2 hr, followed by activation with 20 ng/mL TNFα for 4 hr. In addition to $NO_2$-OA, the non-electrophilic lipid controls $NO_2$—SA (5 μM) and OA (5 μM) were also examined. $NO_2$-OA significantly inhibited NF-κB-dependent transcription of luciferase in both TNBC cell lines, compared with TNFα alone, while $NO_2$—SA and OA had no effect. Moreover, the extent of inhibition of NF-κB-dependent luciferase expression by $NO_2$-OA was similar to that induced by the NF-κB inhibitor JSH-23 (20 μM; FIGS. 9, A and B). These data indicate that the electrophilic reactivity of $NO_2$-OA accounts for the inhibition of TNFα-induced NF-κB transcriptional activity in TNBC cells.

$NO_2$-OA Inhibits NF-κB-Regulated Gene Expression Linked with TNBC Tumor Metastasis.

Figure 9E:
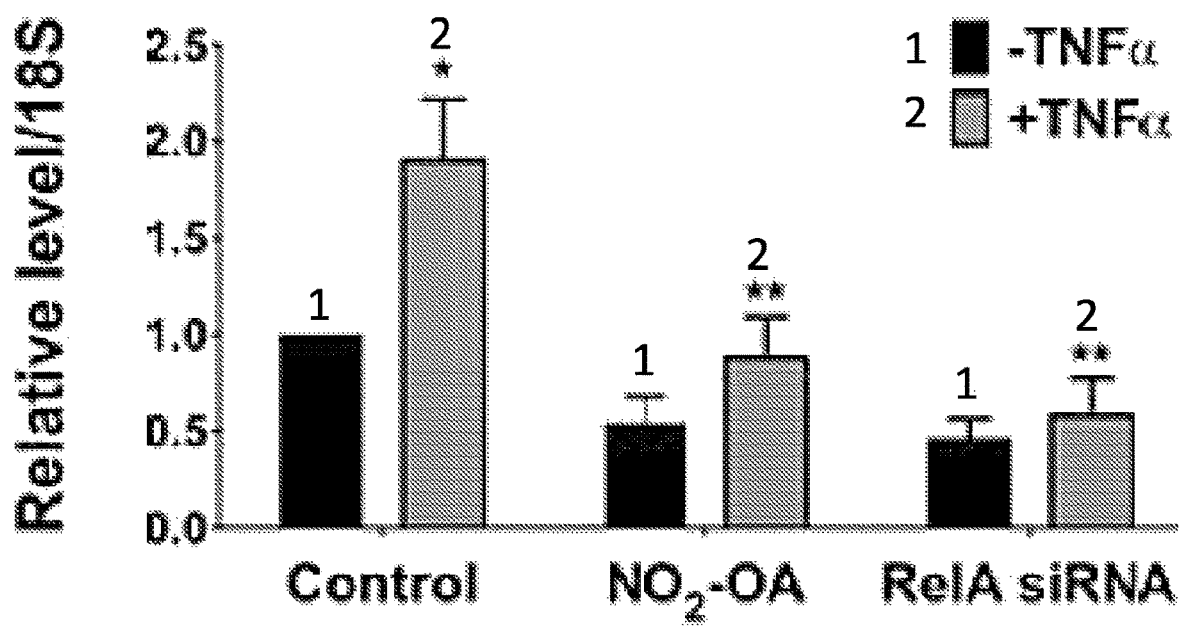

Inhibition of NF-κB transcriptional activity by $NO_2$-OA suggested that the expression of metastasis-related downstream target genes may be decreased. To investigate this, key NF-κB target genes were evaluated via RT2 profiler PCR array analysis of MDA-MB-468 cells treated with $NO_2$-OA (5 μM) for 24 hr. The expression levels of NF-κB target genes that were regulated by $NO_2$-OA were compared to MDA-MB-468 untreated control cells. Data revealed that treatment with $NO_2$-OA decreased the mRNA expression of multiple NF-κB target genes, including ICAM-1 and uPA, two critical mediators of tumor progression and metastasis (FIG. 9C). TNFα induces the expression of both ICAM-1 and uPA in MDAMB-231 cells (37,38). To more directly examine whether $NO_2$-OA suppressed TNFα-induced expression of ICAM-1 and uPA in TNBC cells, MDA-MD-231 or MDA-MD-468 cells were treated with 5 μM $NO_2$-OA and 20 ng/mL TNFα. Simultaneous treatment with either $NO_2$-OA or RelA siRNA led to suppression of TNFα-induced expression of ICAM-1 and uPA genes in TNBC cells (FIG. 9D, 9E; 9G, 9H). The impact of $NO_2$-OA and RelA siRNA on RelA-dependent target gene expression was further evaluated by qRT-PCR (FIG. 9F; 9I). RelA mRNA levels were suppressed by RelA siRNA treatment, but not $NO_2$-OA. Both $NO_2$-OA and RelA siRNA inhibited gene expression of TNFα-induced ICAM-1 and uPA gene expression via NF-κB-dependent mechanisms. To determine whether $NO_2$-OA suppressed TNFα-induced pro-metastatic ICAM-1 and uPA gene expression during cell migration, transcript levels of ICAM-1 and uPA genes were evaluated in MDA-MB-468 cells being studied in Boyden chamber migration assays (FIG. 8C). Under these conditions, $NO_2$-OA significantly inhibited TNFα-induced expression of ICAM-1 and uPA in migrating tumor cells, again supporting that $NO_2$-OA inhibited expression of NF-κB-regulated genes involved in metastasis.

$NO_2$—OA Suppresses TNFα-Induced IKKβ/IκBβ Signaling in TNBC.

To better define mechanisms accounting for $NO_2$-OA inhibition of TNFα-activated NF-κB signaling, MDA-MB-231 or MDA-MB-468 cells were pretreated with $NO_2$-OA (5

μM) or the IKK inhibitor BAY11-7082 (10 μM) for 2 hr before TNFα stimulation (20 ng/mL, 5 min).

Figure 10B:
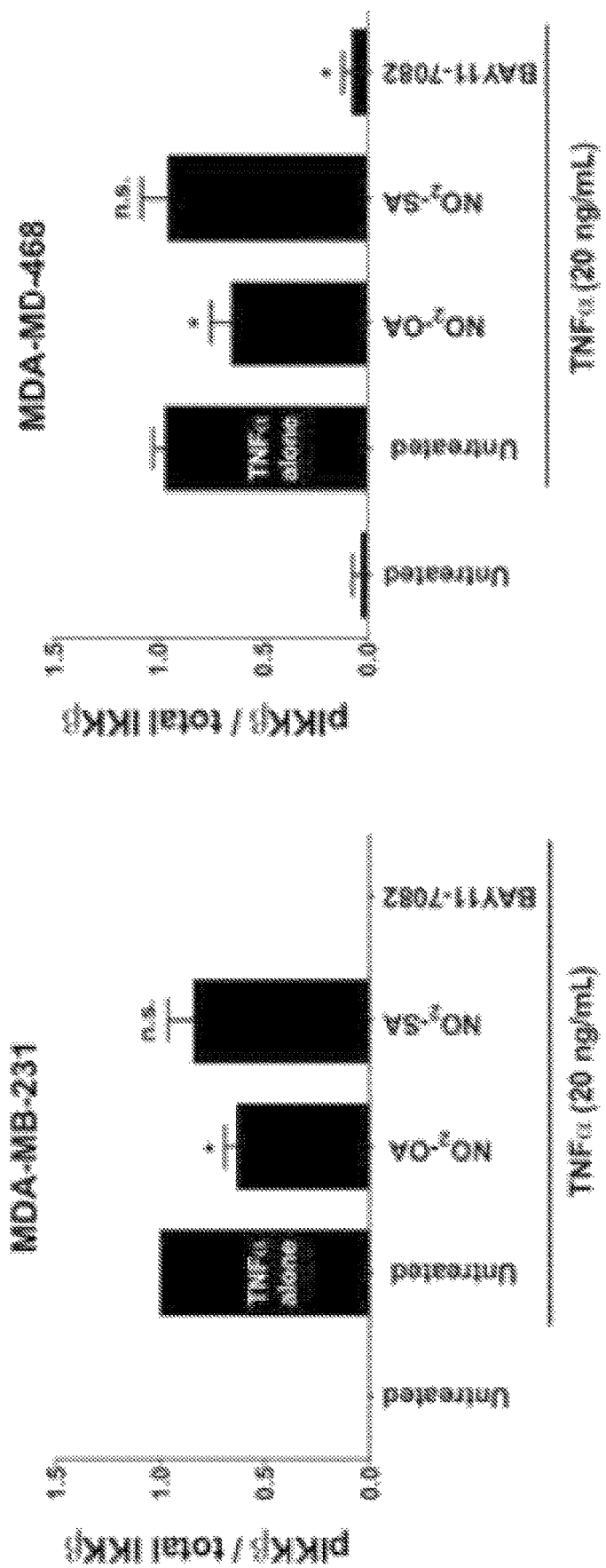

TNFα-induced IKKβ phosphorylation was diminished by both $NO_2$-OA and BAY11-7082 (FIG. 10A). Both $NO_2$-OA and BAY11-7082 also inhibited the degradation of IκBβ following TNFα stimulation (20 ng/mL, 10 min, FIG. 10B). Moreover, decreased IκBβ phosphorylation occurred in cells pretreated with $NO_2$-OA or BAY11-7082 and the proteasome inhibitor MG-132 (10 μM, FIG. 7C). This indicates that $NO_2$-OA suppresses TNFα-induced IKKβ phosphorylation and IκBβ degradation, with these actions in turn inhibiting downstream NF-κB signaling in TNBC cells.

$NO_2$—OA Alkylates IKKβ and RelA Proteins.

Figure 10C:
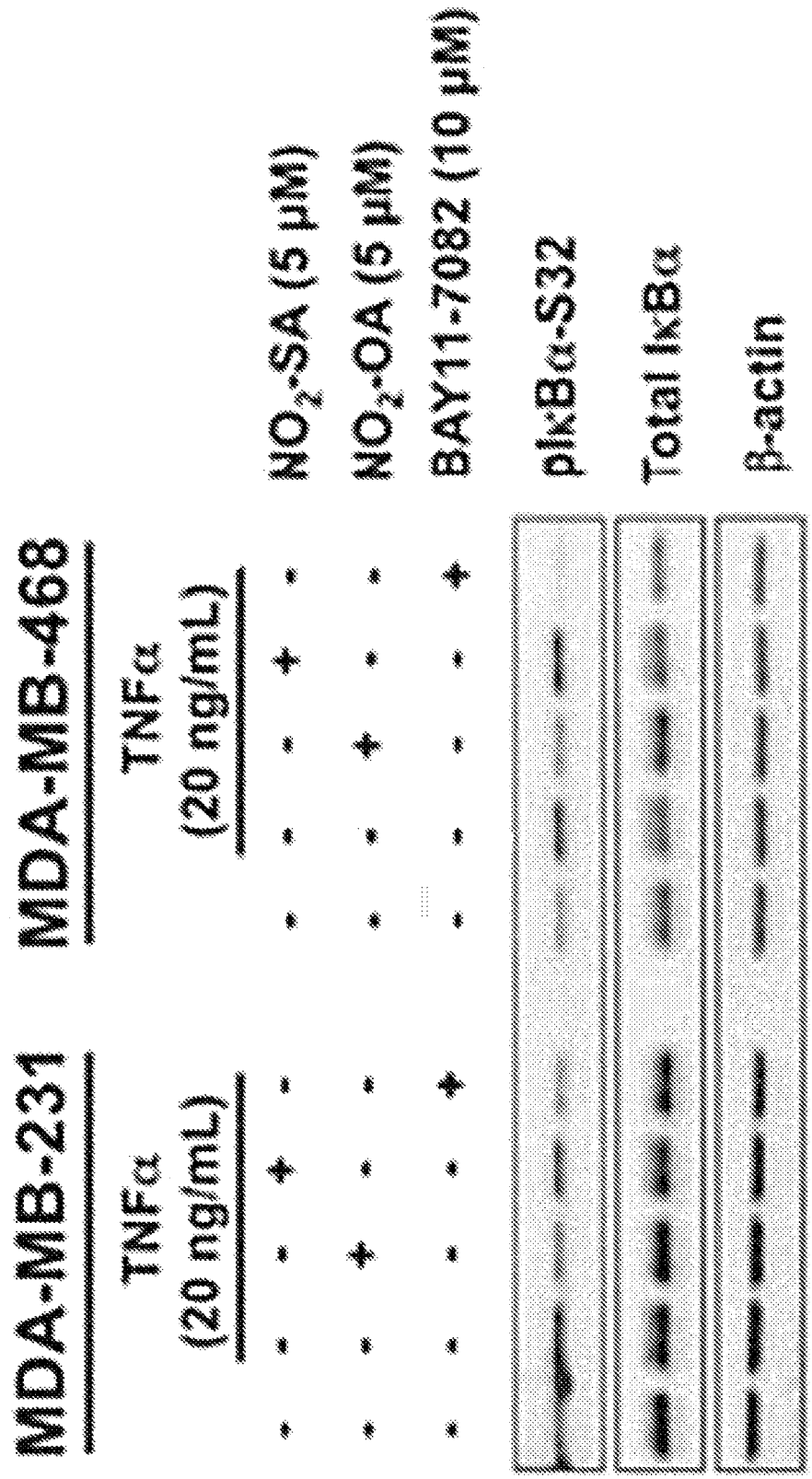
Figure 10D:
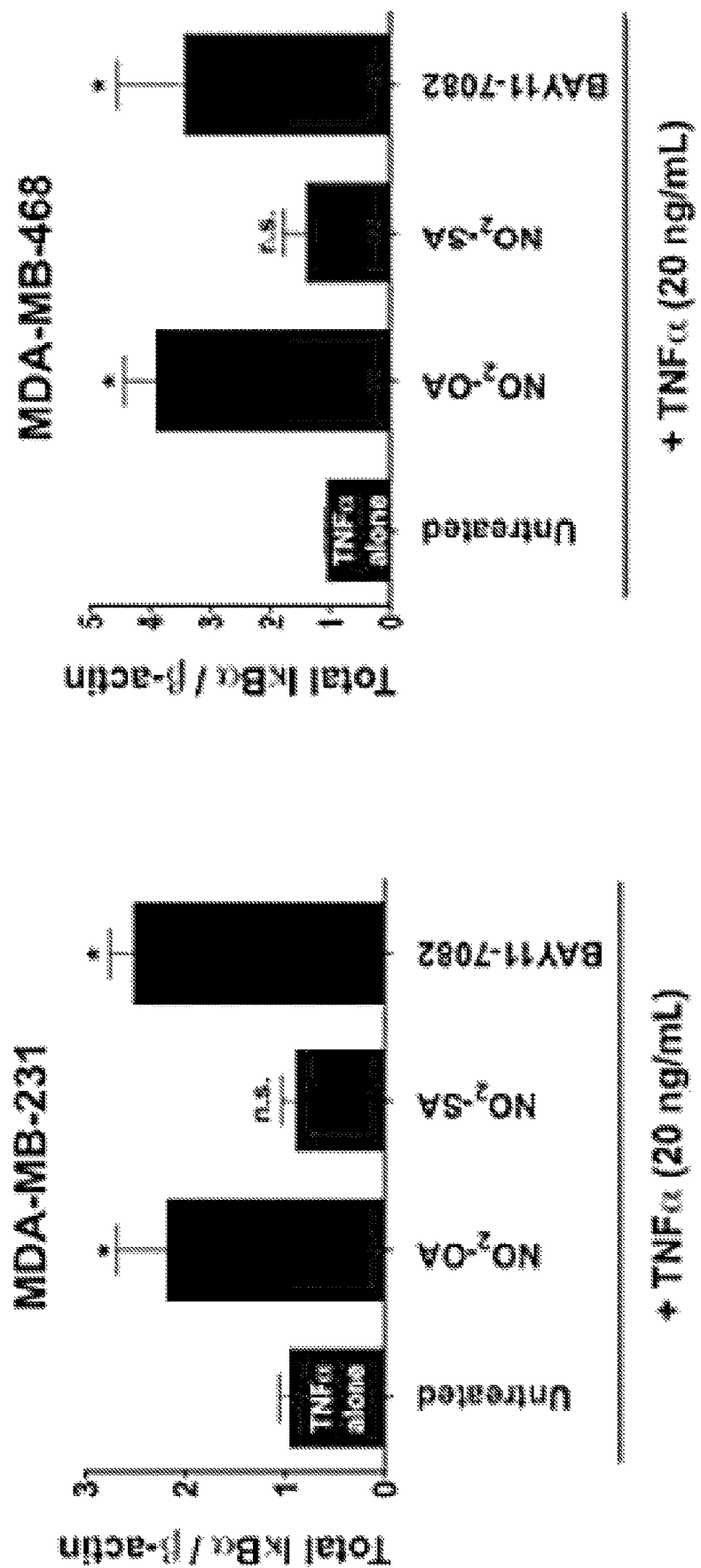
Figure 10E:
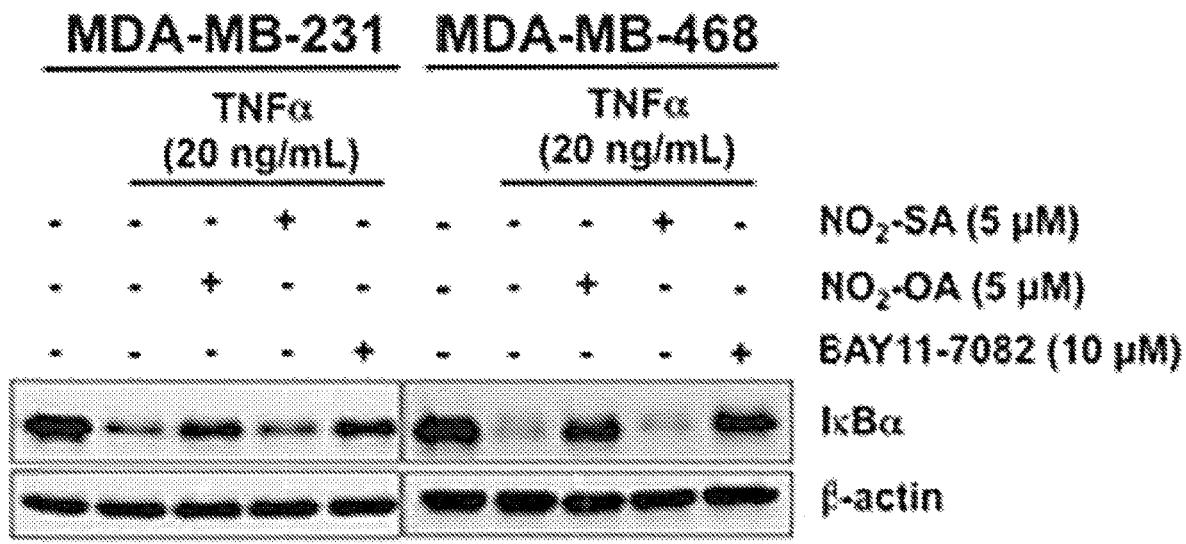
Figure 10F:
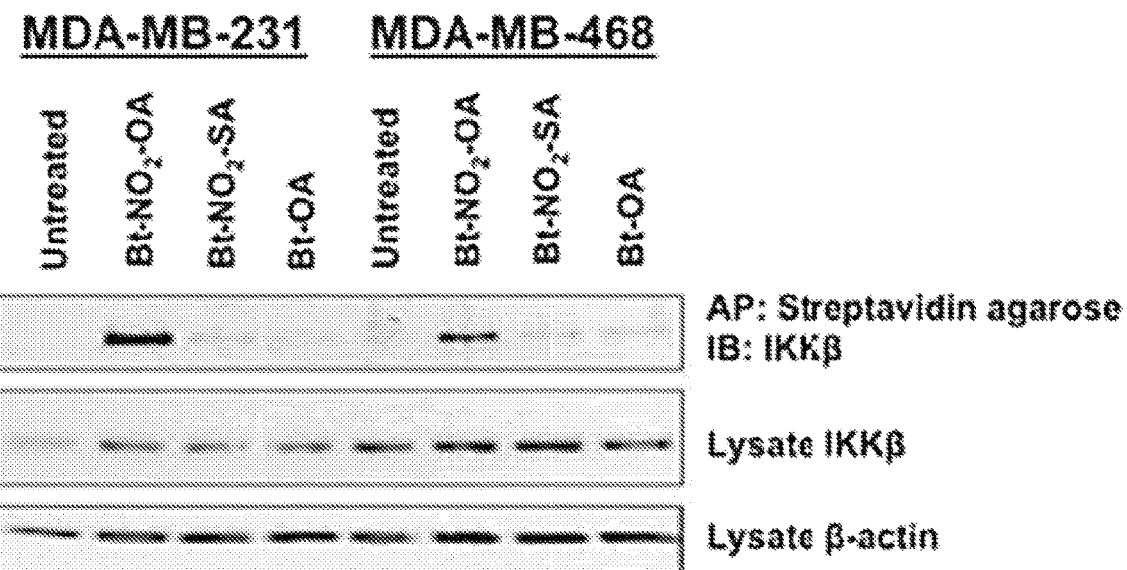
Figure 11A:
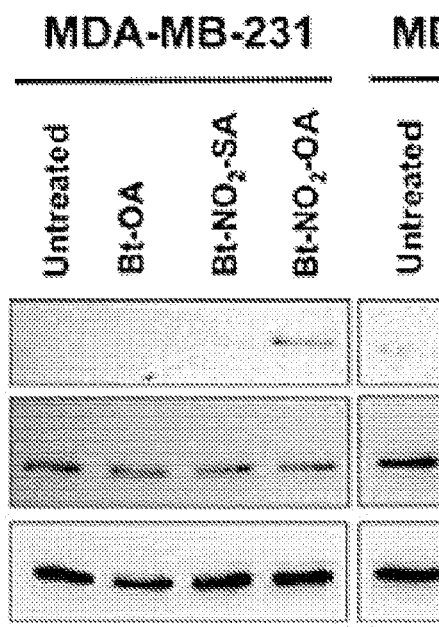

Cys179, located in the activation loop of IKKβ, is a target for oxidation and electrophile alkylation reactions. Because $NO_2$-OA suppresses TNFα-induced phosphorylation of IKKβ and IKKβ in TNBC cells (FIG. 10A, 10C), the potential for $NO_2$-OA to directly modify IKKβ was investigated. Biotinylated lipids (Bt-$NO_2$-OA, Bt-$NO_2$—SA, and Bt-OA) were synthesized to facilitate affinity capture-mediated measurement of $NO_2$-OA and control fatty acid adduction of IKKβ. MDA-MB-231 or MDA-MB-468 cells were treated with 5 μM Bt-$NO_2$-OA, Bt-$NO_2$-SA, or Bt-OA for 2 hr and then all alkylated proteins were pulled down from whole-cell lysates using streptavidin-conjugated beads. Western blotting revealed that IKKβ was pulled down by Bt-$NO_2$-OA, but not by non-electrophilic control fatty acids (FIG. 10D). Similarly, Bt-$NO_2$-OA (but not control fatty acids) promoted the pull-down NF-κB RelA (FIG. 11A). $NO_2$-OA inhibits LPS-induced NF-κB transcriptional activity, in part a consequence of the alkylation of RelA Cys38 and inhibition of RelA DNA binding. LC-MS/MS proteomic analysis showed that RelA Cys105 was also alkylated by $NO_2$-OA, with the functional significance of the $NO_2$-OA alkylation of RelA Cys105 undefined. In aggregate, Bt-$NO_2$-OA promotes the pull-down of IKKβ and RelA, and direct proteomic analysis revealed the $NO_2$-OA alkylation of RelA. These observations underscore that $NO_2$-OA mediates PTMs that inhibit multiple facets of proinflammatory NF-κB signaling.

$NO_2$—OA Stimulates RelA Protein Proteasomal Degradation.

Figure 11B:
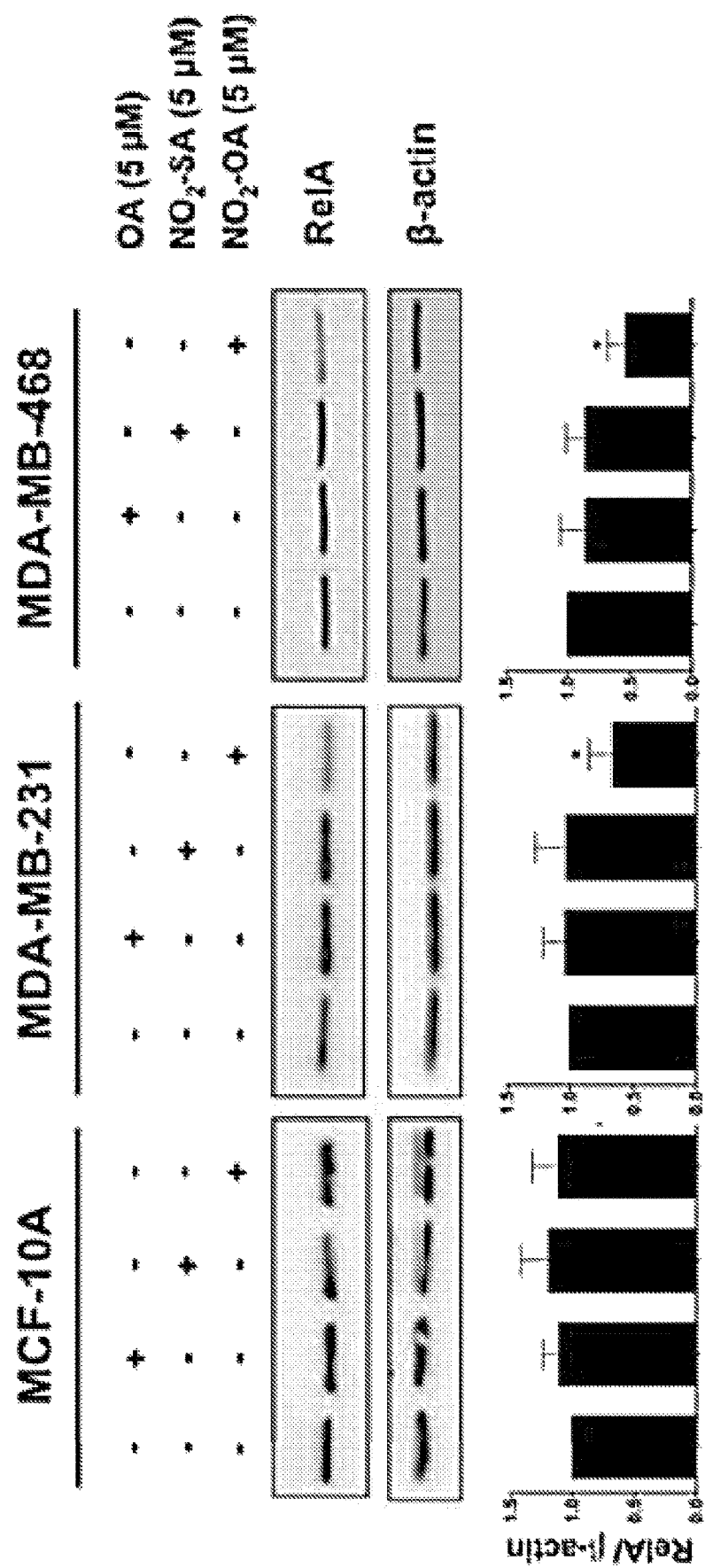
Figure 11C:
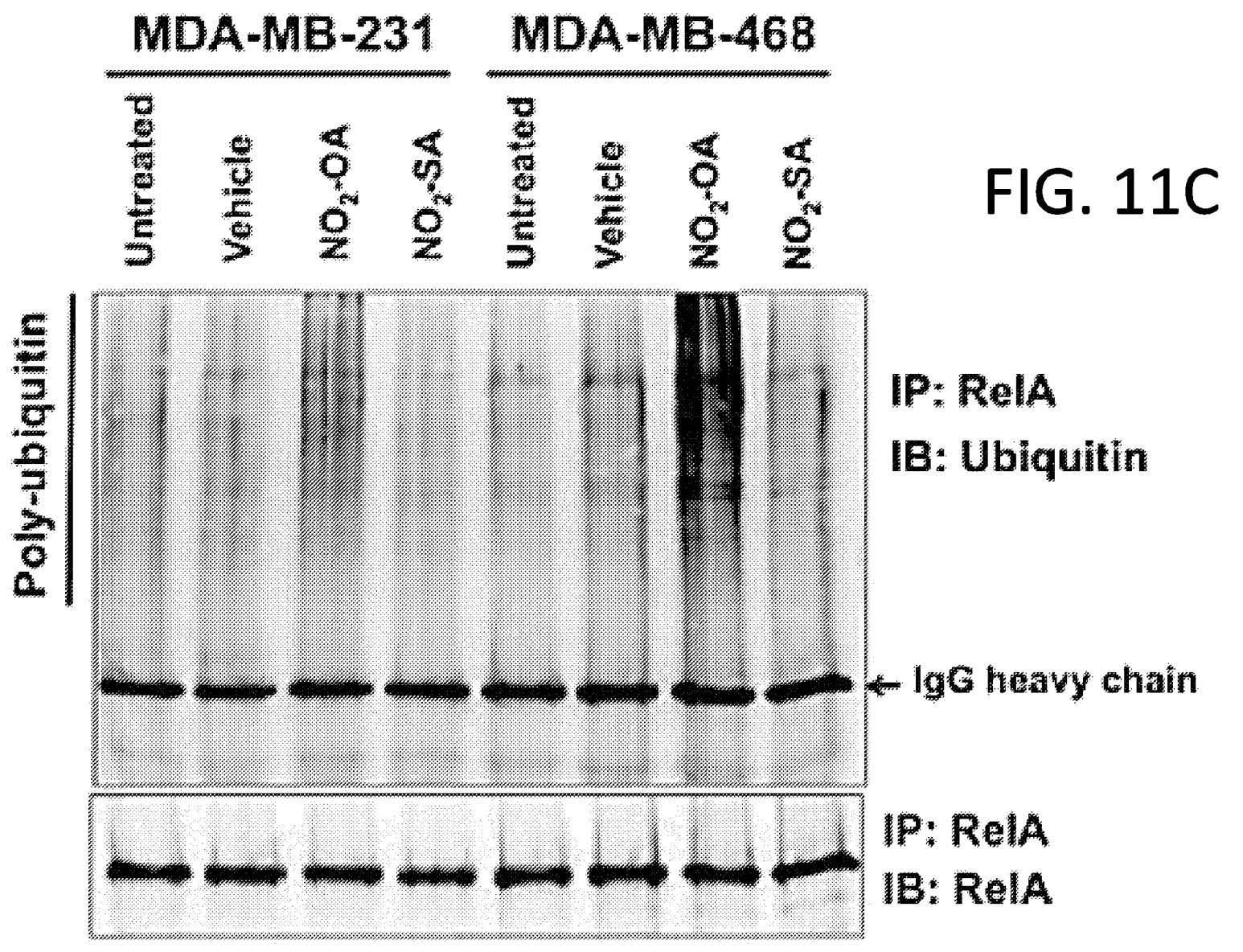

Proteolytic degradation of NF-κB contributes to the termination of its signaling. Thiol-alkylating and nitrosating agents induce the degradation of NF-κB subunit p50 via the PTM of Cys62 in both HT29 and HCT116 tumor cell lines. Since $NO_2$-OA covalently adducts RelA in both MDA-MB-231 and MDA-MB-468 cells (FIG. 11A), the consequence of $NO_2$-OA PTMs on RelA protein stability was investigated. To validate this putative mechanism, we first examined whether endogenous RelA protein expression responded to $NO_2$-OA. MDA-MB-231, MDA-MB-468, and MCF-10A cells were treated with 5 μM $NO_2$-OA or control lipids ($NO_2$—SA and OA) for 24 hr. $NO_2$-OA decreased the abundance of RelA in TNBC cells, while $NO_2$—SA and OA had no effect (FIG. 11B). In contrast, RelA protein levels in MCF-10A cells were not altered by $NO_2$-OA (FIG. 11B). In all three cell lines, RelA mRNA levels were not altered by $NO_2$-OA. These data support that $NO_2$-OA impacts RelA protein stability via alkylation of RelA in TNBC cells. RelA is regulated by ubiquitin- and proteasome-dependent degradation signals that govern NF-κB activation. To determine whether RelA modification by $NO_2$-OA induced ubiquitination of endogenous RelA in TNBC cells, MDA-MB-231 or MDA-MB-468 cells were treated with 5 μM $NO_2$-OA or $NO_2$-SA for 5 hr. RelA protein was immunoprecipitated and its polyubiquitination was detected by anti-ubiquitin. $NO_2$-OA, but not $NO_2$-SA, promoted polyubiquitination of RelA in both TNBC cell lines (FIG. 11C). This indicates that $NO_2$-OA interacts with RelA, destabilizes RelA protein by promoting ubiquitination and proteasomal degradation in TNBC cells.

Structure Function Relationships of Electrophilic Nitro Fatty Acid Regioisomers in the Inhibition of HDR and Lethality Towards TNBC Cell Lines.

Figure 12A:
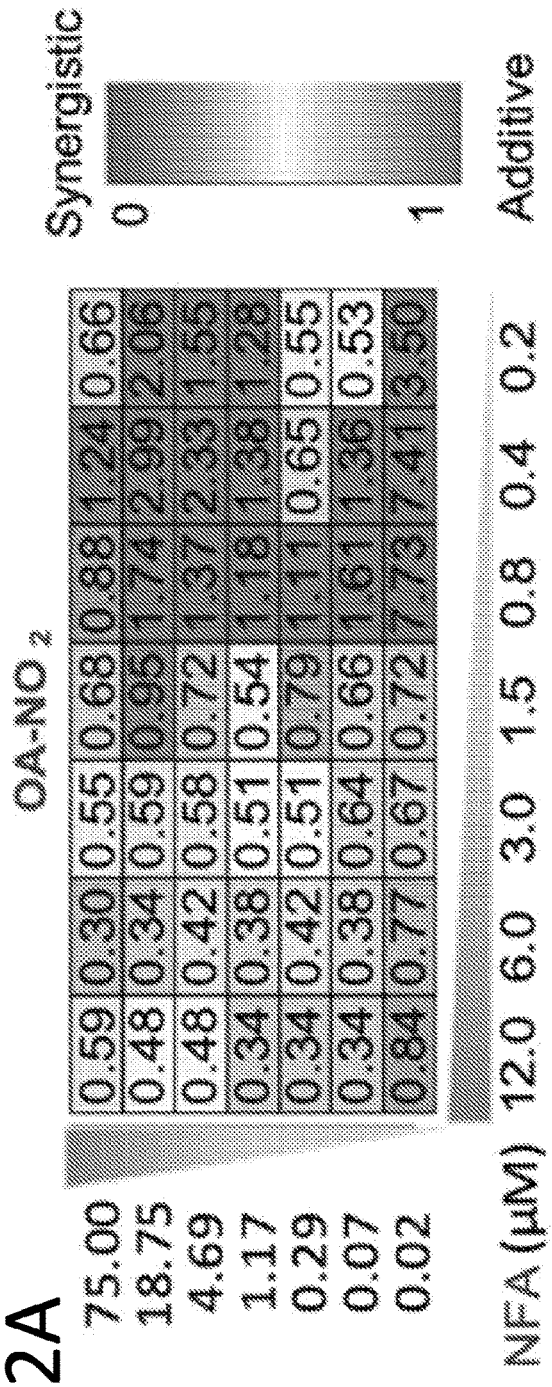
FIGS. 12A-12B. Determination of combination index. Growth inhibition (relative cell numbers) of MDA-MB-231 cells treated with talazoparib (0.01-75 μM) plus OA-$NO_2$ (FIG. 12A) and 7-NDA (FIG. 12B) (0.2-12 μM) daily for a total of 3 days, was determined by luminescent detection of ATP (CellTiter-Glo). Combination index (CI) was calculated by the Chou-Talalay method (17). CI<1 is synergistic. Mean from 3 independent experiments. 7-NDA has better CI values compared to OA-$NO_2$. Both improve standard chemotherapy (PARPi, radiation, doxorubicin, platins) either additively or synergistically to kill TNBC tumor cells.
Figure 12B:
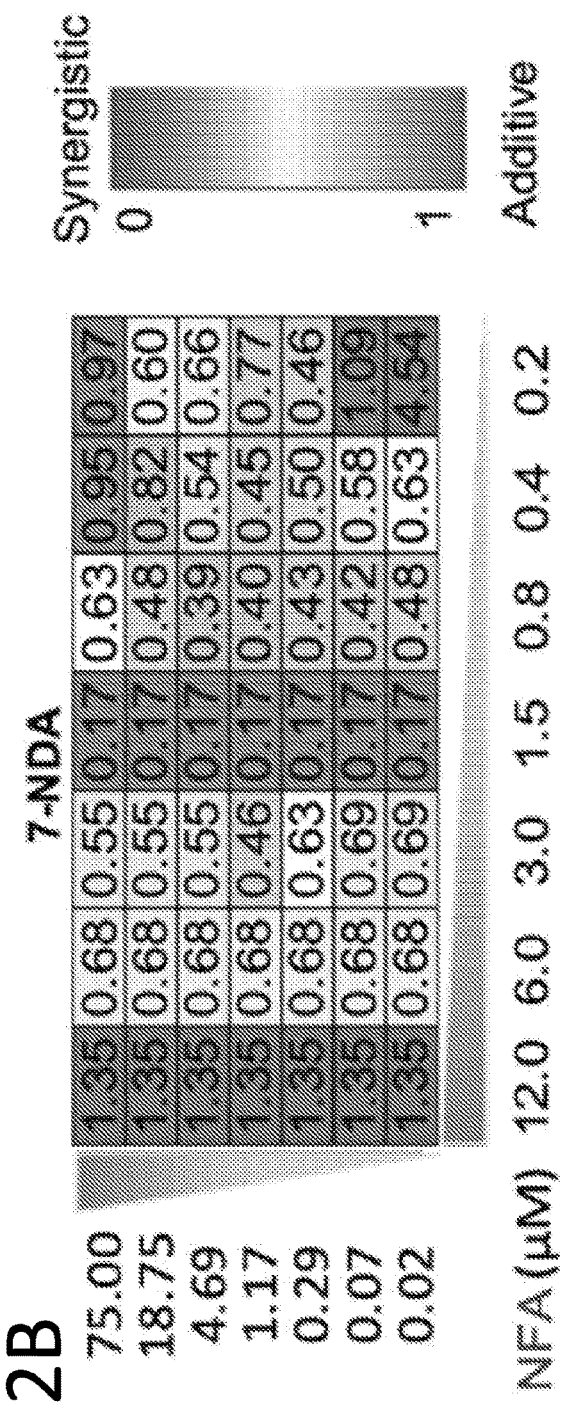
Figure 13B:
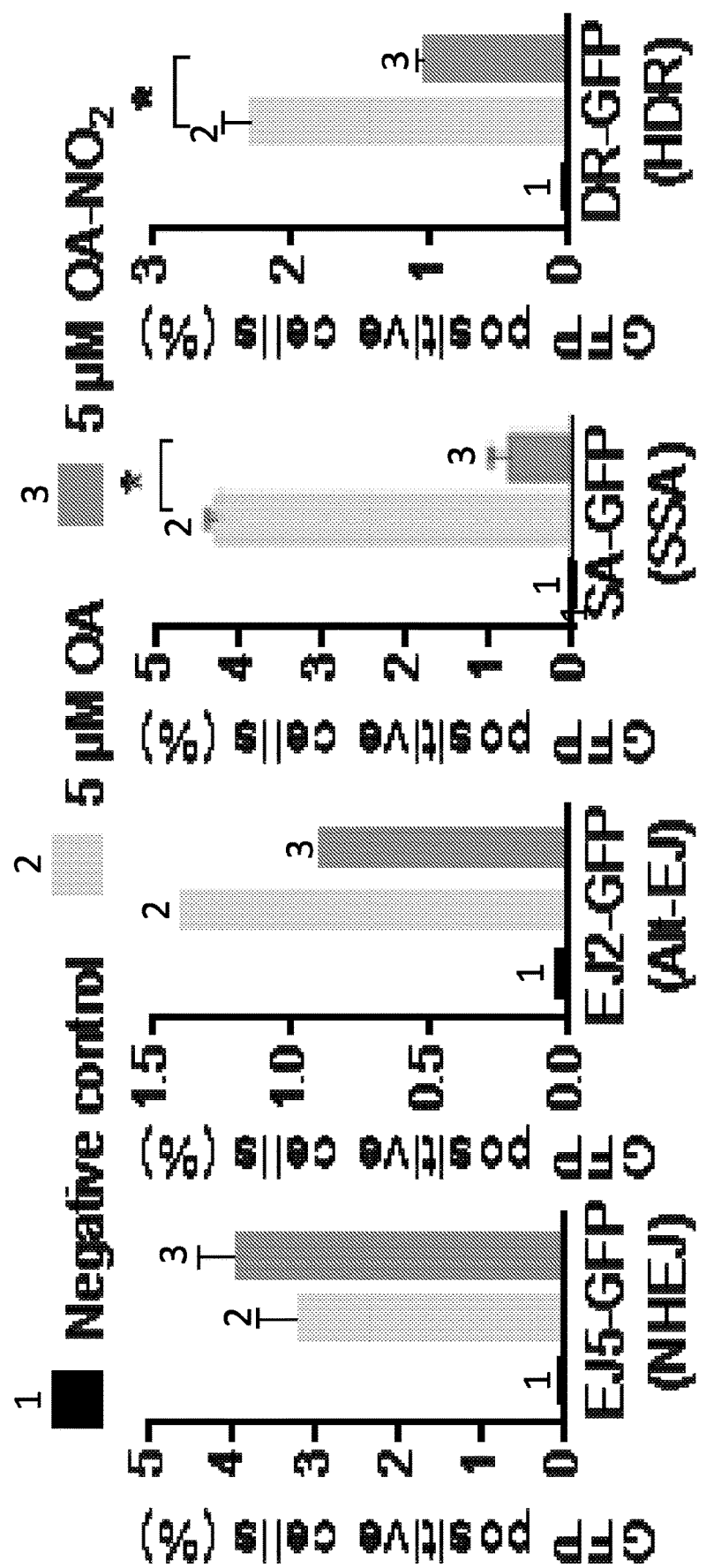
FIG. 13B is GFP-reporter assays examining effects of OA-$NO_2$ on different DNA DSB repair pathways described in FIG. 14A. U2OS cells containing the GFP-reporter construct DR-GFP were transfected with an I-SceI plasmid and treated with vehicle (gray), 5 μM OA (green) or 5 μM OA-$NO_2$ (red). The number of GFP positive cells were detected by flow cytometry at 48 h. GFP-reporter measuring NHEJ: n=3, SSA: n=3; HDR: n=3; Alt-EJ: n=1.

Computational analysis of the crystal structure of Rad51 suggests that repositioning the nitroalkene substituent in nitroalkene fatty acids closer to the C-terminus enhances Rad51 protein binding via hydrogen bond stabilization of a carboxyl group vicinal to the Cys319 residue. Based on this analysis, we designed 7-NDA (7-$NO_2$-nonadec-7-enoic acid). 7-NDA shows a lower $IC_{50}$ compared $NO_2$-OA and better combination indices when combined with talazuparib (FIG. 12).

Figure 14:
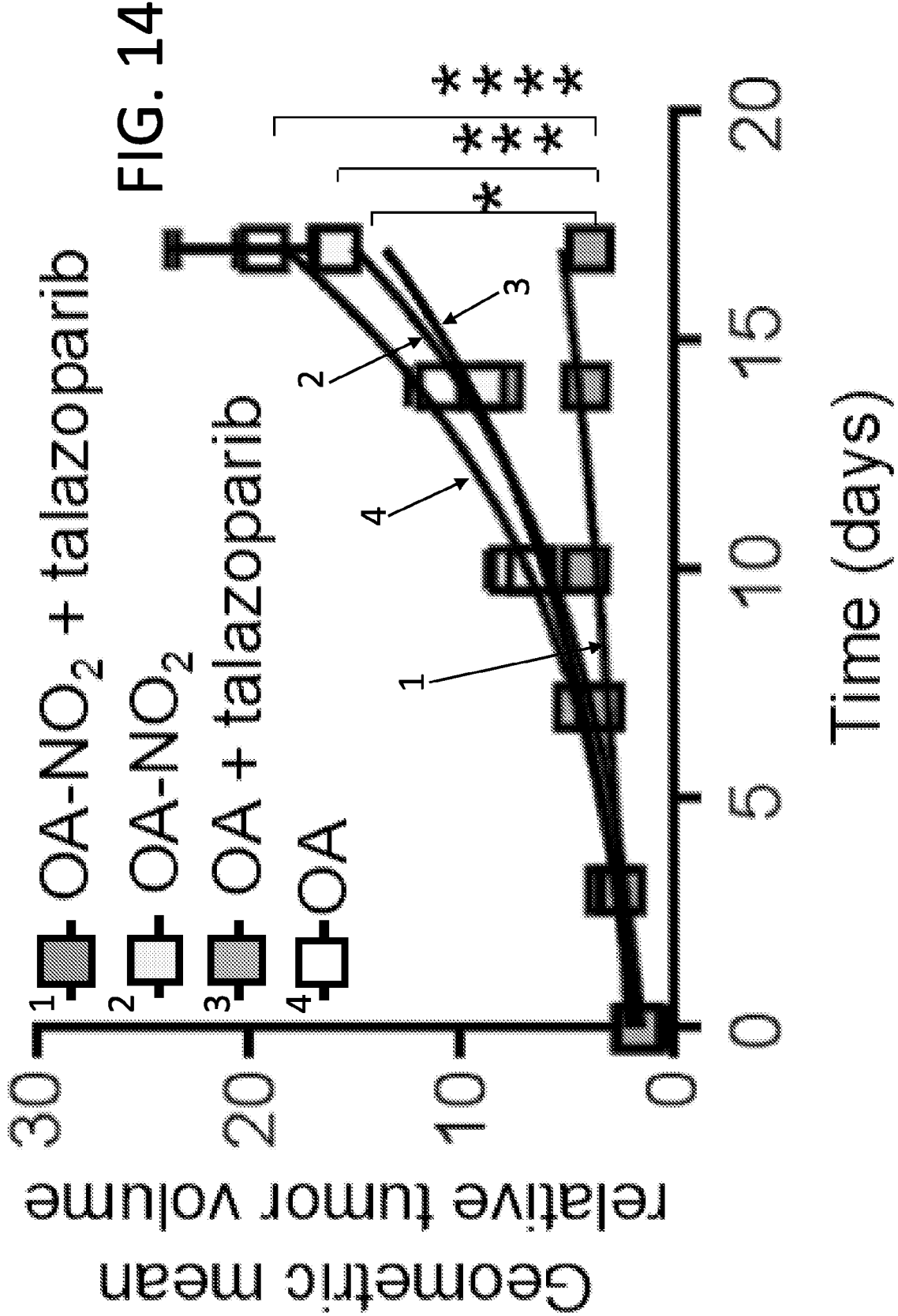
FIG. 14. Tumor volume by combination of $NO_2$-OA with talazoparib. MDA-MB-231 cells were orthotopically injected in the mammary fat pad of nude mice. Tumor volume was measured by caliper over time in mice treated with OA (15 mg/kg)+vehicle (n=8), $NO_2$-OA (15 mg/kg)+vehicle (n=7), OA+talazoparib (0.3 mg/kg) (n=10) or $NO_2$-OA (15 mg/kg)+talazoparib (0.3 mg/kg).
Figure 15:
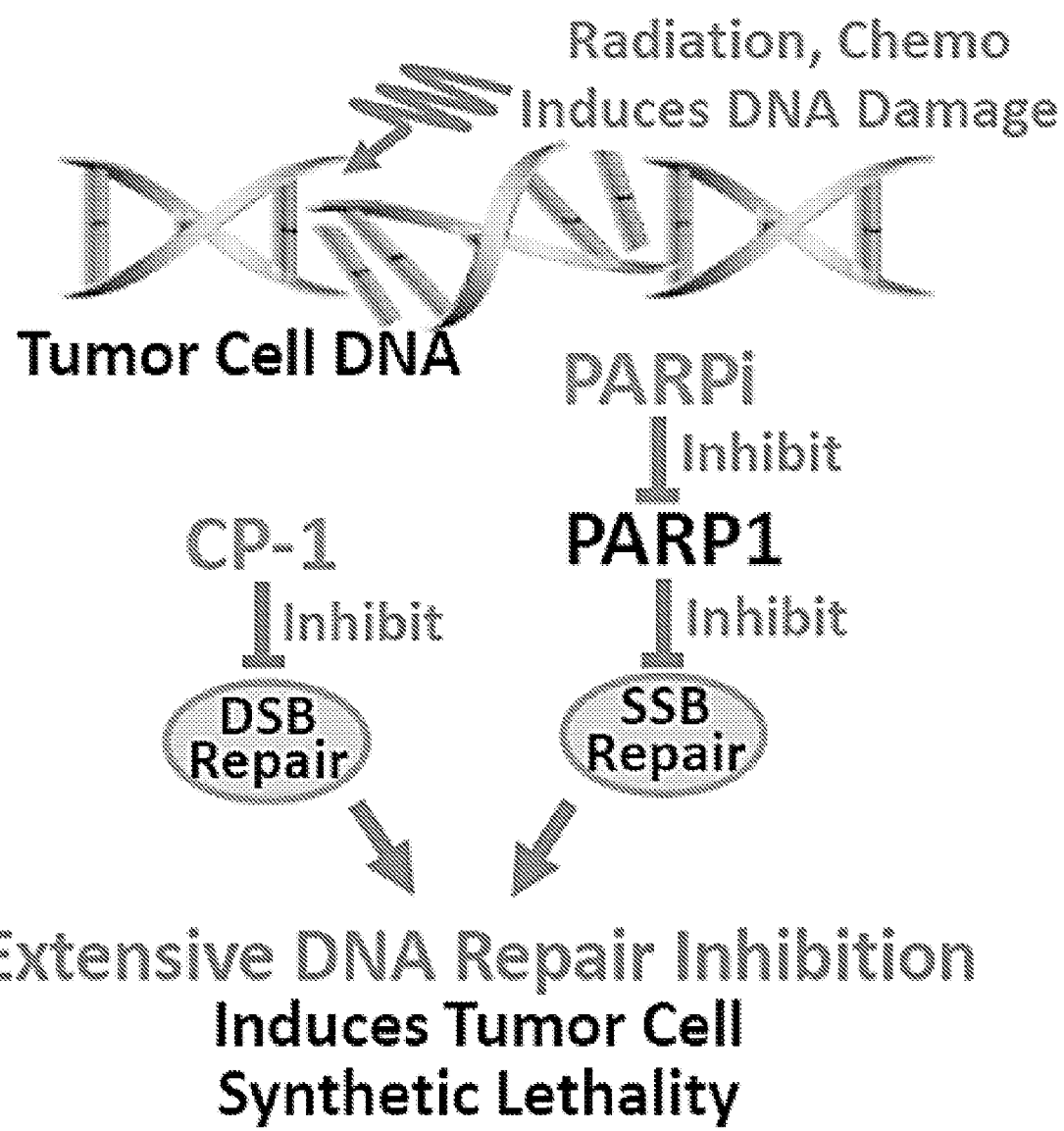
FIG. 15 depicts a scheme of the synthetic lethality concept where a nitroalkene (e.g., CP-1) and a PARP inhibitor are combined. Tumor cells have hyper-active DNA repair mechanisms and CP-1 inhibits double strand DNA break repair (homologous recombination). In combination with a PARP inhibitor of single strand DNA break repair CP-1+ PARPi in combination induces synthetic lethality. This occurs by inhibiting both DSB and SSB repair.
Figure 17A:
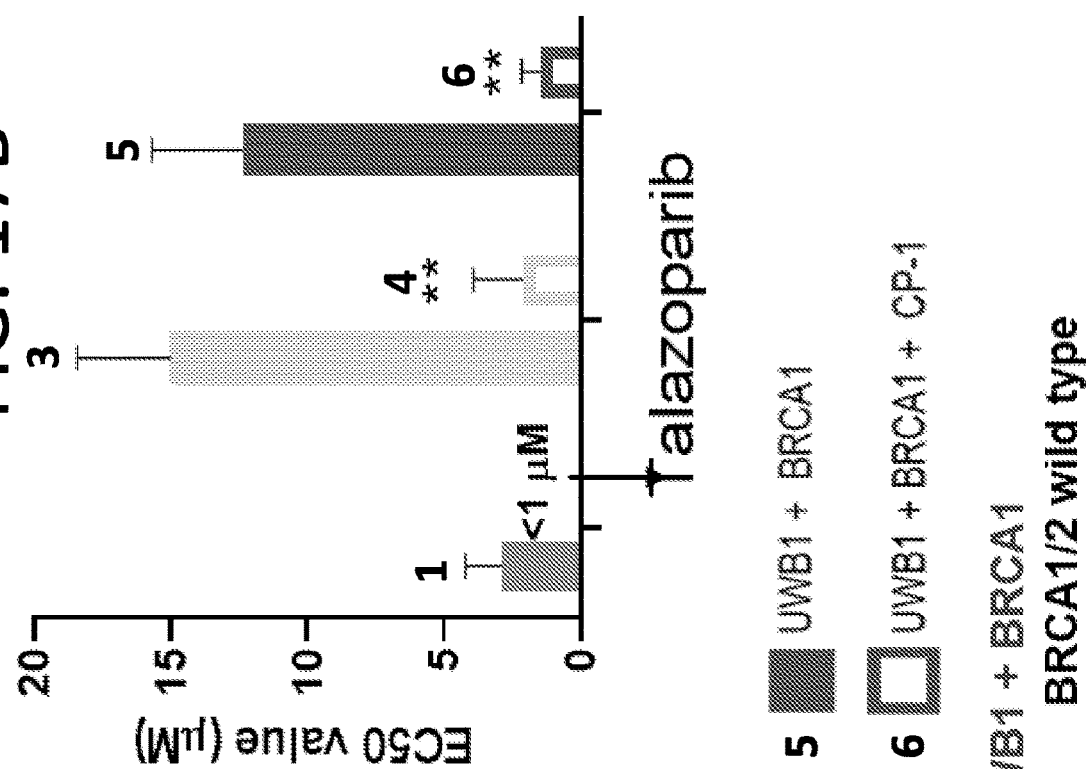
FIGS. 17A and 17B are graphs showing that CP-1 sensitizes human high grade serous ovarian cancer cells to PARP inhibitors and lowers the concentration of the PARP inhibitors Olaparib (FIG. 17A) and Talazoparib (FIG. 17B) needed for 50% tumor cell killing. Cell growth/viability is determined from luminescent detection of cell ATP concentration.
Figure 17B:
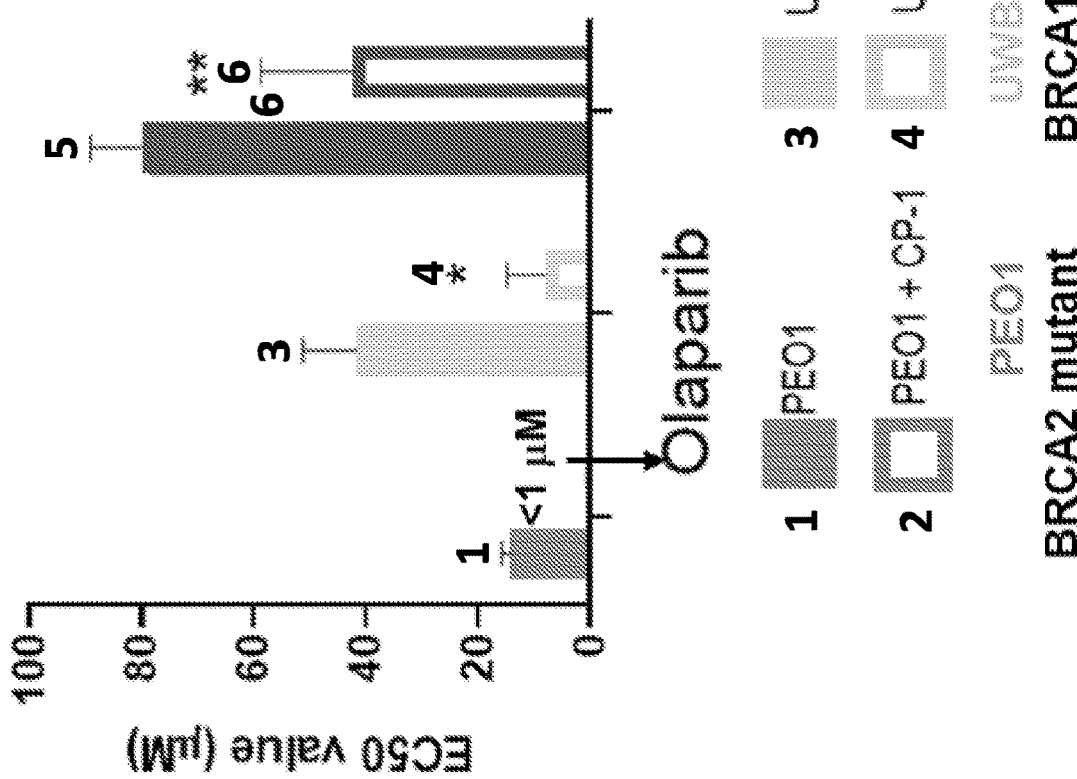
Figure 18:
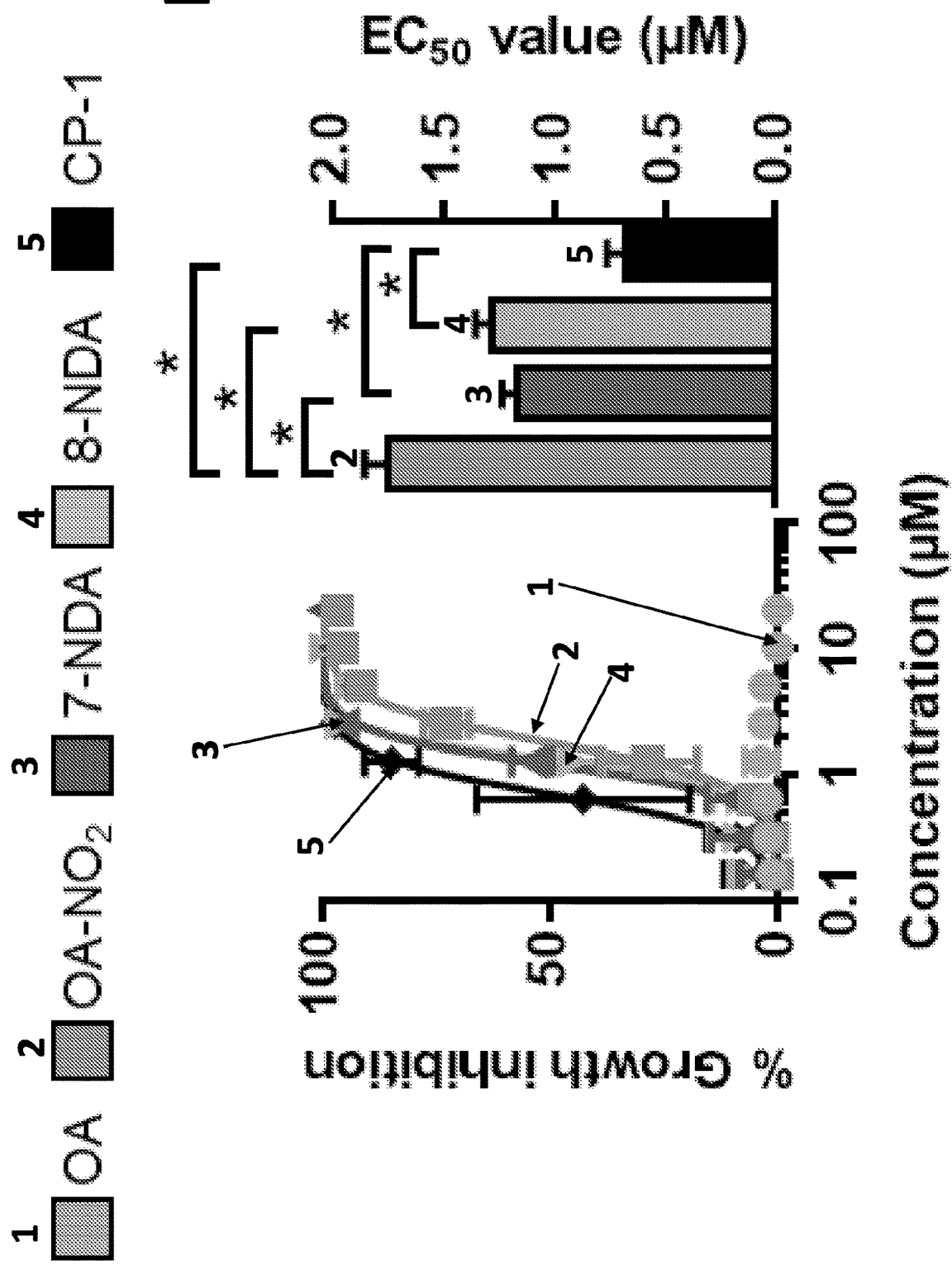
FIG. 18. MDA-MB-231 TNBC cells are more sensitive to 7-NDA and 8-NDA when compared to OA-$NO_2$. Growth inhibition was assessed using the ATP Celltiter Glo proliferation assay and compounds were used at different concentration to determine their EC50. CP-1 had the lowest EC50 followed by 7-NDA and 8-NDA. OA-$NO_2$ had a higher EC50 and OA did not induce any growth inhibition (n=3). The different metabolic pathways of 7-NDA and 8-NDA have been characterized in MDA-MB-231 TNBC cells. MDA-MB 231 TNBC cells incorporate and metabolize 7-NDA and 8-NDA through beta oxidation (FIG. 19). Inactivation of the active 7-NDA and 8-NDA nitroalkene group is achieved through reduction to a nitroalkane (FIG. 20). Further metabolism includes reaction with glutathione and formation of cysteine adducts FIG. 21) and omega hydroxylation and carboxylation (FIG. 22).
Figure 19:
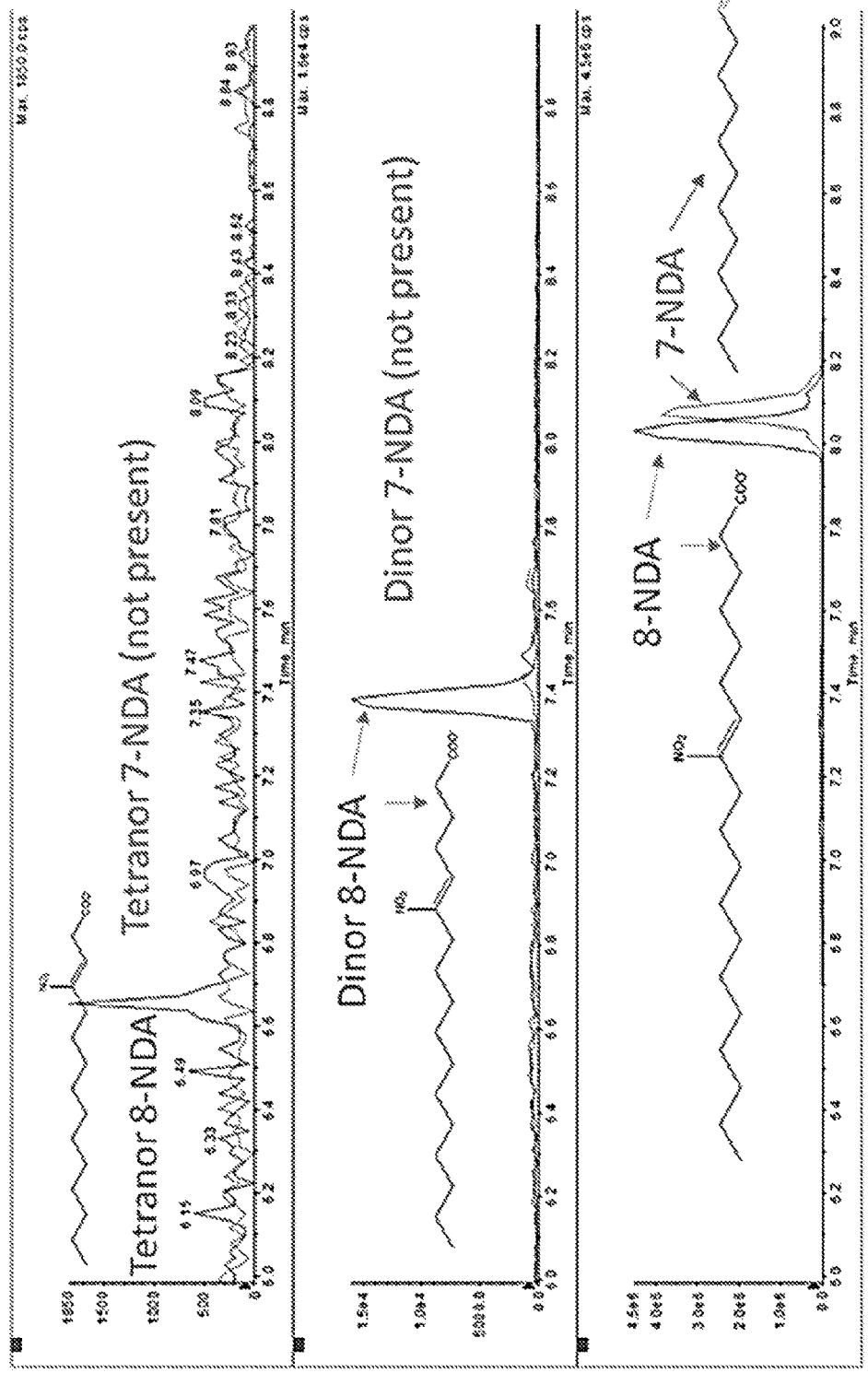
FIG. 19. Treatment of MDA-MB 231 TNBC cell with 7-NDA does not result in the formation of active, nitroalkene containing metabolites as assessed by following the formation of dinor and tetranor 7-NDA. Dinor 7-NDA corresponds to one beta-oxidation cycle while tetranor corresponds to two beta oxidation cycles. In contrast, treatment with 8-NDA result in the active (structures having the reactive nitroalkene moiety) beta-oxidation products. Formation of both Dinor and Tetranor 8-NDA are shown. Chromatograms correspond to the detection by HPLC-MSMS of the different compounds in negative ion mode using MRMs on a triple quadrupole mass spectrometer.
Figure 20:
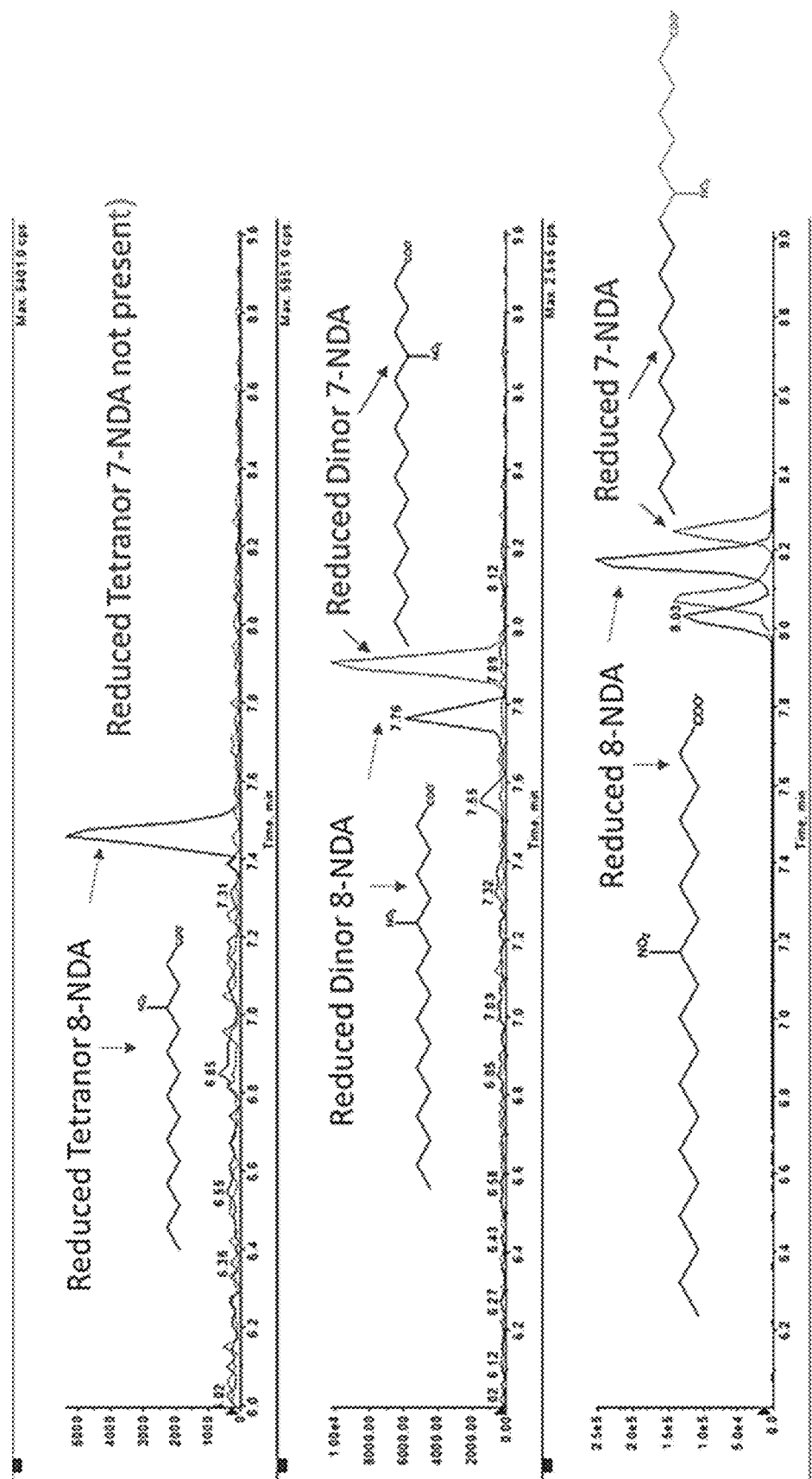
FIG. 20. MDA-MB 231 TNBC cells inactivate both 7-NDA and 8-NDA to form the reduced 7-NDA and reduced 8-NDA respectively. Evidence for the formation of reduced tetranor 8-NDA was obtained while no formation of reduced tetranor 7-NDA was observed. Chromatograms correspond to the detection by HPLC-MSMS of the different compounds in negative ion mode using MRMs on a triple quadrupole mass spectrometer.
Figure 21:
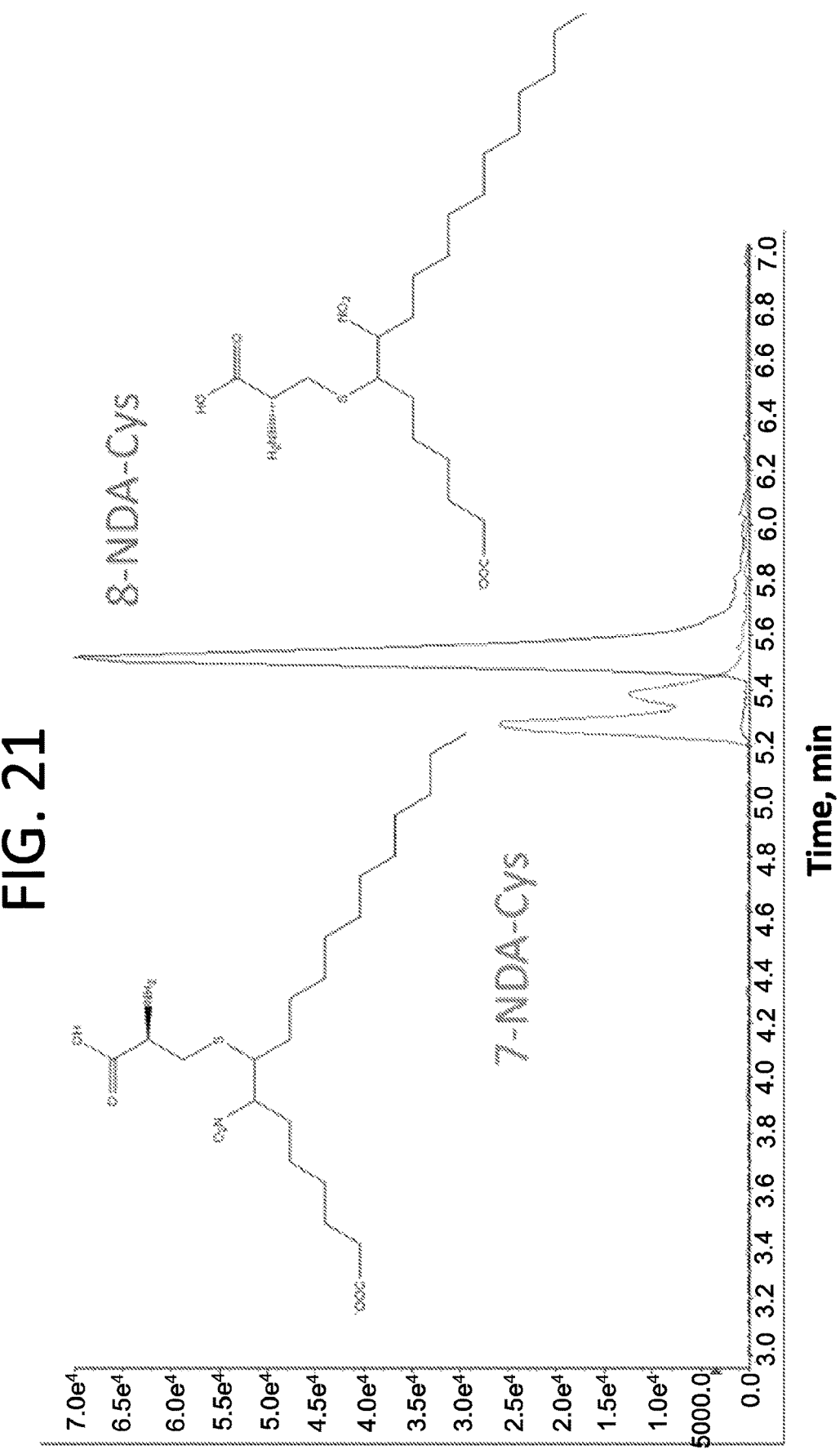
FIG. 21. MDA-MB 231 TNBC cells metabolize both the 7-NDA and 8-NDA to form cysteine adducts that are detected in cell media and cell homogenate. Chromatograms FIG. 22. MDA-MB 231 TNBC cells metabolize both the 7-NDA and 8-NDA through omega hydroxylation and carboxylation. Dicarboxylic acids of both 7-NDA and 8-NDA have been detected in cell media and cell homogenate from cell treated with 10 uM 7-NDA or 8-NDA. Chromatograms correspond to the detection by HPLC-MSMS of the different using specific MRM transitions on a triple quadrupole mass spectrometer.
Figure 22:
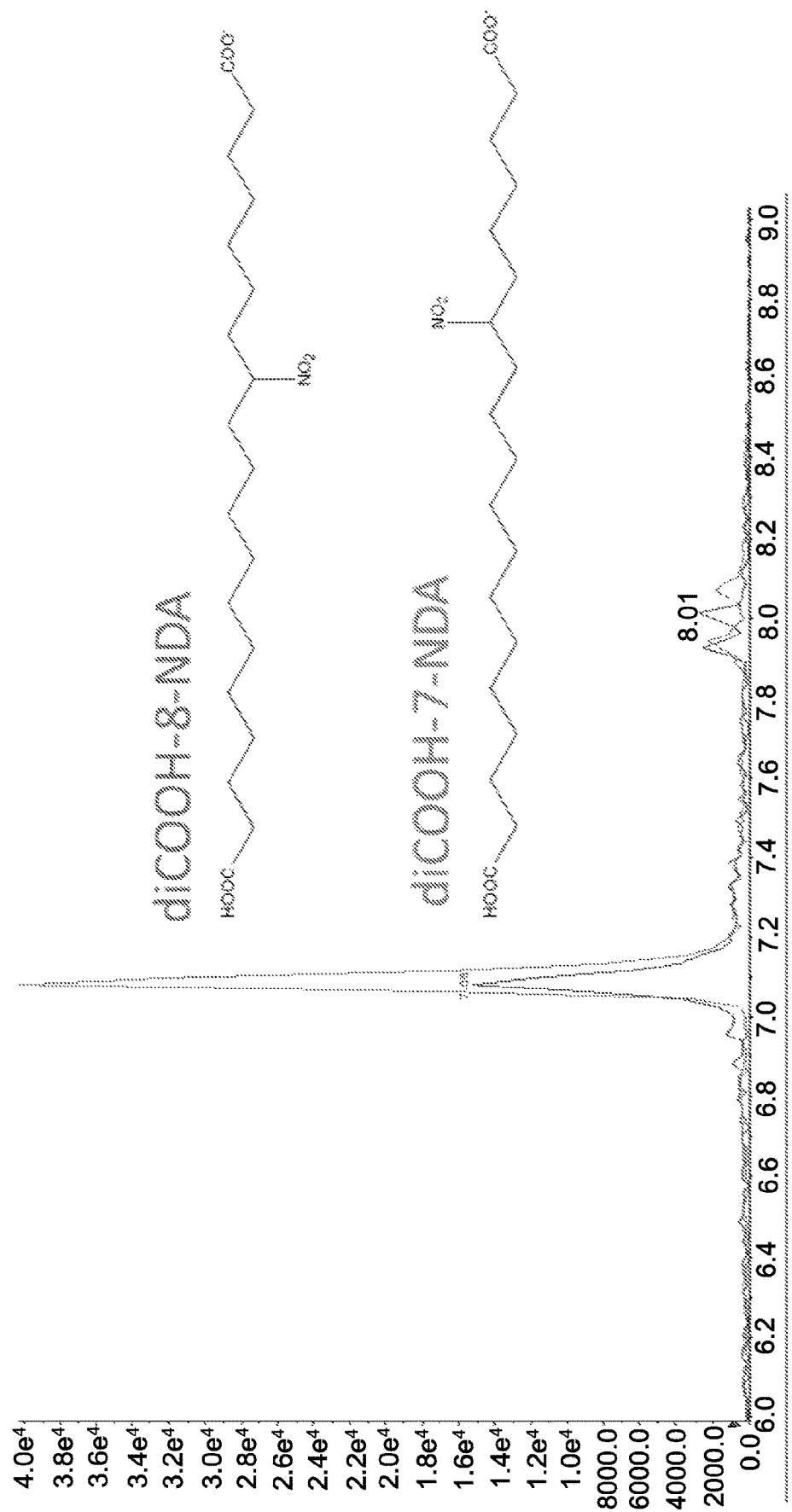

Data show significantly decreased tumor volumes in TNBC xenograft mice treated with nitroalkene fatty acid in combination with PARPi, compared to either NFA or PARPi alone. $1 \times 10^6$ MDA-MB-231 cells were orthotopically injected in the mammary fat pad of nude mice. Tumor volume was measured by caliper over time in mice treated with OA+vehicle (n=8), $NO_2$-OA+vehicle (n=7), OA+talazoparib (0.3 mg/kg) (n=10) or $NO_2$-OA (15 mg/kg)+talazoparib. (FIG. 14)

In view of the many possible embodiments to which the principles of the disclosed invention may be applied, it should be recognized that the illustrated embodiments are only preferred examples of the invention and should not be taken as limiting the scope of the invention.

What is claimed is:

1. A method comprising co-administering to a subject having cancer, suspected of having cancer, at risk of developing cancer, or in cancer remission:
   a therapeutically effective amount of at least one compound (a) selected from (a)(i) a nitroalkene fatty acid, (a)(ii) an unsaturated fatty acid having an electron withdrawing group, a leaving group, and a carbon-carbon double bond disposed between the electron withdrawing group and the leaving group, (a)(iii) a thiolated nitro fatty acid, or (a)(iv) a dicarboxylic acid compound containing an electron withdrawing group; and
   a therapeutically effective amount of at least one antineoplastic agent (b),
   wherein the cancer is a cancer with etiology of defects in DNA repair genes, a cancer with a high rate of spontaneous genomic instability, a cancer that is treated with DNA damaging agent(s), or a cancer that is treated with a combination of DNA damaging agent(s) with immunotherapy.

2. The method of claim 1, wherein the cancer is breast cancer, colon cancer, prostate cancer, pancreatic cancer, ovarian cancer, brain cancer, or skin cancer.

3. The method of claim 1, wherein the cancer is triple negative breast cancer.

4. The method of claim 1, wherein the cancer is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, multiple myeloma, or lymphoma.

5. The method of claim 1, wherein the anti-neoplastic agent is a poly (ADP ribose) polymerase inhibitor.

6. The method of claim 5, wherein the cancer is triple negative breast cancer and the subject is negative for gBRCAm.

7. The method of claim 5, wherein the subject is resistant to monotreatment with a poly (ADP ribose) polymerase inhibitor.

8. The method of claim 1, wherein the anti-neoplastic agent is a DNA-damaging agent or DNA-damaging treatment.

9. The method of claim 1, wherein the anti-neoplastic agent is doxorubicin, cisplatin, olaparib, rucaparib, niraparib, talazoparib, veliparib, camptothecin, or irradiation treatment.

10. The method of claim 1, wherein the compound (a) is a RAD51 inhibitor.

11. The method of claim 1, wherein the compound (a) is the nitroalkene fatty acid.

12. The method of claim 11, wherein the nitroalkene fatty acid is a compound that includes at least one carbon-carbon double bond and at least one nitro group.

13. The method of claim 11, wherein the nitroalkene fatty acid is of formula I:

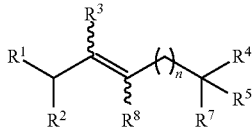

wherein $R^1$ is hydrogen, $C_1$-$C_{24}$ alkyl, $C_1$-$C_{24}$ alkenyl, or $C_1$-$C_{24}$ alkynyl;

$R^2$, $R^3$, $R^7$, and $R^8$ are each independently, hydrogen, oxygen, $C_1$-$C_{24}$ alkyl, $NO_2$, OH, or OOH;

$R^4$ is a terminal $COOR^6$ group, wherein $R^6$ is hydrogen, $C_1$-$C_{24}$ alkyl, or a pharmaceutically acceptable counterion;

$R^5$ is hydrogen, $C_1$-$C_{24}$ alkyl, or $R^4$ and $R^5$ collectively form =$C(R^9)(R^{10})$, wherein $R^9$ comprises $C_1$-$C_{24}$ alkyl, $C_1$-$C_{24}$ alkenyl, or $C_1$-$C_{24}$ alkynyl, or wherein $R^9$ is a terminal $COOR^6$ group, and $R^{10}$ is hydrogen, $NO_2$, OH, or OOH;

n is from 1 to 24; and wherein the nitroalkene fatty acid includes at least one $NO_2$ group.

14. The method of claim 13, wherein $R^1$ is $C_1$-$C_{24}$ alkyl.

15. The method of claim 13, wherein $R^2$ is hydrogen.

16. The method of claim 13, wherein one of $R^3$ or $R^8$ is $NO_2$ and the other of $R^3$ or $R^8$ is hydrogen.

17. The method of claim 13, wherein $R^4$ is —COOH.

18. The method of claim 13, wherein $R^5$ is hydrogen.

19. The method of claim 13, wherein $R^7$ is hydrogen.

20. The method of claim 13, wherein $R^4$ is —COOH; $R^5$ is methyl; and $R^7$ is methyl.

21. The method of claim 11, wherein the nitroalkene fatty acid is 10-nitro-octadec-9-enoic acid.

22. The method of claim 11, wherein the nitroalkene fatty acid is 9-nitro-octadec-9-enoic acid.

23. The method of claim 11, wherein the nitroalkene fatty acid is 7-$NO_2$-nonadec-7-enoic acid.

24. The method of claim 1, wherein the compound (a) is the compound (a)(ii) and compound (a)(ii) is:

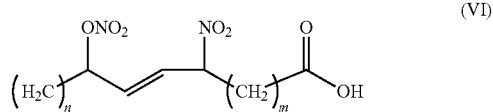
(VI)

wherein m and n are, independently, an integer from 1 to 10.

25. The method of claim 1, wherein the compound (a) is the compound (a)(iii) and compound (a)(iii) is:

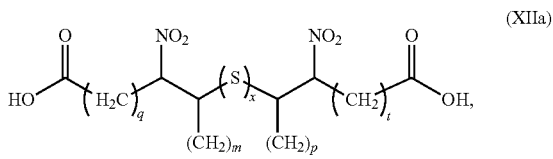
(XIIa)

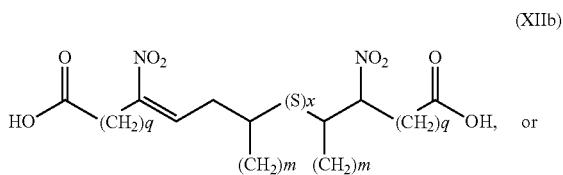
(XIIb)

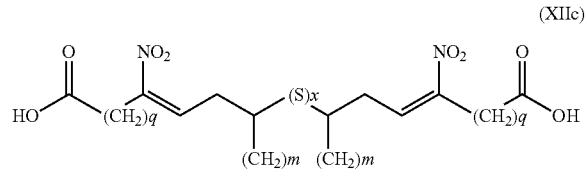
(XIIc)

wherein x is an integer from 1 to 5, and q, m, p, and t are, independently, an integer from 1 to 10.

26. The method of claim 1, wherein the compound (a) is the compound (a)(iv) and compound (a)(iv) is:

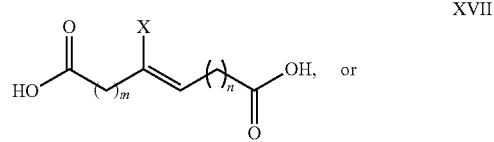
XVII

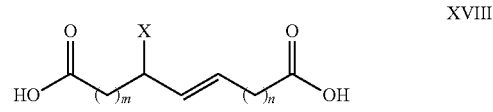
XVIII wherein X is an electron withdrawing group and each m and n are, independently, an integer of 1 to 10, or

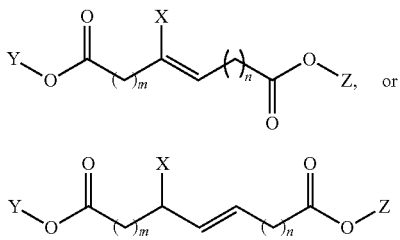

XXI

XXII wherein X is an electron withdrawing group, each Y and Z is, individually, hydrogen or a $C_1$ to $C_{10}$ alkyl, and each m and n are, independently, an integer of 1 to 10.

27. The method of claim 1, wherein the compound (a) is:

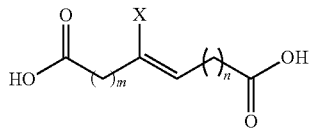

wherein m is from 1 to 10;
n is from 1 to 10;
the double bond is cis to trans; and
X is an electron withdrawing group selected from —$NO_2$, —CN, halide, $C_xF_{2x+1}$, wherein x is from 1 to 5, SOR, wherein R is H or $C_1$-$C_6$ alkyl, $SO_2R$, wherein R is H or $C_1$-$C_6$ alkyl, or $SO_3R$, wherein R is H or $C_1$-$C_6$ alkyl.

28. The method of claim 27, wherein X is —$NO_2$.

29. The method of claim 1, wherein the compound (a) is:

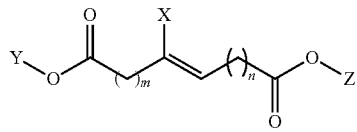

wherein m is from 1 to 10;
n is from 1 to 10;
the double bond is cis to trans;
Y and Z are each, independently a $C_1$ to $C_{10}$ alkyl, alkenyl or alkynyl;
and X is an electron withdrawing group selected from —$NO_2$, —CN, halide, $C_xF_{2x+1}$, wherein x is from 1 to 5, SOR, wherein R is H or $C_1$-$C_6$ alkyl, $SO_2R$, wherein R is H or $C_1$-$C_6$ alkyl, or $SO_3R$, wherein R is H or $C_1$-$C_6$ alkyl.

30. The method of claim 1, wherein the compound (a) is:

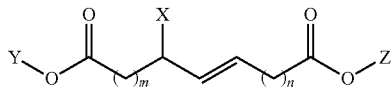

wherein m is from 1 to 10;
n is from 1 to 10;
the double bond is cis to trans;
Y and Z are each, independently a $C_1$ to $C_{10}$ alkyl, alkenyl or alkynyl;
and X is an electron withdrawing group selected from —$NO_2$, —CN, halide, $C_xF_{2x+1}$, wherein x is from 1 to 5, SOR, wherein R is H or $C_1$-$C_6$ alkyl, $SO_2R$, wherein R is H or $C_1$-$C_6$ alkyl, or $SO_3R$, wherein R is H or $C_1$-$C_6$ alkyl.

31. The method of claim 29, wherein m is 2 and n is 2.

32. The method of claim 29, wherein Y and Z are each, independently, a $C_1$ to $C_6$ alkyl.

33. The method of claim 29, wherein Y and Z are each, independently, methyl or ethyl.

34. The method of claim 29, wherein X is —$NO_2$.

35. The method of claim 1, wherein the compound (a) is:

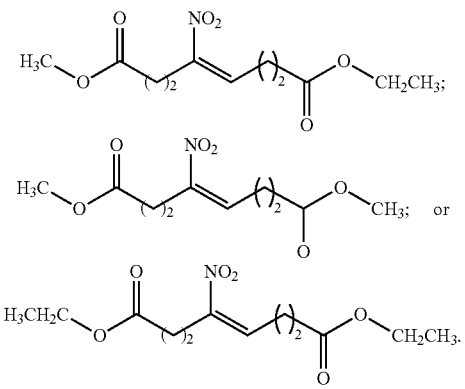

36. A pharmaceutical composition comprising a therapeutically effective amount of at least one compound (a) selected from (a)(i) a nitroalkene fatty acid, (a)(ii) an unsaturated fatty acid having an electron withdrawing group, a leaving group, and a carbon-carbon double bond disposed between the electron withdrawing group and the leaving group, (a)(iii) a thiolated nitro fatty acid, or (a)(iv) a dicarboxylic acid compound containing an electron withdrawing group; and a therapeutically effective amount of at least one anti-neoplastic agent (b).

37. The method of claim 2, wherein the nitroalkene fatty acid is of formula I:

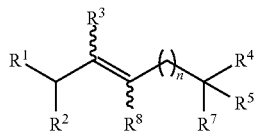

and $R^1$ is $C_1$-$C_{24}$ alkyl; $R^2$, $R^5$ and $R^7$ are each hydrogen; one of $R^3$ or $R^8$ is $NO_2$ and the other of $R^3$ or $R^8$ is hydrogen; and $R^4$ is —COOH.

38. The method of claim 37, wherein the cancer is triple negative breast cancer.

39. The method of claim 37, wherein the anti-neoplastic agent is a poly (ADP ribose) polymerase inhibitor.

40. The method of claim 37, wherein the anti-neoplastic agent is a DNA-damaging agent or DNA-damaging treatment.

41. The method of claim 37, wherein the anti-neoplastic agent is doxorubicin, cisplatin, olaparib, rucaparib, niraparib, talazoparib, veliparib, camptothecin, or irradiation treatment.

42. The method of claim 38, wherein the anti-neoplastic agent is doxorubicin, cisplatin, olaparib, rucaparib, niraparib, talazoparib, veliparib, camptothecin, or irradiation treatment.

43. The method of claim 2, wherein the nitroalkene fatty acid is 7-NO$_2$-nonadec-7-enoic acid.

44. The method of claim 43, wherein the cancer is triple negative breast cancer.

45. The method of claim 43, wherein the anti-neoplastic agent is a poly (ADP ribose) polymerase inhibitor.

46. The method of claim 43, wherein the anti-neoplastic agent is a DNA-damaging agent or DNA-damaging treatment.

47. The method of claim 43, wherein the anti-neoplastic agent is doxorubicin, cisplatin, olaparib, rucaparib, niraparib, talazoparib, veliparib, camptothecin, or irradiation treatment.

48. The method of claim 44, wherein the anti-neoplastic agent is doxorubicin, cisplatin, olaparib, rucaparib, niraparib, talazoparib, veliparib, camptothecin, or irradiation treatment.

49. The method of claim 43, wherein the anti-neoplastic agent is doxorubicin, cisplatin, olaparib, rucaparib, niraparib, talazoparib, veliparib, or camptothecin.

50. The method of claim 44, wherein the anti-neoplastic agent is doxorubicin, cisplatin, olaparib, rucaparib, niraparib, talazoparib, veliparib, or camptothecin.

51. The method of claim 1, wherein the nitroalkene fatty acid is 8-NO$_2$-nonadec-7-enoic acid.

52. The method of claim 2, wherein the nitroalkene fatty acid is 8-NO$_2$-nonadec-7-enoic acid.

53. The method of claim 52, wherein the anti-neoplastic agent is a poly (ADP ribose) polymerase inhibitor.

54. The method of claim 52, wherein the anti-neoplastic agent is a DNA-damaging agent or DNA-damaging treatment.

55. The method of claim 52, wherein the anti-neoplastic agent is doxorubicin, cisplatin, olaparib, rucaparib, niraparib, talazoparib, veliparib, camptothecin, or irradiation treatment.

56. The method of claim 1, wherein the cancer is a cancer with hereditary etiology of defects in DNA repair genes.

57. The method of claim 37, wherein the cancer is a cancer with hereditary etiology of defects in DNA repair genes.

\* \* \* \* \*